US010946066B2

(12) United States Patent
Rafii et al.

(10) Patent No.: US 10,946,066 B2
(45) Date of Patent: Mar. 16, 2021

(54) METHODS FOR ORGAN REGENERATION

(75) Inventors: Shahin Rafii, New York, NY (US); Bi-Sen Ding, Bloomfield, NJ (US); Sina Y. Rabbany, Great Neck, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 13/884,484

(22) PCT Filed: Nov. 9, 2011

(86) PCT No.: PCT/US2011/059960
§ 371 (c)(1),
(2), (4) Date: May 17, 2013

(87) PCT Pub. No.: WO2012/064834
PCT Pub. Date: May 18, 2012

(65) Prior Publication Data
US 2013/0224161 A1 Aug. 29, 2013

Related U.S. Application Data

(60) Provisional application No. 61/411,732, filed on Nov. 9, 2010, provisional application No. 61/545,851, filed on Oct. 11, 2011.

(51) Int. Cl.
| | |
|---|---|
| *A61K 38/18* | (2006.01) |
| *A61K 35/44* | (2015.01) |
| *C12N 5/071* | (2010.01) |
| *A61K 35/12* | (2015.01) |

(52) U.S. Cl.
CPC .......... *A61K 38/1866* (2013.01); *A61K 35/12* (2013.01); *A61K 35/44* (2013.01); *A61K 38/1825* (2013.01); *C12N 5/067* (2013.01); *C12N 2502/28* (2013.01)

(58) Field of Classification Search
None
See application file for complete search history.

(56) References Cited

U.S. PATENT DOCUMENTS

| 2008/0050349 A1* | 2/2008 | Stewart ....................... 424/93.21 |
| 2014/0147503 A1 | 5/2014 | Malhotra et al. | |

FOREIGN PATENT DOCUMENTS

| EP | 2 103 683 A1 | 9/2009 |
| JP | 2007-130179 A | 5/2007 |
| JP | 2008-519598 A | 6/2008 |
| JP | 2008-283981 A | 11/2008 |
| JP | 2013-538845 A | 10/2013 |
| WO | WO 02/062971 A1 | 8/2002 |
| WO | WO 03/103581 A2 | 12/2003 |
| WO | WO 2006/052223 A1 | 5/2006 |
| WO | WO 2008/088042 A1 | 7/2008 |
| WO | WO-2008089448 A2 * | 7/2008 ........... C07K 14/005 |

OTHER PUBLICATIONS

Lalor et al. "Human hepatic sinusoidal endothelial cells can be distinguished by expression of phenotypic markers related to their specialized functions in vivo", World Journal of Gastroenterology 12(34): 5429-39, 2006.*
Rafii et al. "Therapeutic stem and progenitor cell transplantation for organ vascularization and regeneration", Nature Medicine 9(6): 702-712, 2003.*
Mondrinos et al. "In vivo pulmonary tissue engineering: Contribution of donor-derived endothelial cells to construct vascularization", Tissue Engineering: Part A 14(3): 361-368, 2007.*
Cortiella et al. "Tissue-engineered lung: an in vivo and in vitro comparison of polyglycolic acid and pluronic F-127 hydrogel/somatic lung progenitor cell constructs to support tissue growth", Tissue Engineering 12(5): 1213-1225, 2006.*
Rafii et al. "Therapeutic stem and progenitor cell transplantation for organ vascularization and regeneration", Nature Medicine 9(6): 702-12, 2003.*
Ewing et al. "Isolation and transplantation of allogeneic pulmonary endothelium derived from GFP transgenic mice", Journal of Immunological Methods 283: 307-15, 2003.*
Panoskaltsis-Mortari et al. "The critical early proinflammatory events associated with idiopathic pneumonia syndrome in irradiated murine allogeneic recipients are due to donor T cell infusion and potentiated by cyclophosphamide." Journal of Clinical Investigation 100(5): 1015-1027, 1997 (Year: 1997).*
White et al. "FGF9 and SHH regulate mesenchymal Vegfa expression and development of the pulmonary capillary network." Development 134.20 (2007): 3743-3752 (Year: 2007).*
Yañez-Mó et al. "MT1-MMP collagenolytic activity is regulated through association with tetraspanin CD151 in primary endothelial cells." Blood 112.8 (2008): 3217-3226 (Year: 2008).*
Alvarez, D. F. et al., "Lung microvascular endothelium is enriched with progenitor cells that exhibit vasculogenic capacity", Am J Physiol Lung Cell Mol Physiol 294:L419-:L430 (2008).
Benten, D. et al., "Hepatic Targeting of Transplanted Liver Sinusoidal Endothelial Cells in Intact Mice", Hepatology 42:140-148 (2005).
Ding, B. et al., "Divergent angiocrine signals from vascular niche balance liver regeneration and fibrosis", Nature 505:97-103 (2014).
Follenzi, A. et al., "Transplanted endothelial cells repopulate the liver endothelium and correct the phenotype of hemophilia A mice", The Journal of Clinical Investigation 118(3):935-945 (2008).
Greene, A. K. et al., "Endothelial-Directed Hepatic Regeneration After Partial Hepatectomy", Annals of Surgery 237(4):530-535 (2003).

(Continued)

*Primary Examiner* — Emily A Cordas
(74) *Attorney, Agent, or Firm* — Scully, Scott, Murphy & Presser, P.C.

(57) ABSTRACT

A method of enhancing or initiating regeneration of an organ in a subject in need thereof comprising the administration of endothelial cells specific to said organ, or inductive endothelial cells specific to said organ, into the area of the body in which organ regeneration is desired in said subject.

8 Claims, 49 Drawing Sheets

(56) References Cited

OTHER PUBLICATIONS

Hermanns, M. I. et al., "Lung epithelial cell lines in coculture with human pulmonary microvascular endothelial cells: development of an alveolo-capillary barrier in vitro", Laboratory Investigation 84:736-752 (2004).
International Search Report and Written Opinion issued in International Application No. PCT/US2011/059960 dated May 23, 2012.
Nahmias, Y. et al., "Liver Endothelial Cells Promote LDL-R Expression and the Uptake of HCV-Like Particles in Primary Rat and Human Hepatocytes", Hepatology 43:257-265 (2006).
Wang, X, et al., "Transplantation of Autologous Endothelial Progenitor Cells May Be Beneficial in Patients With Idiopathic Pulmonary Arterial Hypertension A Pilot Randomized Controlled Trial" Journal of the American College of Cardiology 49(14):1566-1571 (2007).
Zaret, K. S. et al., "Generation and Regeneration of Cells of the Liver and Pancreas", Science 322:1490-1494 (2008).
European Search Report for European Patent Appln. No. 11839627. 4, dated Apr. 9, 2015.
Kobayshi, Hideki, et al., "Angiocrine factors from Akt-activiated endothelial cells balance self-renewal and differentiation of haematopoietic stem cells"; Nature Cell Biology, vol. 12, No. 11, Oct. 24, 2010, pp. 1046-1056.
Kumaran, V., et al., "Transplantation of endothelial cells corrects the phenotype in hemophilioa A mice"; Journal of Thrombosis and Haemostasis, 3:No. 9; pp. 2022-2031, Sep. 1, 2015.
Follenzi A. et al., "Altering Transplanted Cell Engraftment and Proliferation in the Liver Through Paracrine Signaling With Cotransplantation of Liver Sinusoidal Endothelial Cells (LSEC) and Hepatocytes in Mice", Hepatology 46(4), Suppl. 1, pp. 785A-786A (Oct. 1, 2007).
Ding B-S et al., "Endothelial-Derived Angiocrine Signals Induce and Sustain Regenerative Lung Alveolarization", Cell 147(3):539-553 (Oct. 28, 2011).
Lecouter J. et al., "Angiogenesis-Independent Endothelial Protection of Liver: Role of VEGFR-1", Science 299(5608):890-893 (Feb. 7, 2003).
Wirz W. et al., "Hepatic Stellate Cells Display a Functional Vascular Smooth Muscle Cell Phenotype in a Three-Dimensional Co-Culture Model With Endothelial Cells", Differentiation 76(7):784-794 (Sep. 1, 2008).
Xia L. et al., "Endothelial Progenitor Cells May Inhibit Apoptosis of Pulmonary Microvascular Endothelial Cells: New Insights into Cell Therapy for Pulmonary Arterial Hypertension", Cytotherapy 11(4):492-502 (Jan. 1, 2009).
Extended Supplementary European Search Report dated Sep. 25, 2015 received from European Application No. 11839627.4.
Kobayashi H. et al., "Angiocrine Factors from Akt-Activated Endothelial Cells Balance Self-Renewal and Differentiation of Haematopoietic Stem Cells", *Nature Cell Biology* 12(11):1046-1056 (Oct. 24, 2010).
Owarini et al., "Vascular Endothelial Growth Factor", *Kokyu Breathing* 25(9):848-855 (2009), together with an English-language abstract.
Nihon-Isikai-Zasshi, *The Japan Medical Associate Magazine* 129(3):369-372 (2003), together with an English-language abstract.
Japanese Notice of Reasons for Rejection dated Sep. 6, 2016 received in Japanese Patent Application No. 2013-538845, together with an English-language translation.
Australian Examination Report dated Feb. 5, 2016 received from Australian Patent Application No. 2011326562.

Japanese Patent Application No. 2008-519598 A, dated Jun. 12, 2008, together with an English-language abstract, corresponds to PCT International Publication No. WO 2006/052223 A1, published May 18, 2006.
Japanese Patent Application No. 2008-283981 A, dated Nov. 27, 2008, together with an English-language abstract, corresponds to PCT International Publication No. WO 02/062971 A1, published Aug. 15, 2002.
Japanese Patent Application No. 2007-130179 A, dated May 31, 2007, together with an English-language abstract.
PCT International Publication No. WO 2008/088042 A1, published Jul. 24, 2008, corresponds to European Patent Application No. 2 103 683 A1, dated Sep. 23, 2009.
Takuji T. et al., *Molecular Digestive Disorder* 4(4):315-321 (2007), together with an English-language abstract.
Daneker G.W. et al., "Culture and Characterization of Sinusoidal Endothelial Cells Isolated from Human Liver", *In Vitro Cell Dev. Biol.-Animal* 34:370-377 (May 1998).
Myronovych A., *Liver 50, suppl.* (1), A176, O-176 (2009), the English-language abstract of which is not available; however, see p. 4 of the English-language translation of the Japanese Notice of Reasons for Rejection.
Japanese Notice of Reasons for Rejection dated Sep. 8, 2015 received from Japanese Application No. 2013-538845.
Japanese Notice of Reasons for Rejection dated Sep. 8, 2015 received from Japanese Application No. 2013-538845, together with an English-language translation.
Cowan, M. J., et al., "Lung Growth after Unilateral Pneumonectomy: Quantitation of Collagen Synthesis and Content", American Review of Respiratory Disease, 1975, pp. 267-277, vol. III.
Leuwerke, S. M., et al., "Inhibition of compensatory lung growth in endothelial nitric oxide synthase-deficient mice", Am J Physiol Lung Cell Mol Physiol, First published Feb. 1, 2002, pp. L1272-L1278, 282.
Nolen-Walston, R. D., et al., "Cellular kinetics and modeling of bronchioalveolar stem cell response during lung regeneration", Am J Physiol Lung Cell Mol Physiol, First published Mar. 28, 2008, pp. L1158-L1165, 294.
Yana, I., et al., "Crosstalk between neovessels and mural cells directs the site-specific expression of MT1-MMP to endothelial tip cells", Journal of Cell Science, Accepted Mar. 18, 2007, pp. 1607-1614, 120, Published by The Company of Biologists.
Ackah, E. et al., "Akt1 /protein kinase B alpha is critical for ischemic and VEGF-mediated angiogenesis", The Journal of Clinical Investigation, vol. 115, No. 8, pp. 2119-2127 (Aug. 1, 2005).
Ding, B. et al., "Inductive angiocrine signals from sinusoidal endothelium are required for liver regeneration", Nature, vol. 468, No. 7321, pp. 310-315 (Nov. 11, 2010).
Ding, B. et al., "Endothelial-Derived Angiocrine Signals Induce and Sustain Regenerative Lung Alveolarization", Cell, vol. 147, No. 3, pp. 539-553,S1-S7 (Oct. 28, 2011).
Murakami, M. et al., "FGF-dependent regulation of VEGF receptor 2 expression in mice", The Journal of Clinical Investigation, vol. 121, No. 7, pp. 2668-2678 (Jul. 1, 2011).
Extended European Search Report dated Aug. 13, 2020 in European Patent Application No. 20 16 0502.9.
Tazawa, J. et al., "Development of next-generation mucosal vaccine based on DDS technology", Drug Delivery System, vol. 23, No. 2, pp. 116-122 (2008), English-language abstract.
Japanese Office Action dated Nov. 10, 2020 in Japanese Patent Application No. 2019-193924, together with an English language translation.

* cited by examiner

A

B

Figure 2 (con't)
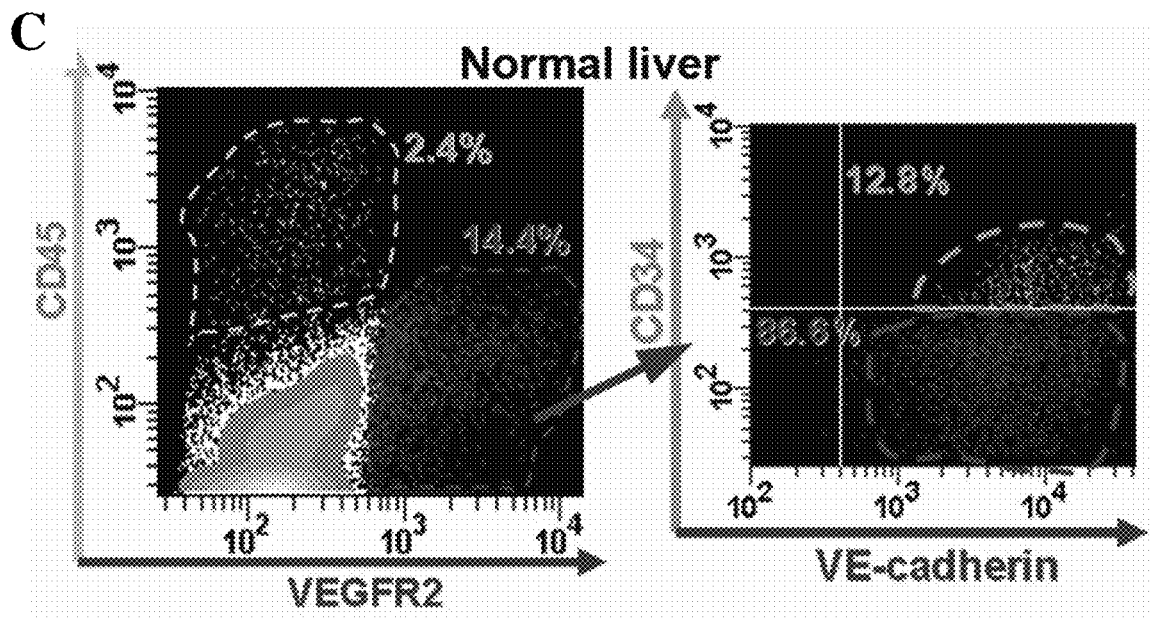
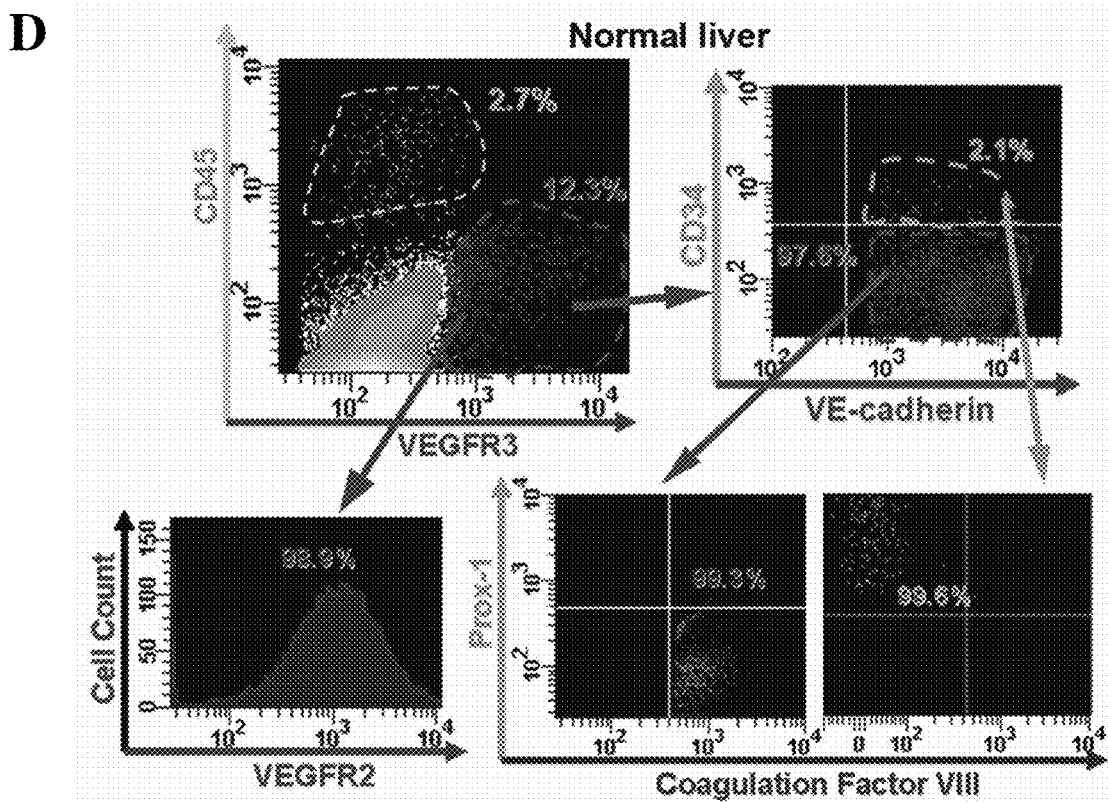

Figure 2 (con't)
E 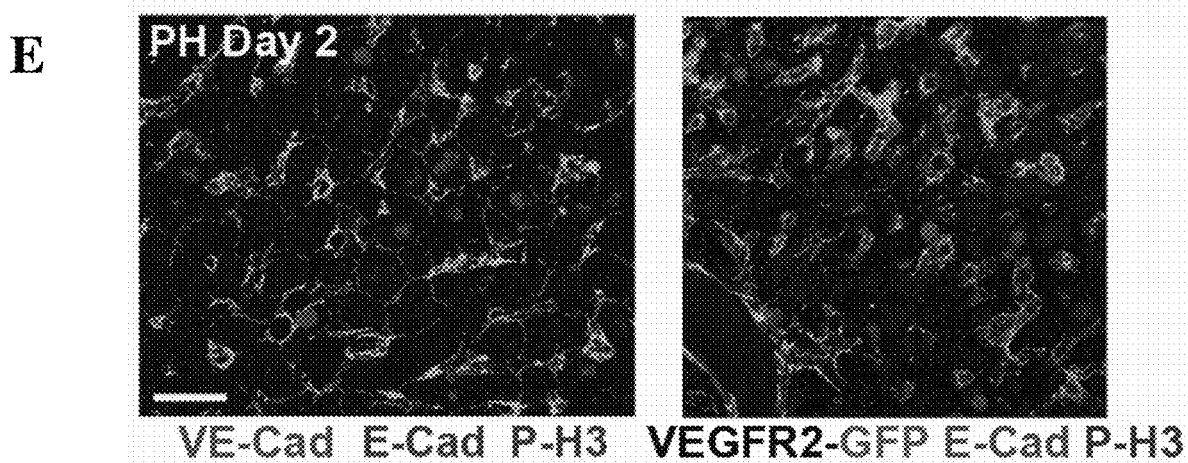
F 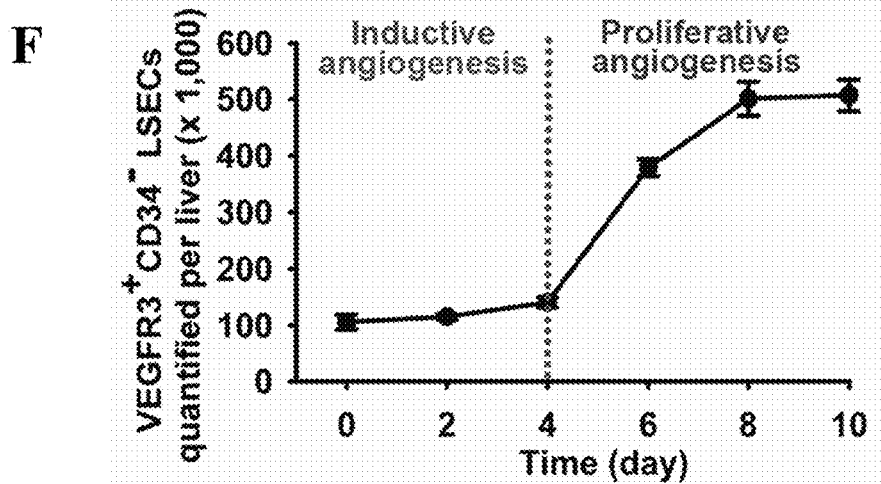
G 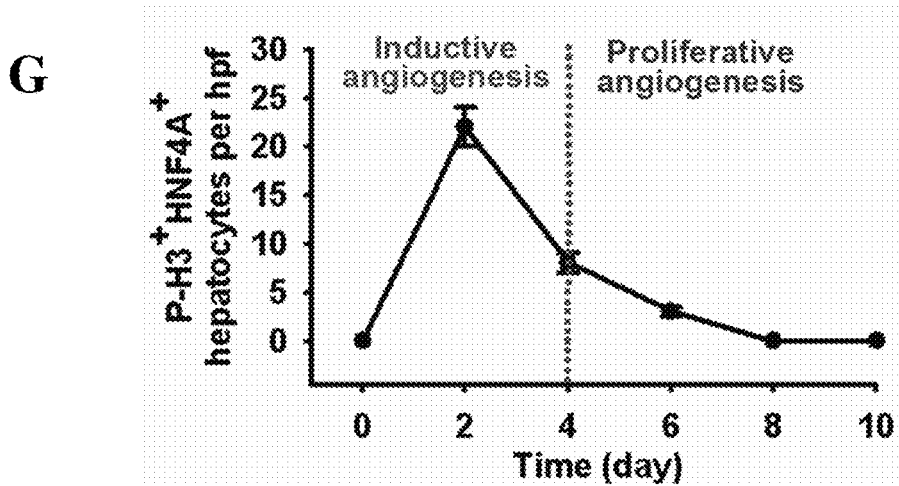

Figure 3 (con't)
C
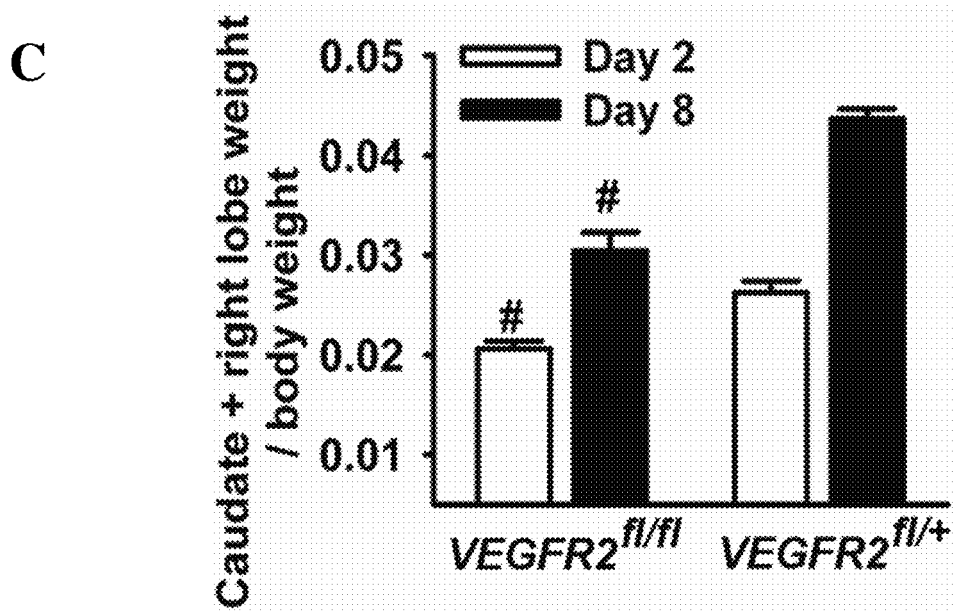
D
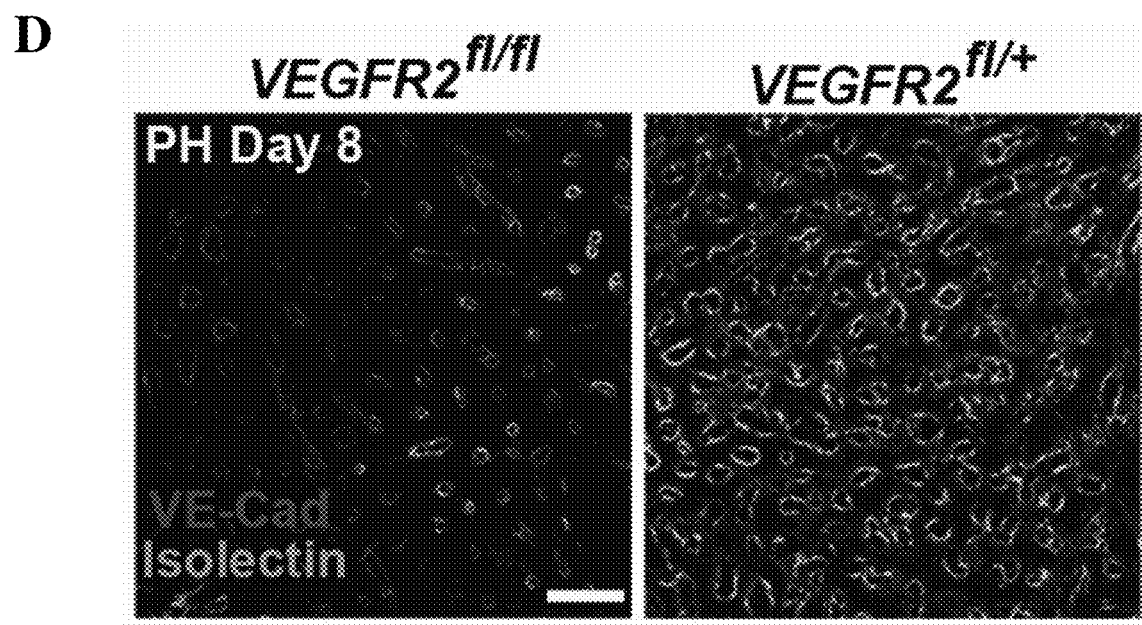

Figure 3 (con't)
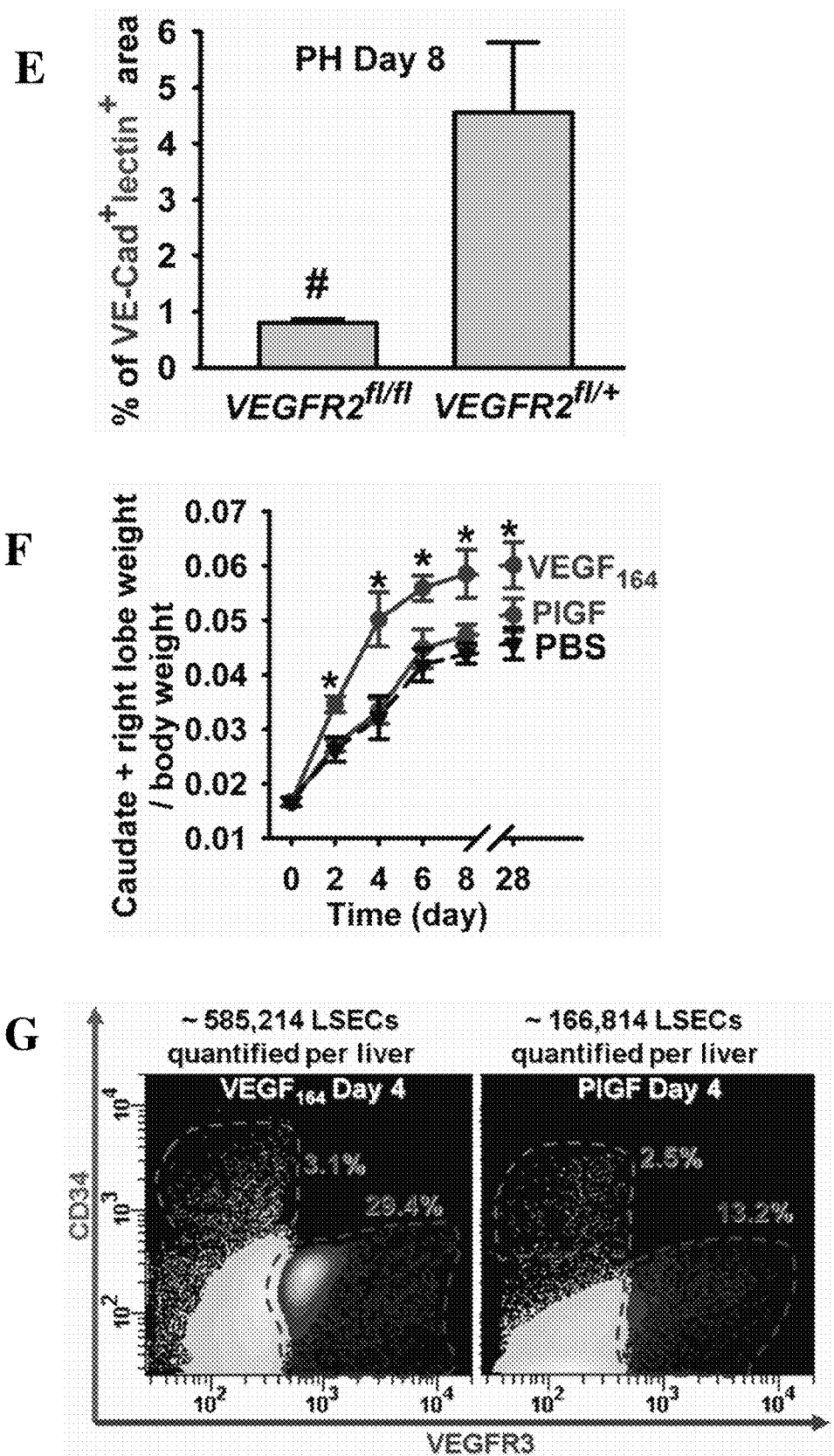

Figure 3 (con't)
H 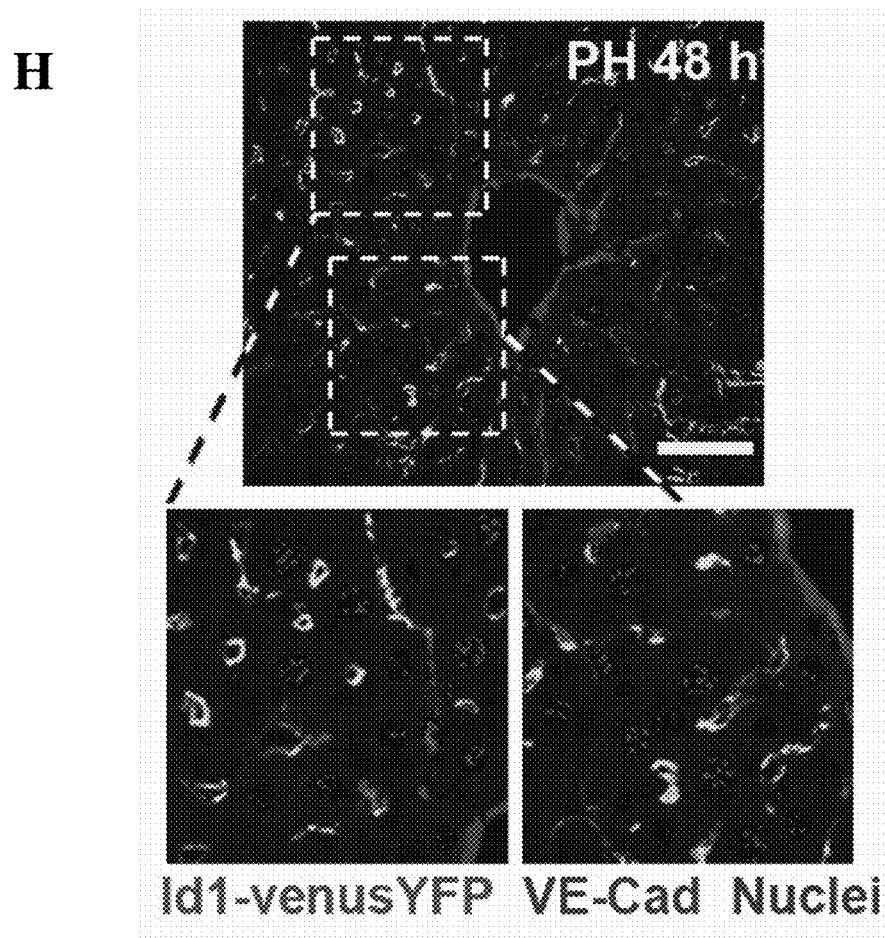
I 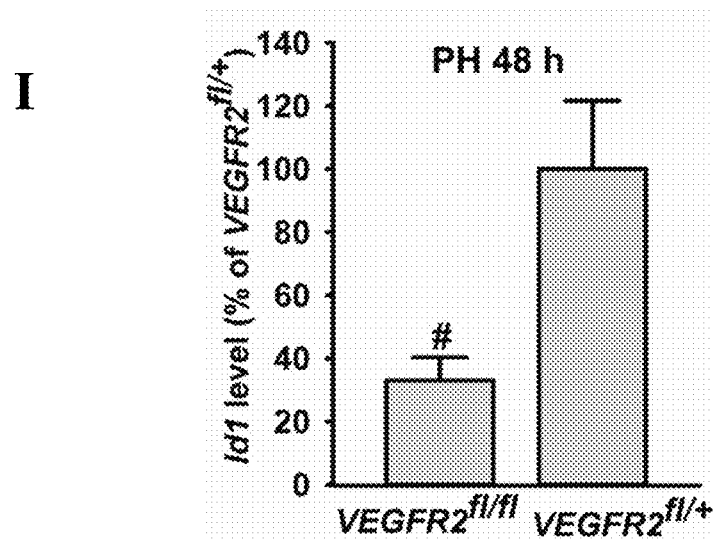

Figure 3 (con't)
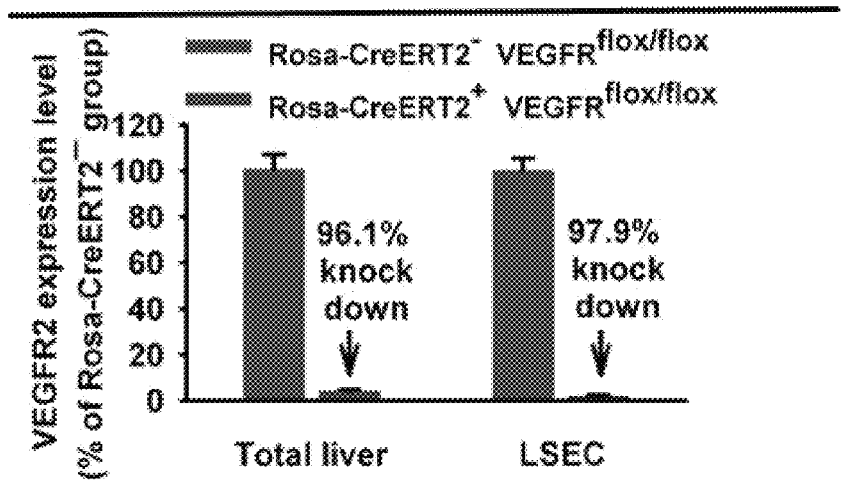
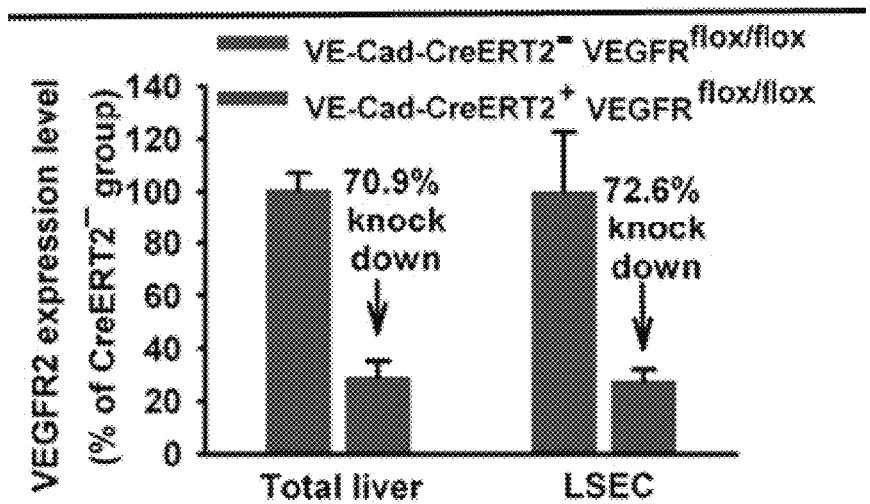

Figure 4 (con't)
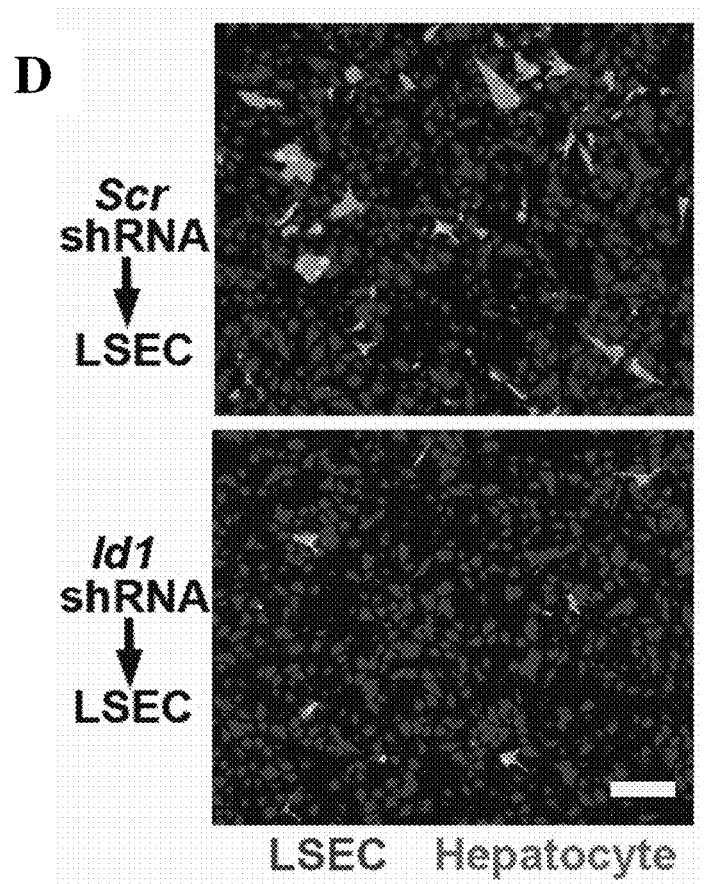
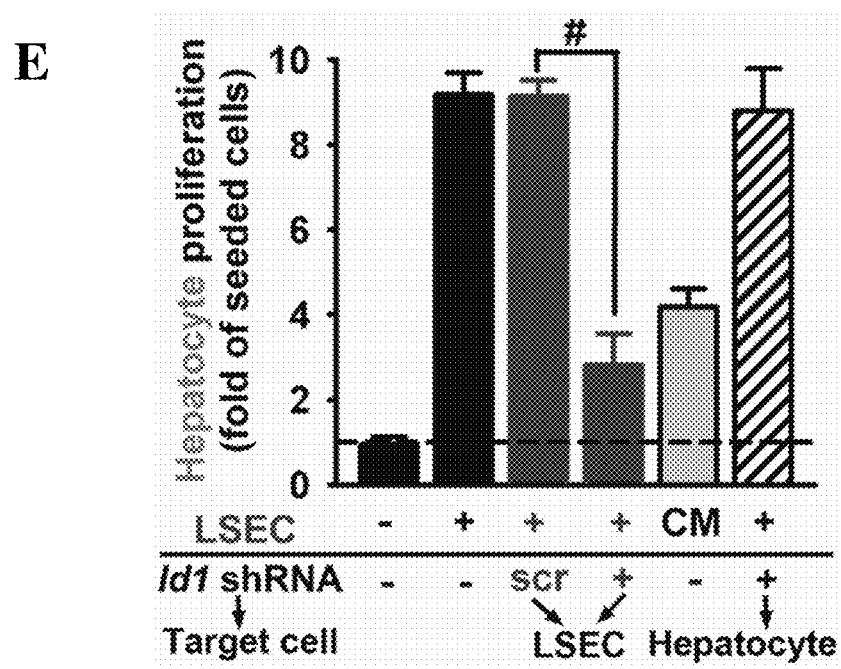

Figure 4 (con't)
F
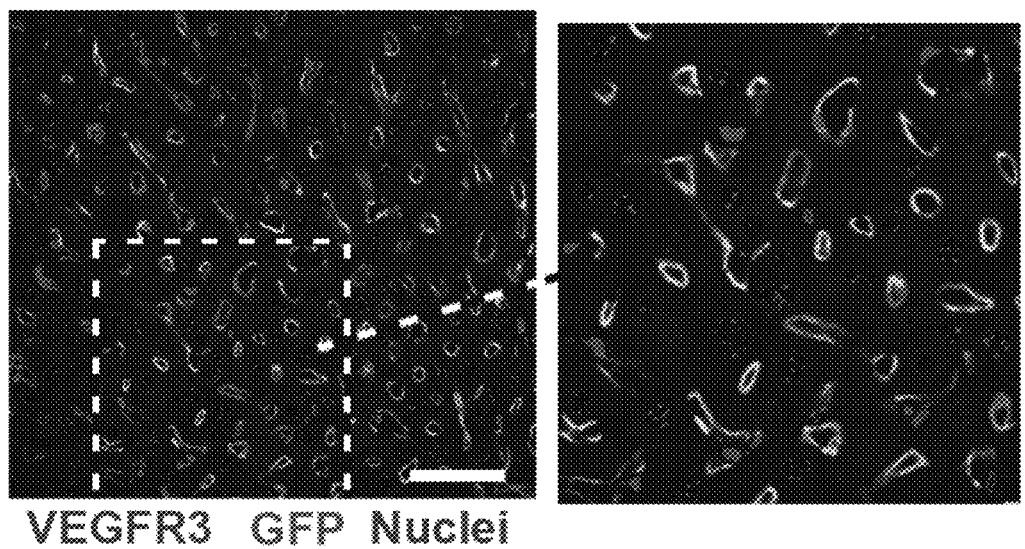
VEGFR3  GFP  Nuclei
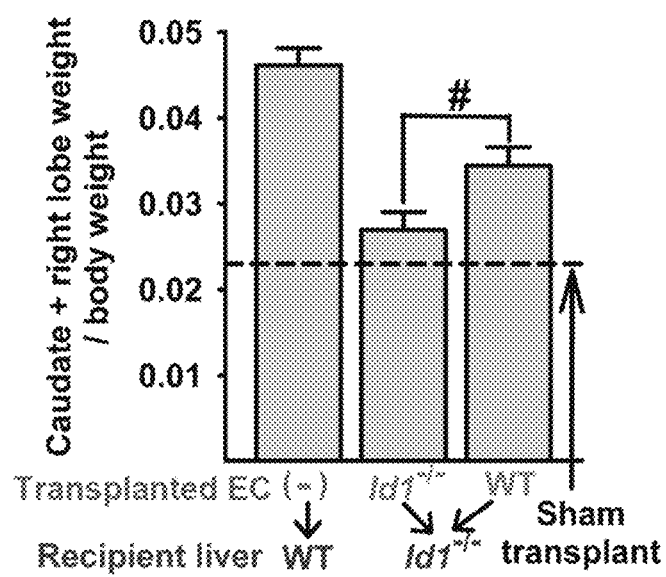

Figure 4 (con't)
H
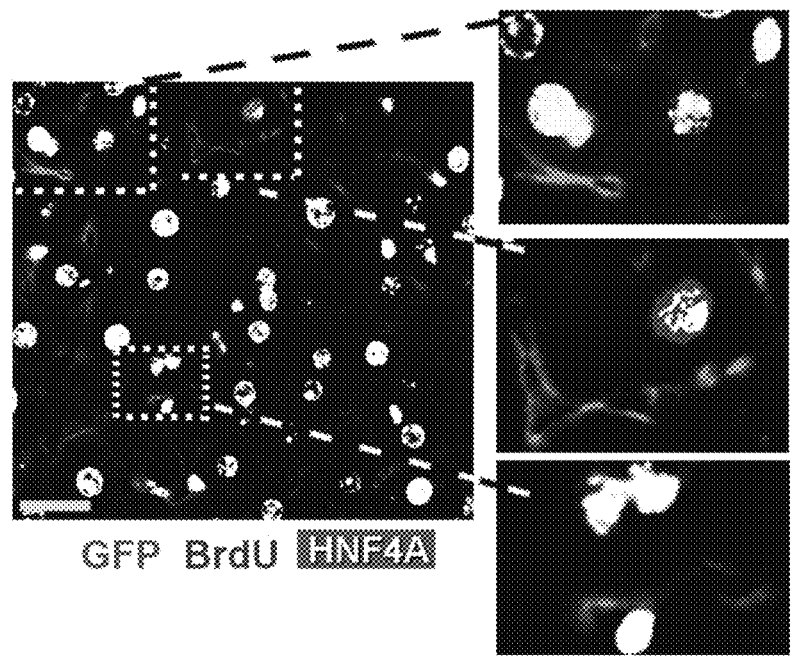
I
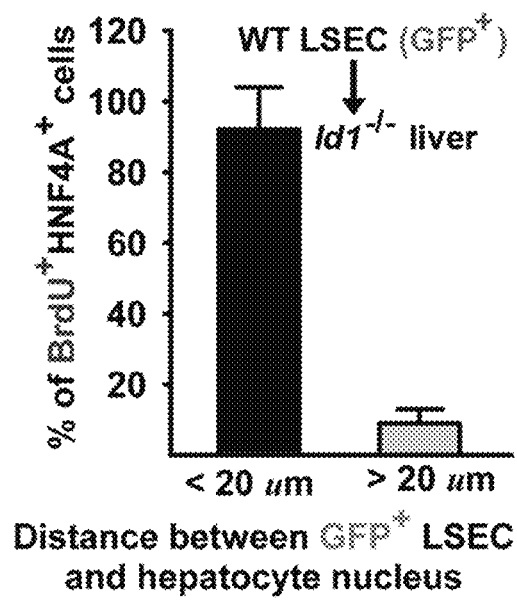
Distance between GFP+ LSEC and hepatocyte nucleus Figure 4 (con't)
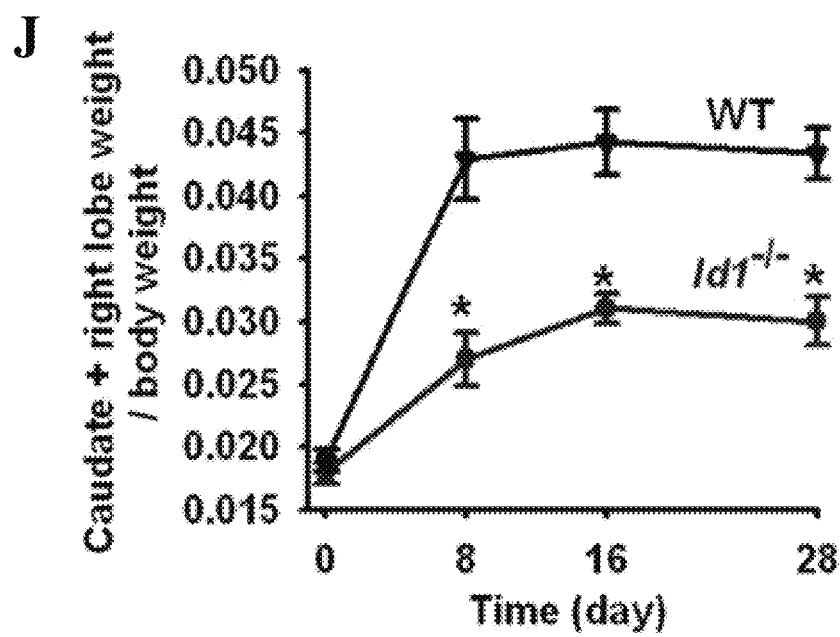
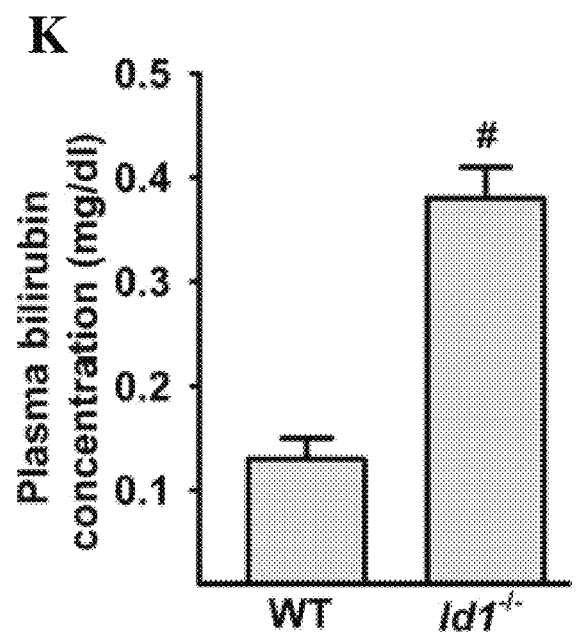

Figure 5 (con't)
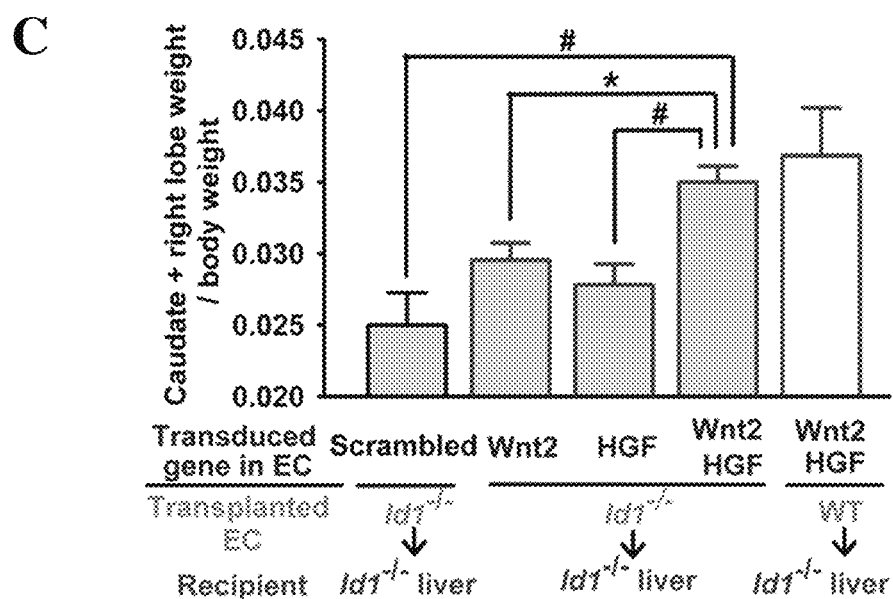
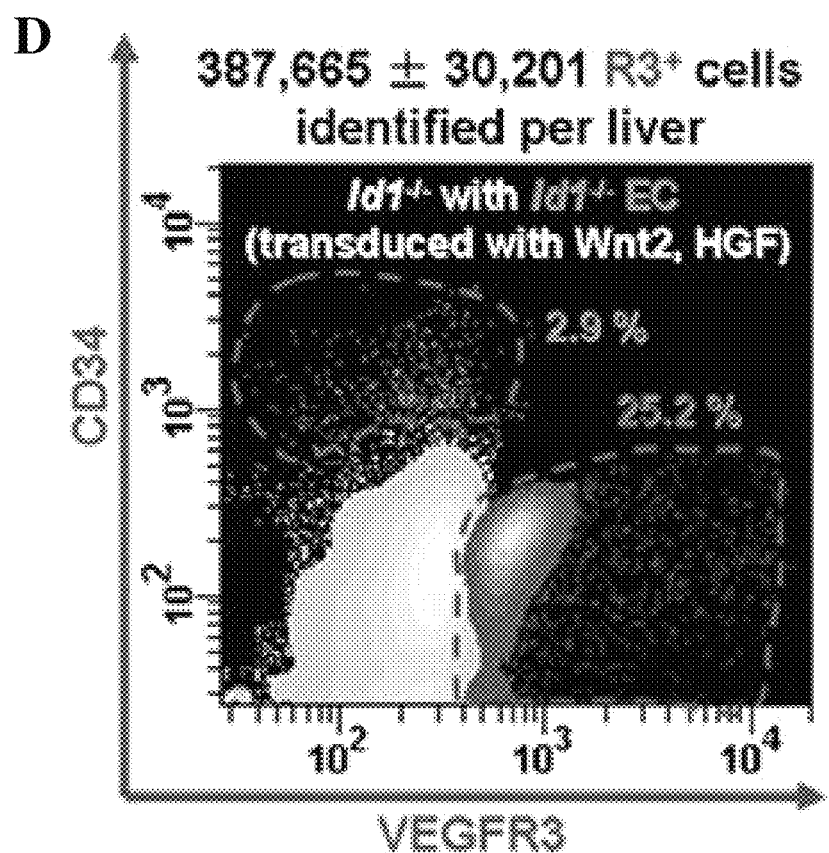

Figure 5 (con't)
E
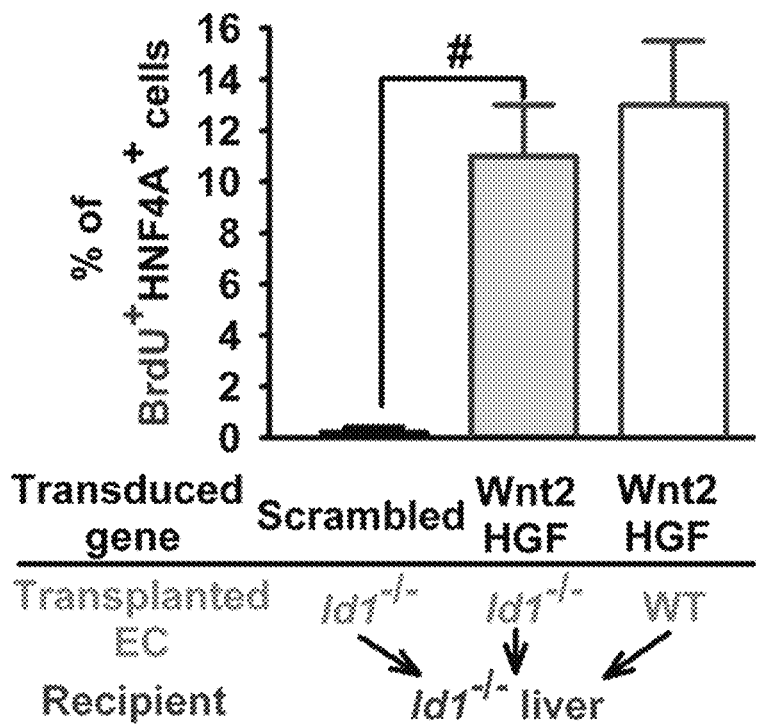
F
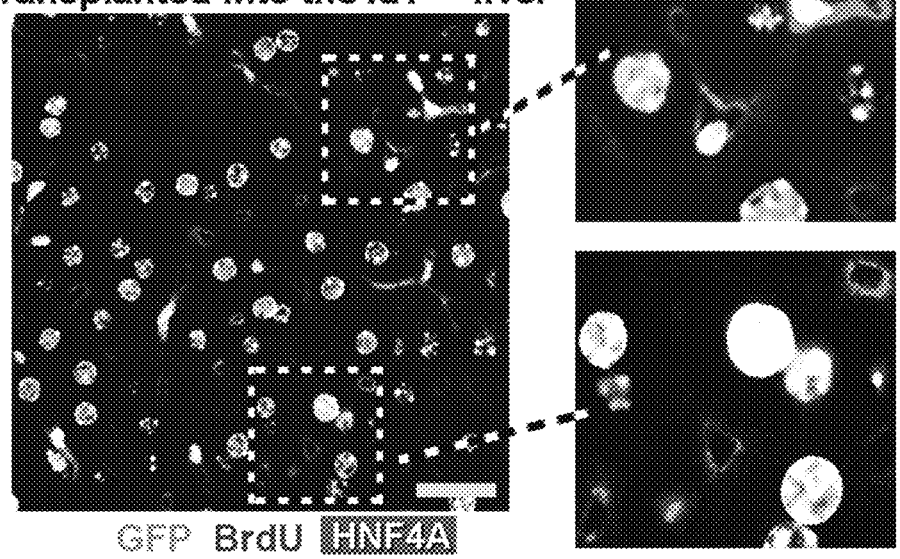

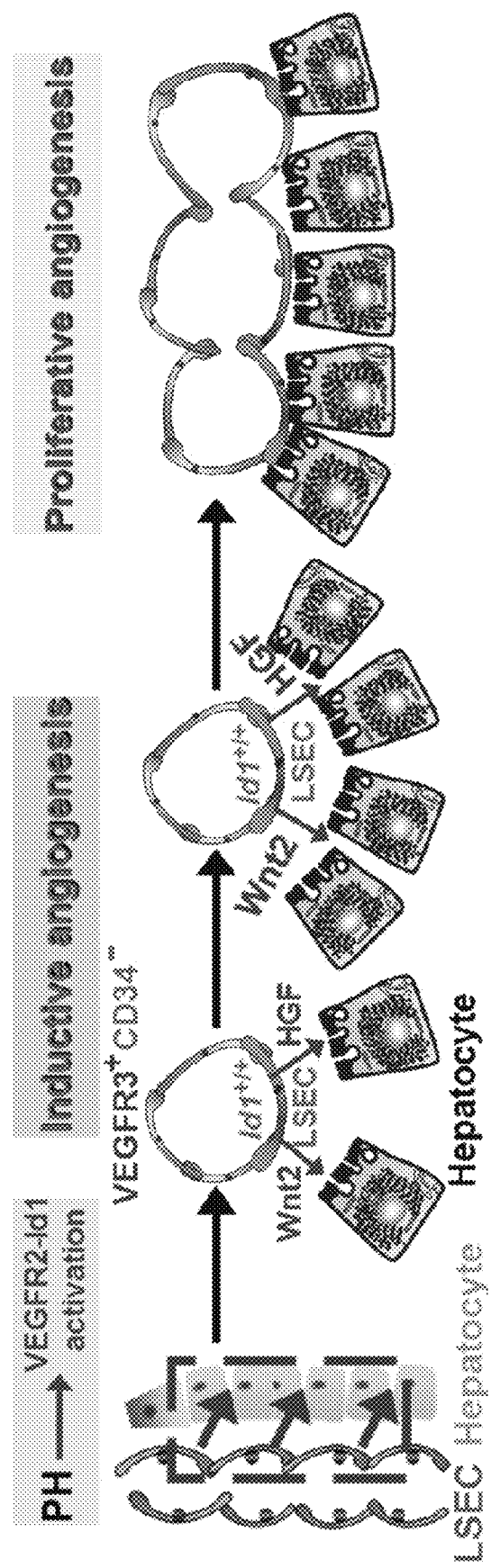
Figure 5 (con't)

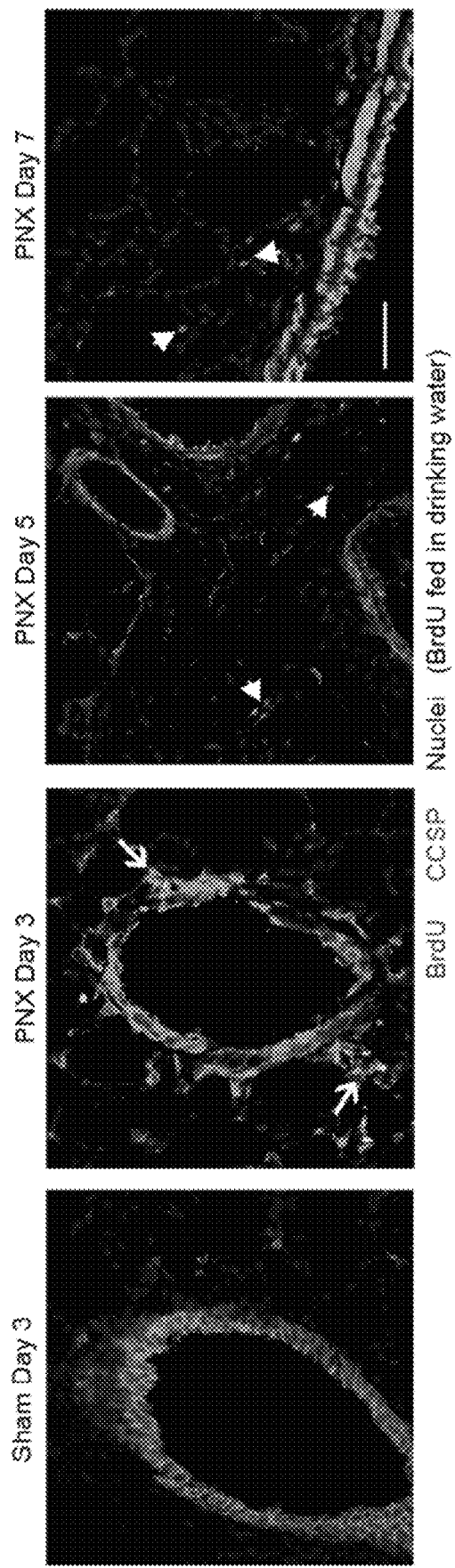
Figure 6 (con't)

Figure 6 (con't)
D
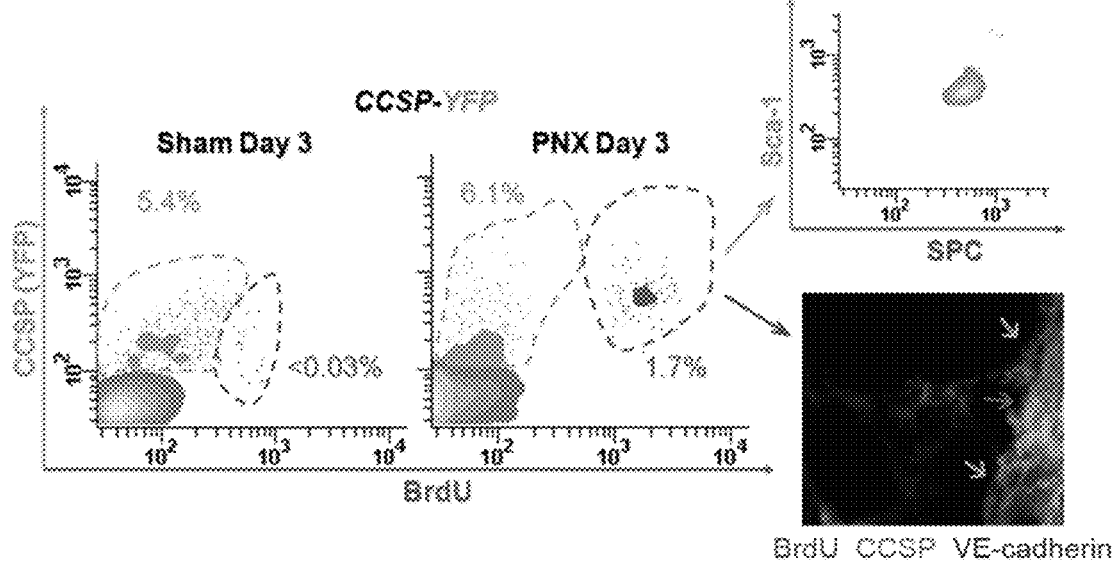
E
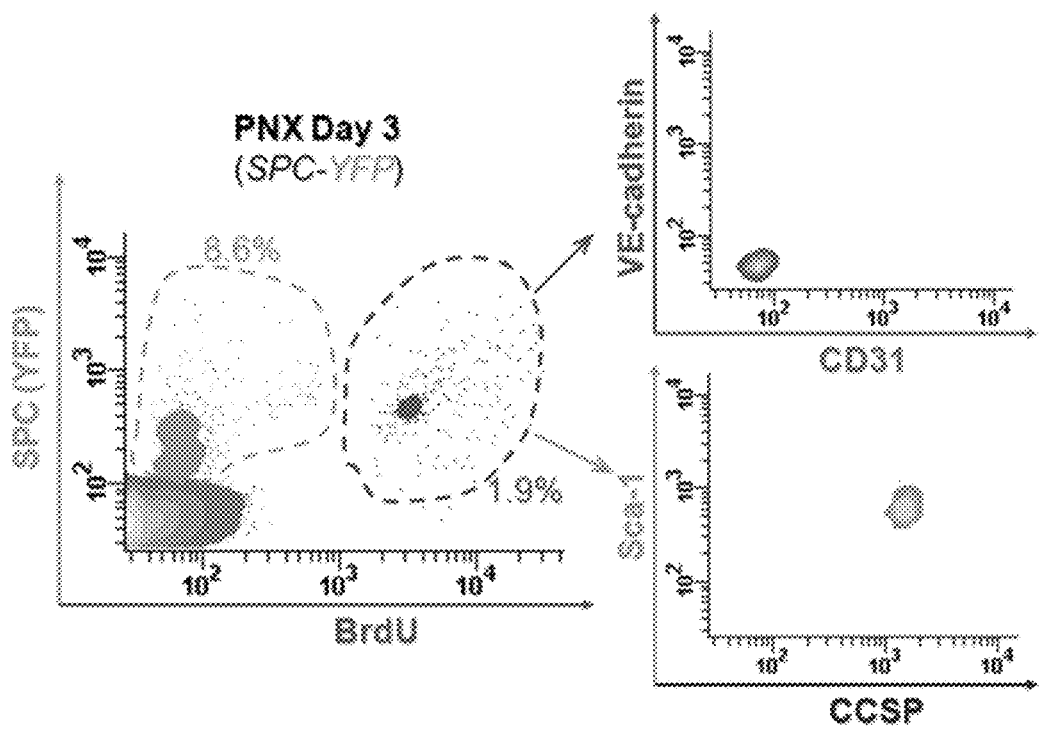

Figure 7 (con't)
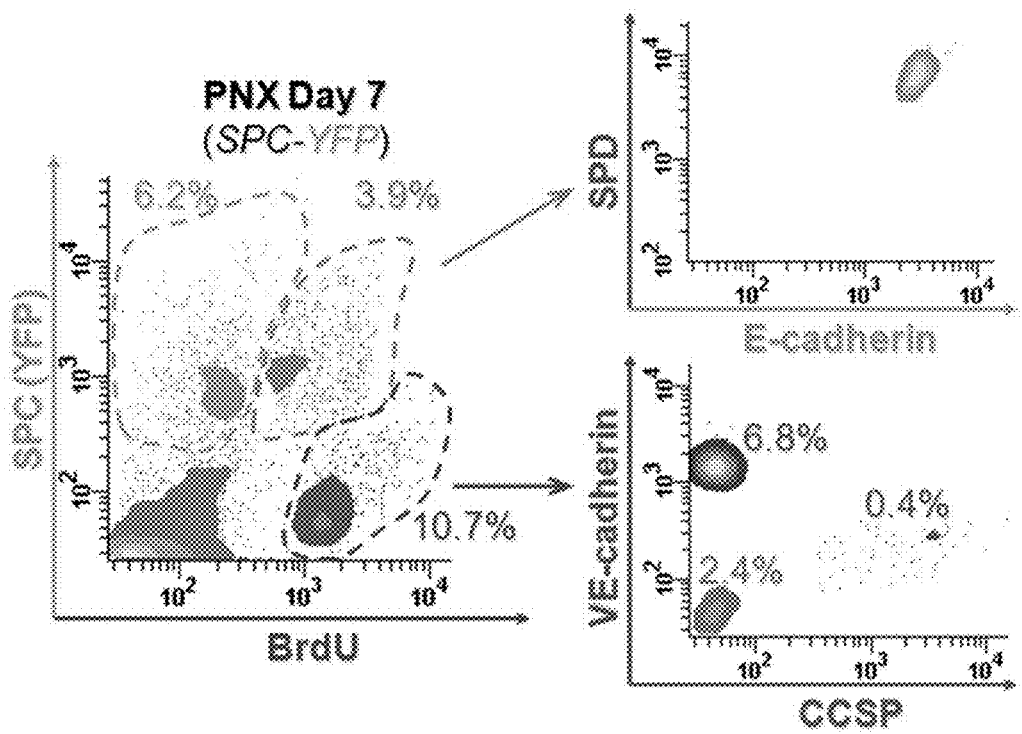
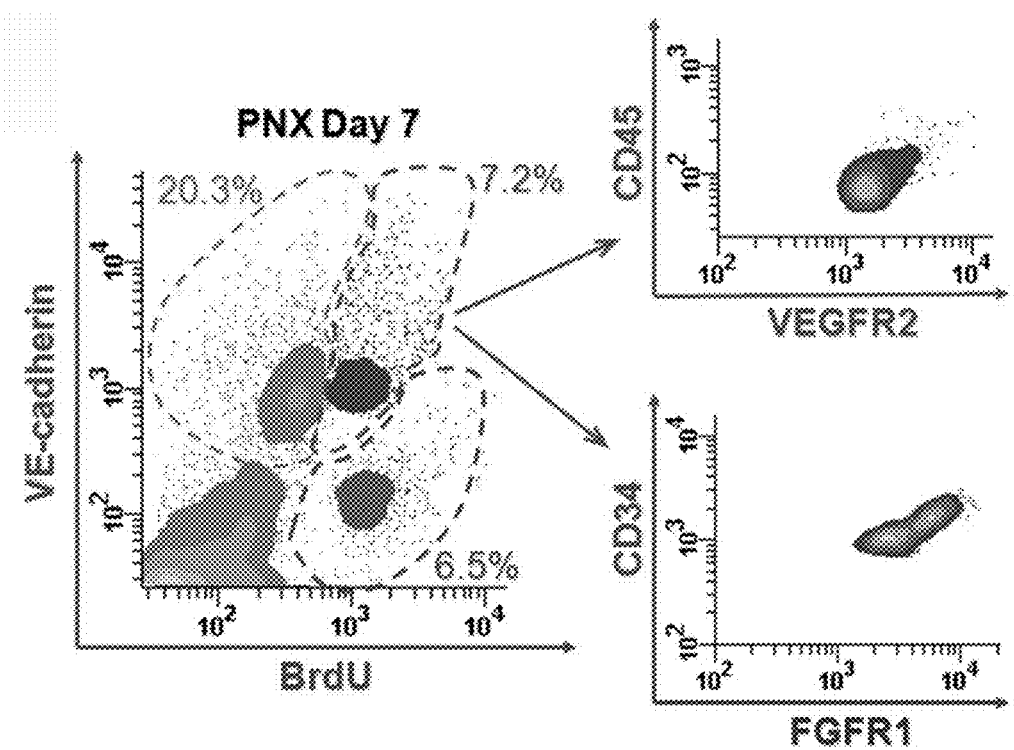

Figure 7 (con't)
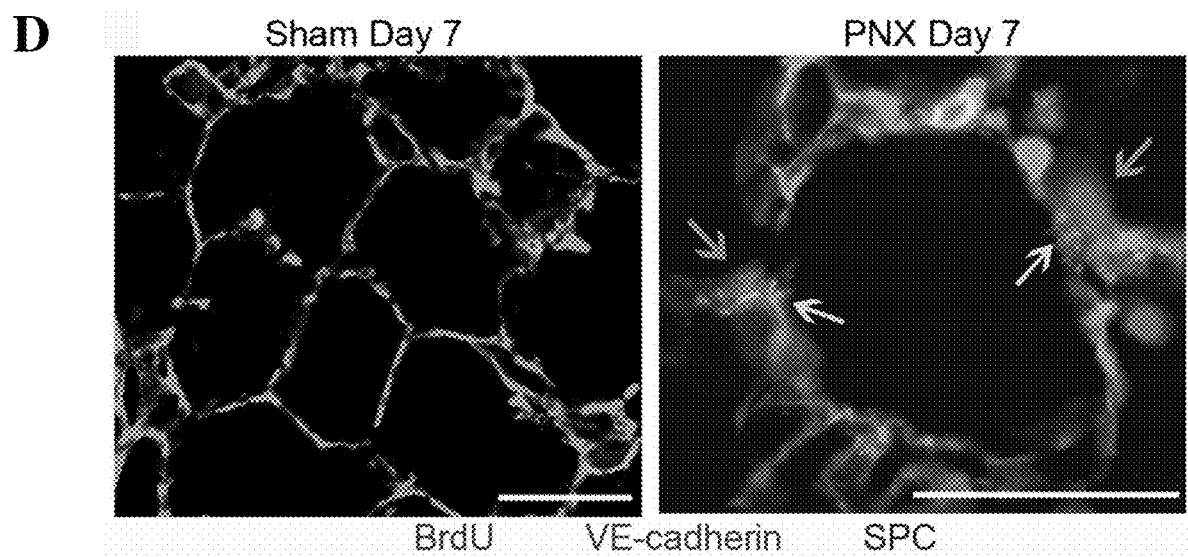
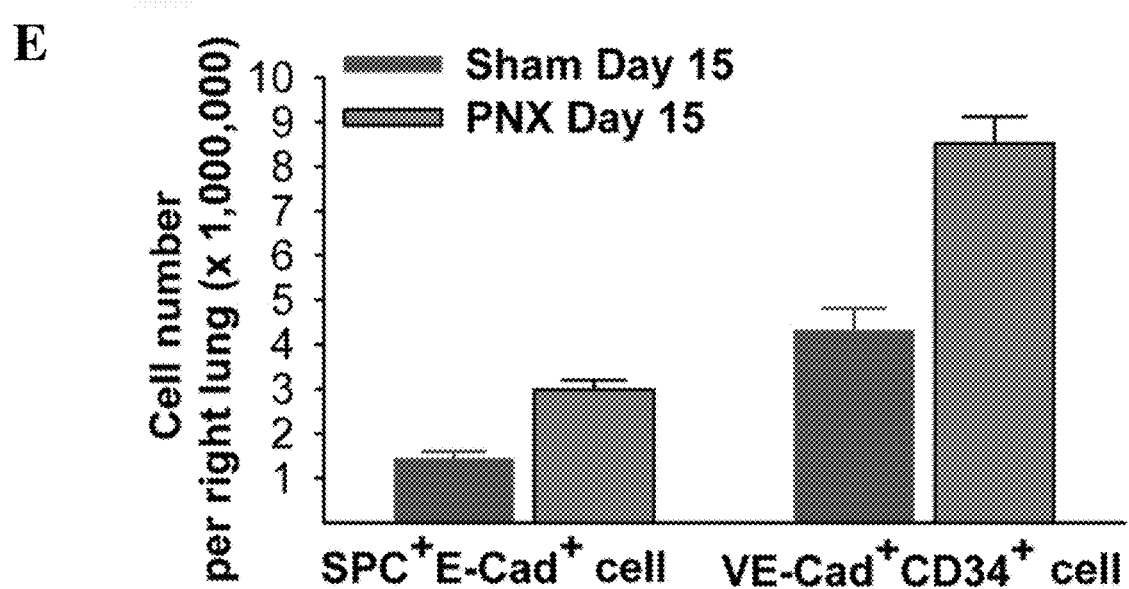

A

B

Figure 8 (con't)
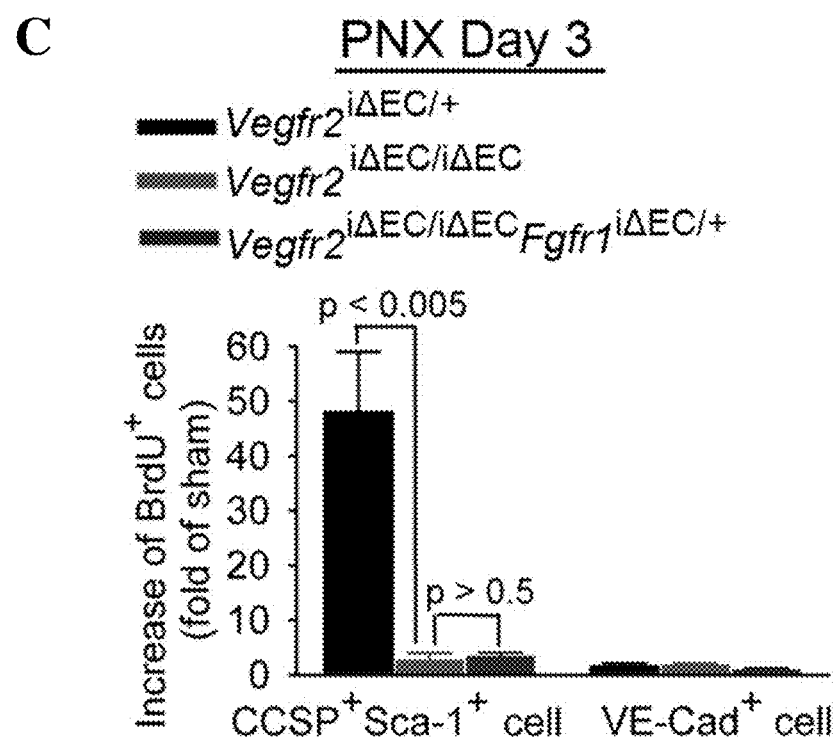

Figure 8 (con't)
D
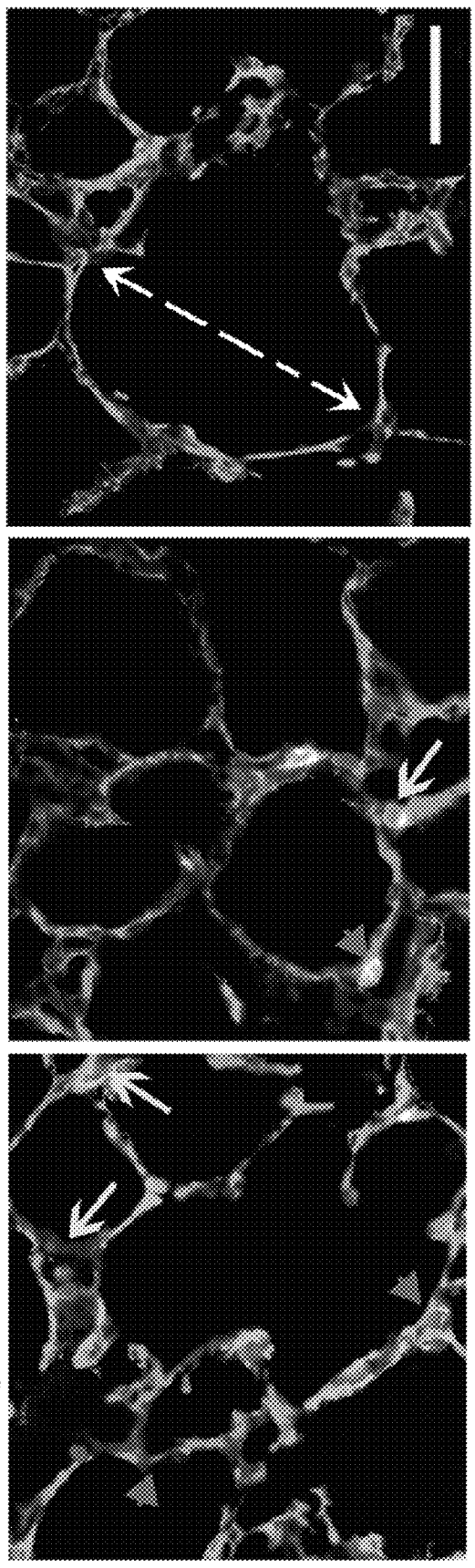

Figure 8 (con't)
E
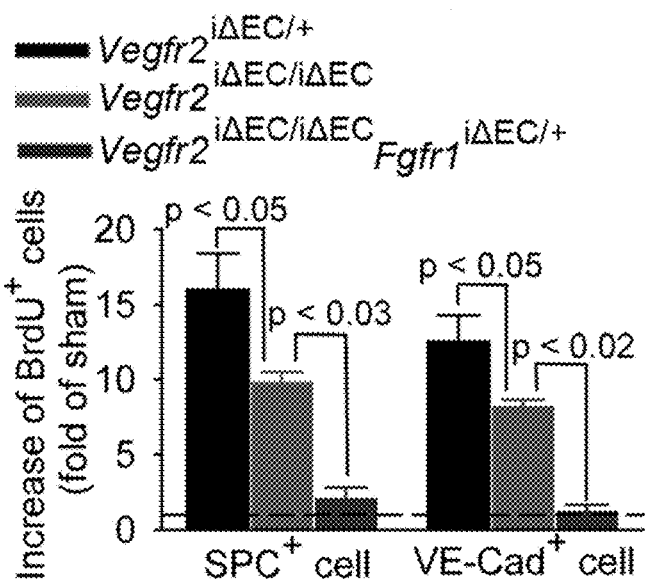
F
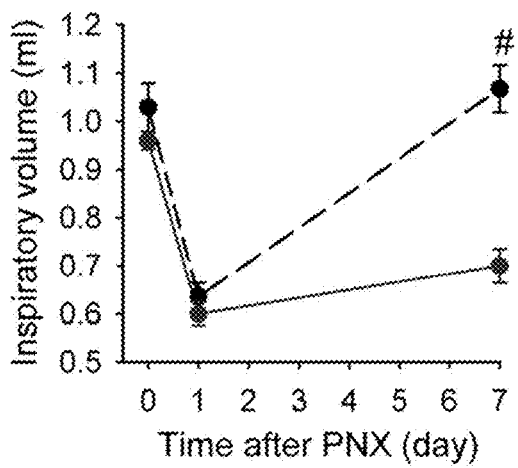
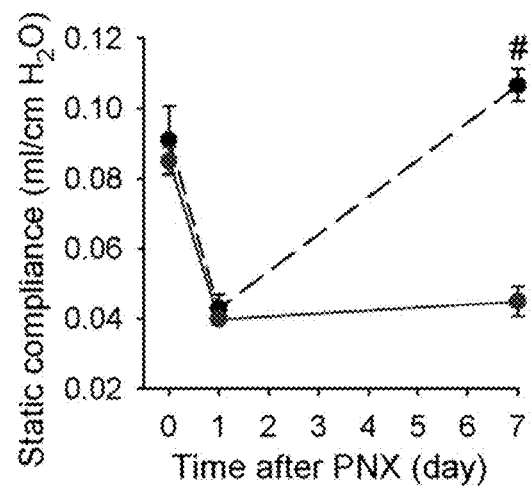

Figure 8 (con't)
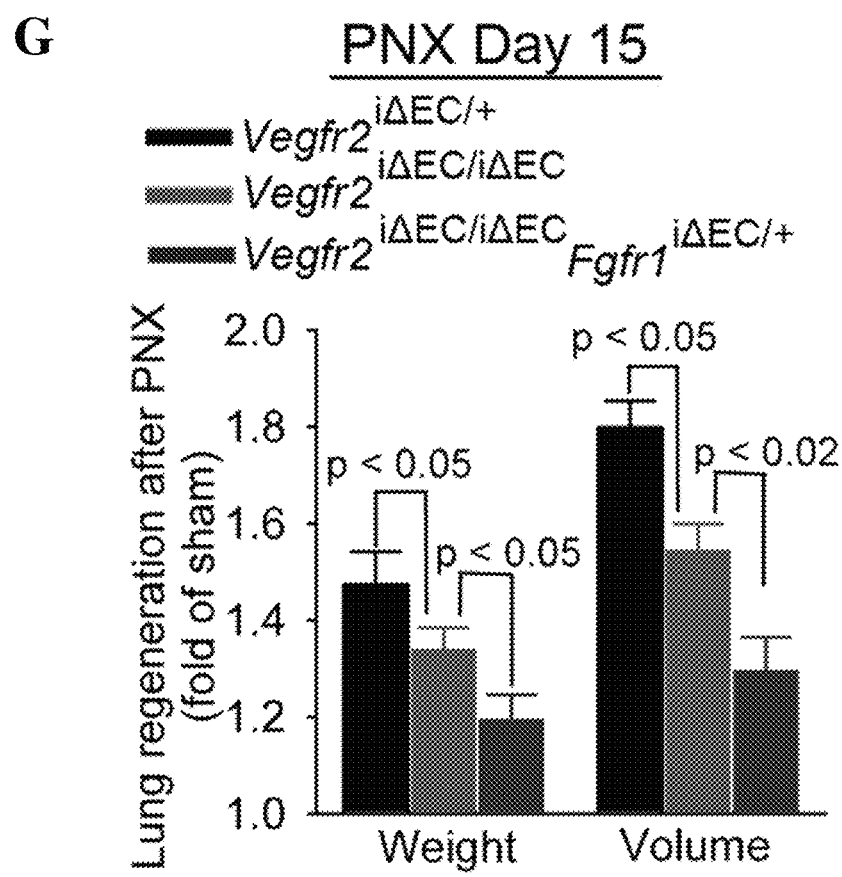

A

B

Figure 9 (con't)
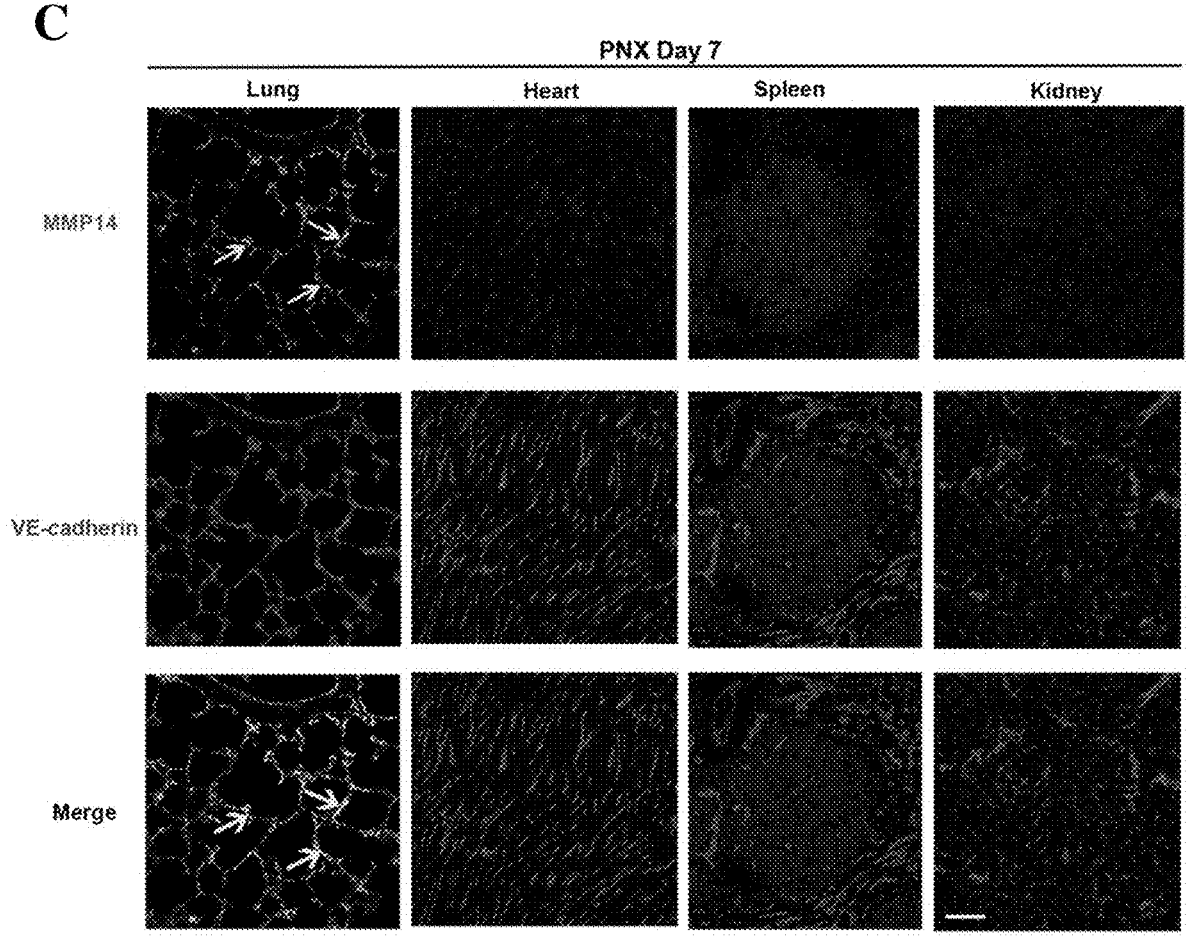

Figure 9 (con't)
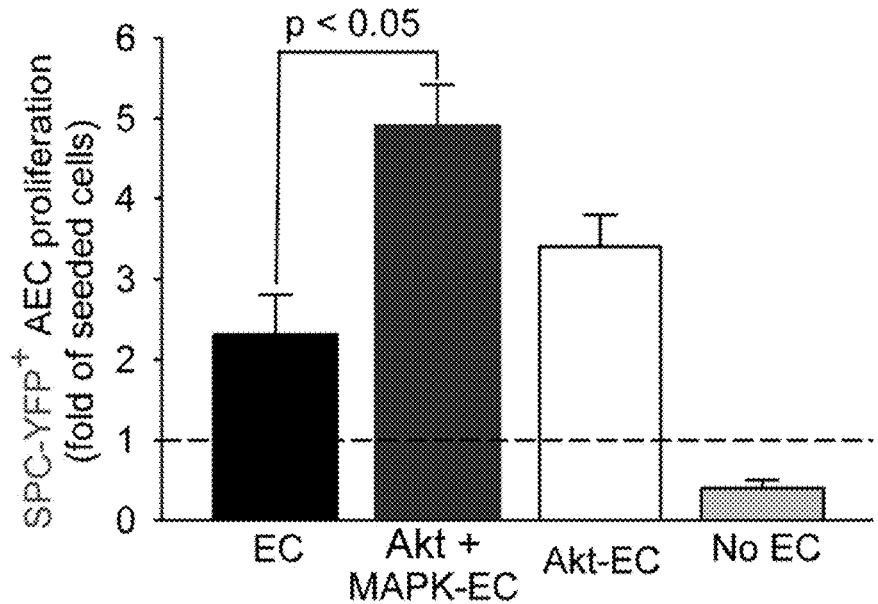
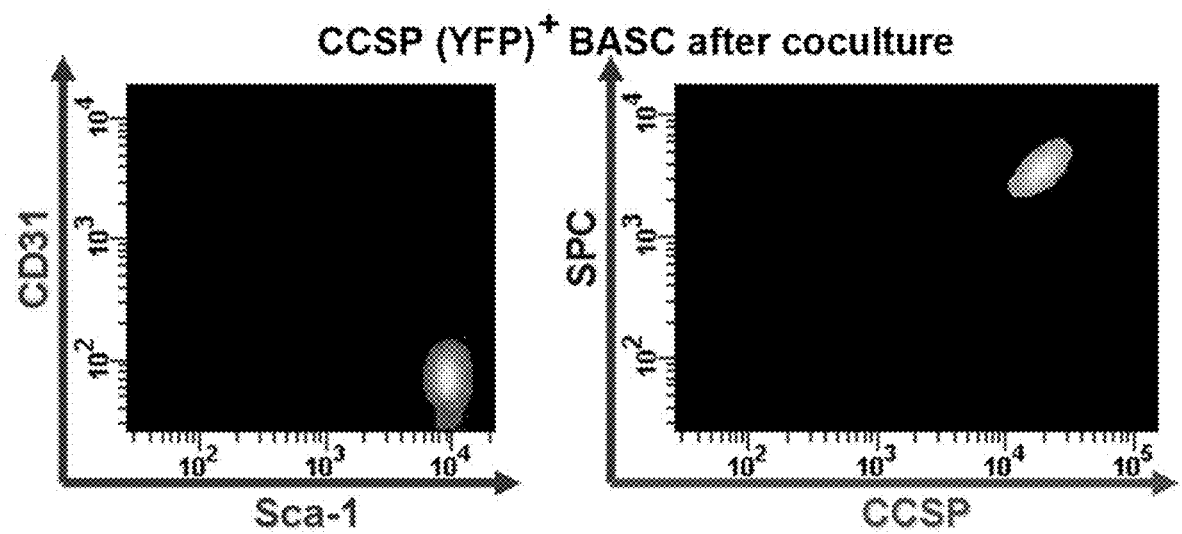

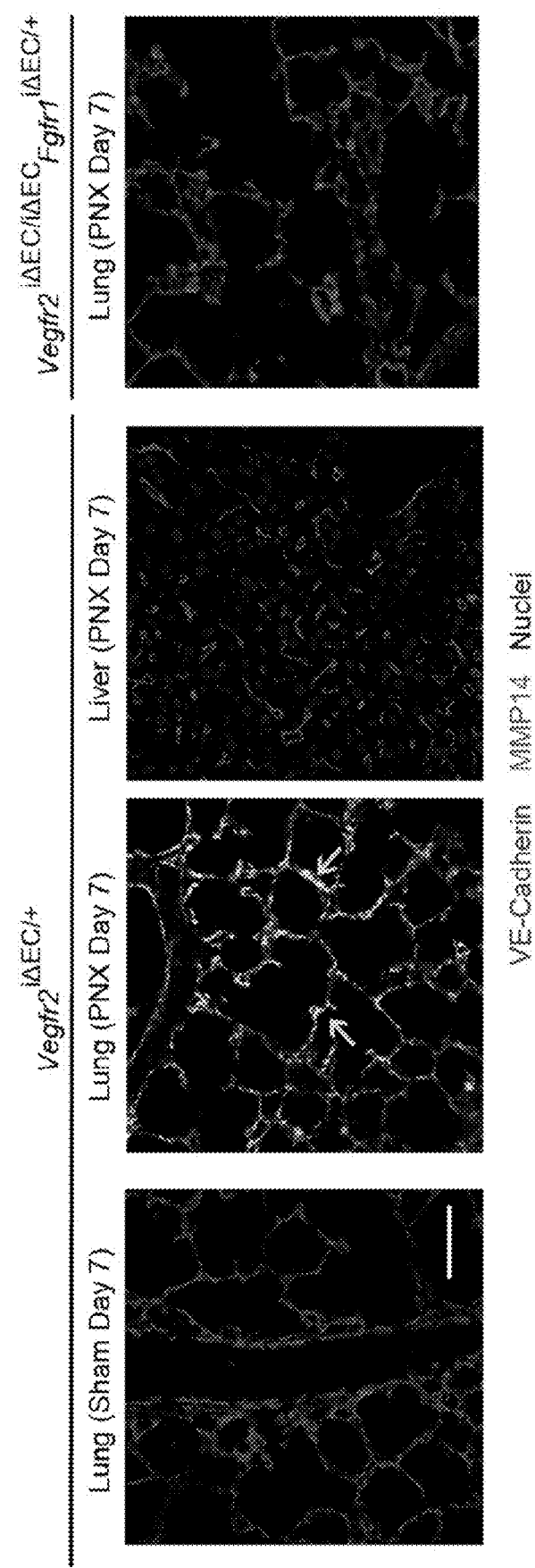
Figure 10 (con't)

Figure 10 (con't)
D
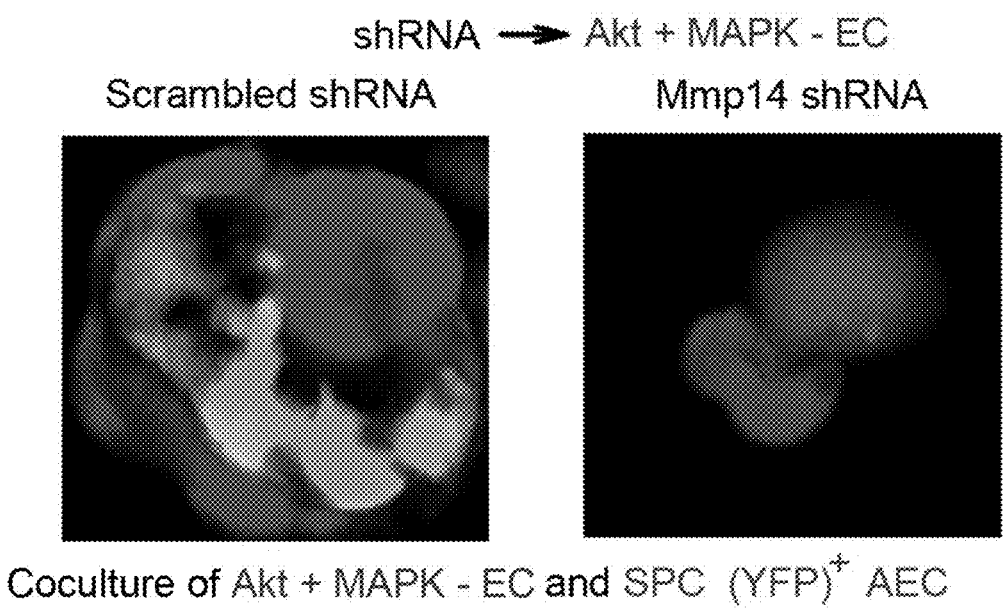
E
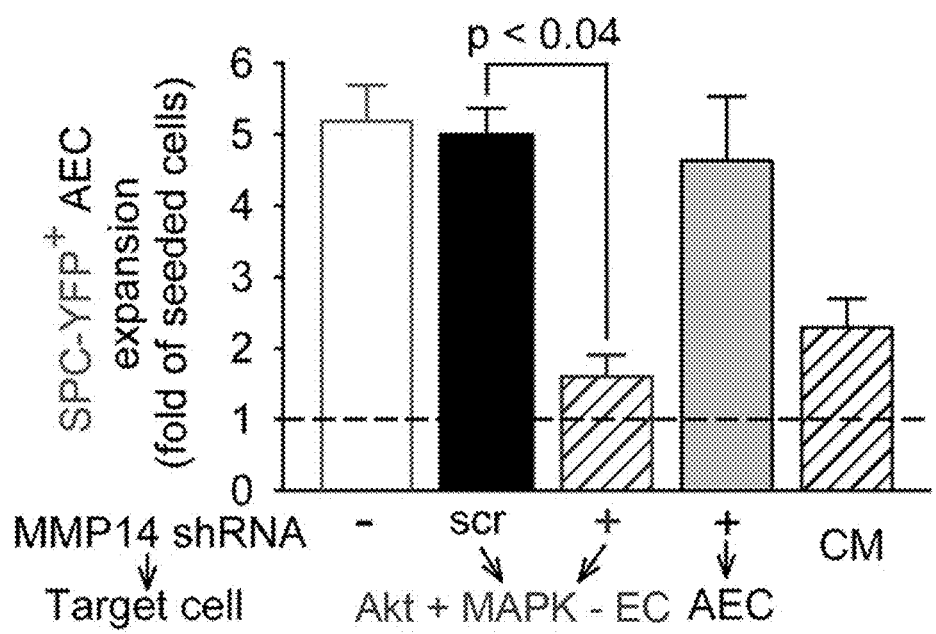

Figure 10 (con't)
F
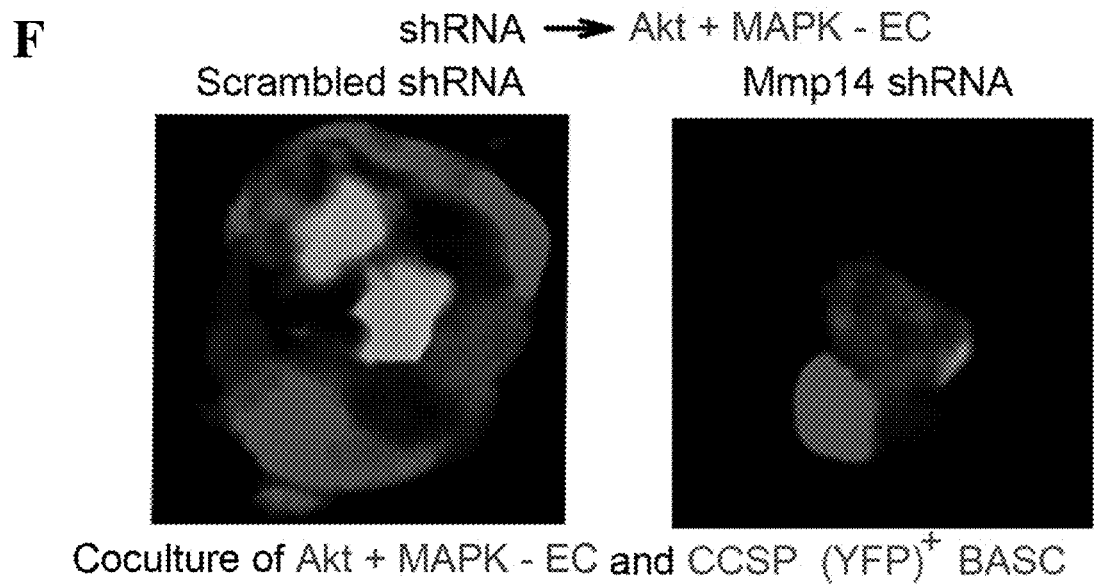
G
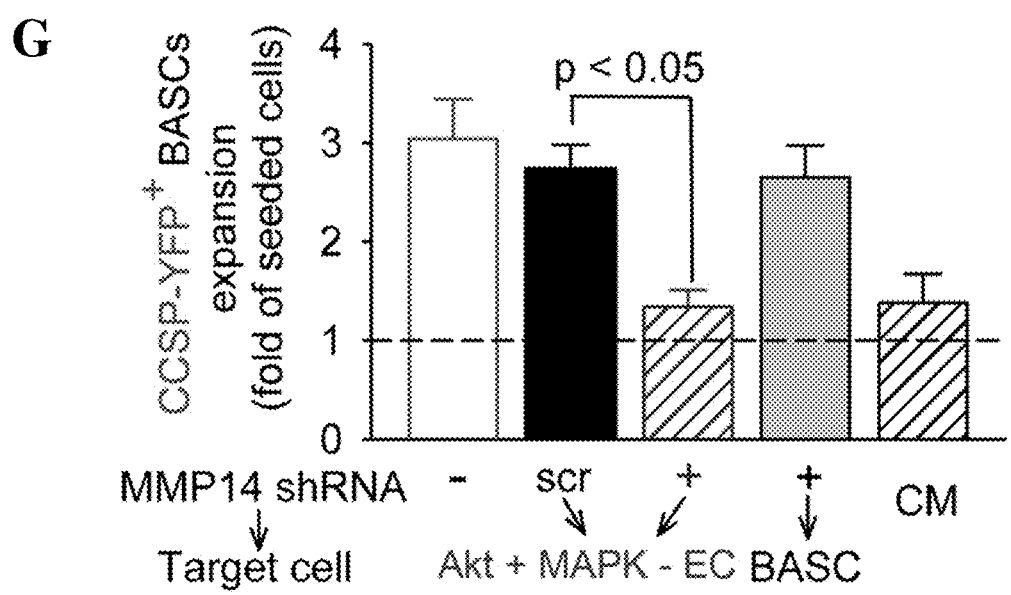

Figure 11 (con't)
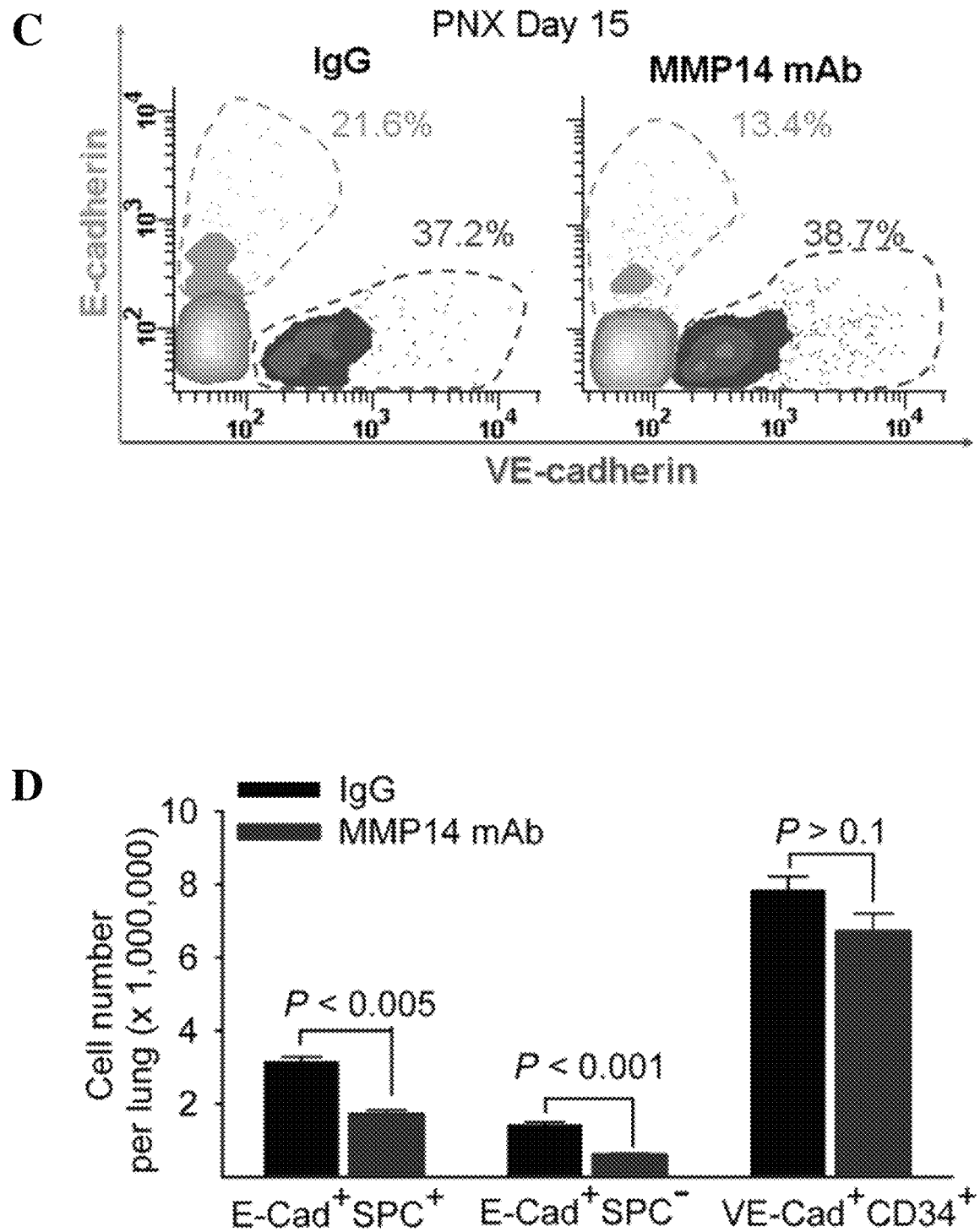

Figure 11 (con't)
E
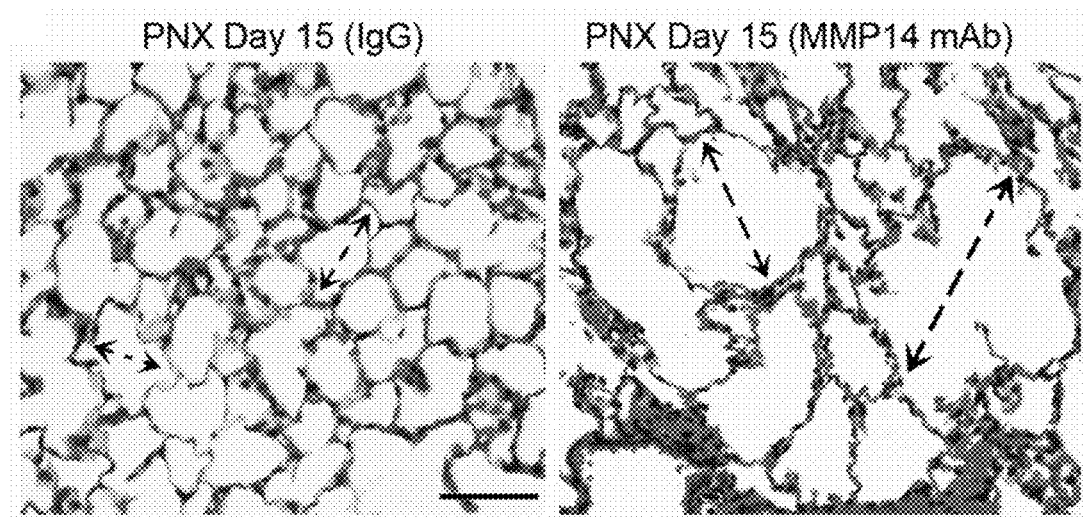
F
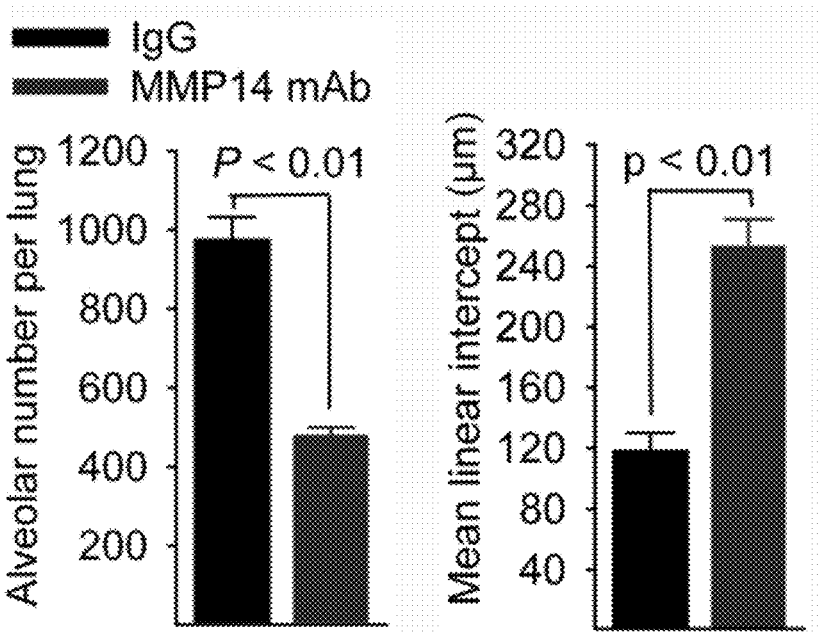

A

B

Figure 12 (con't)
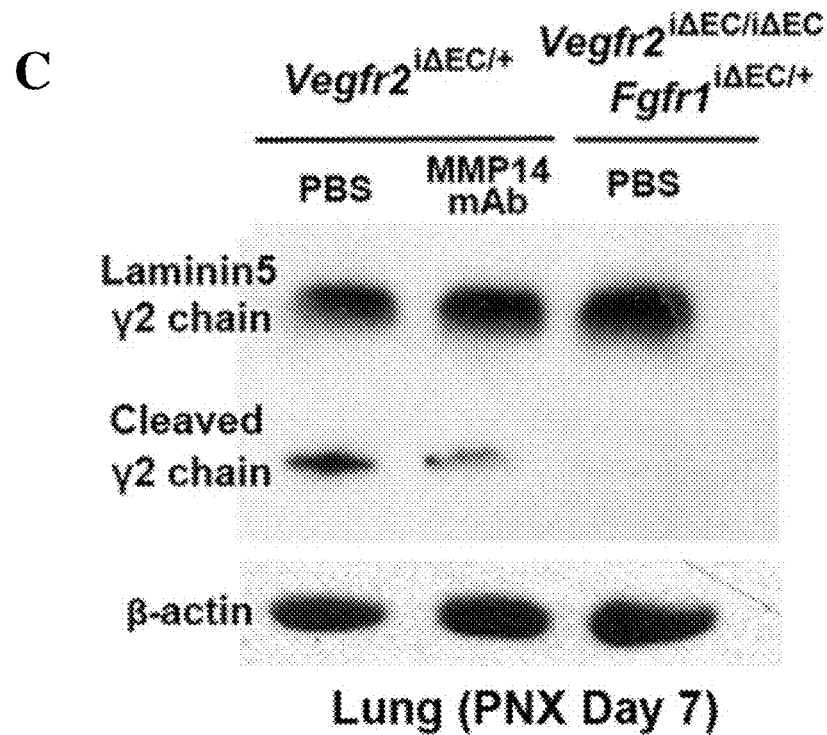
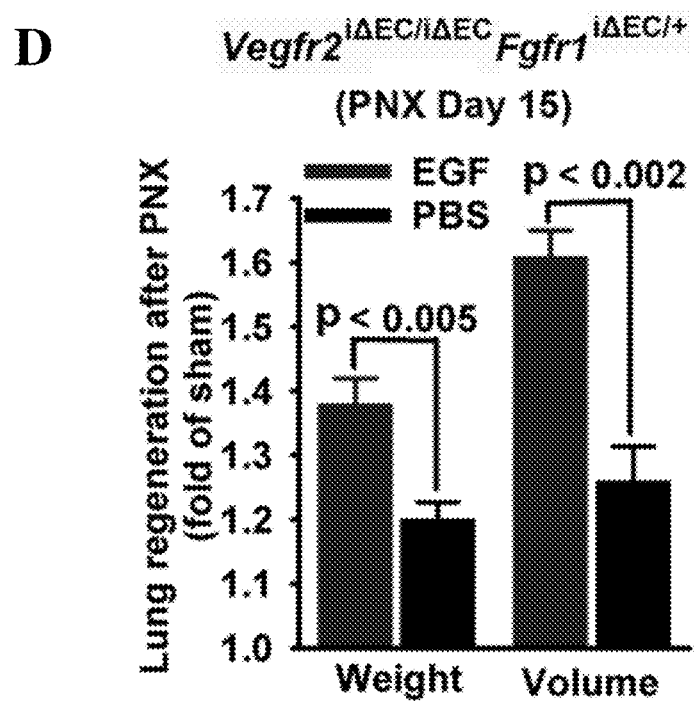

Figure 12 (con't)
E
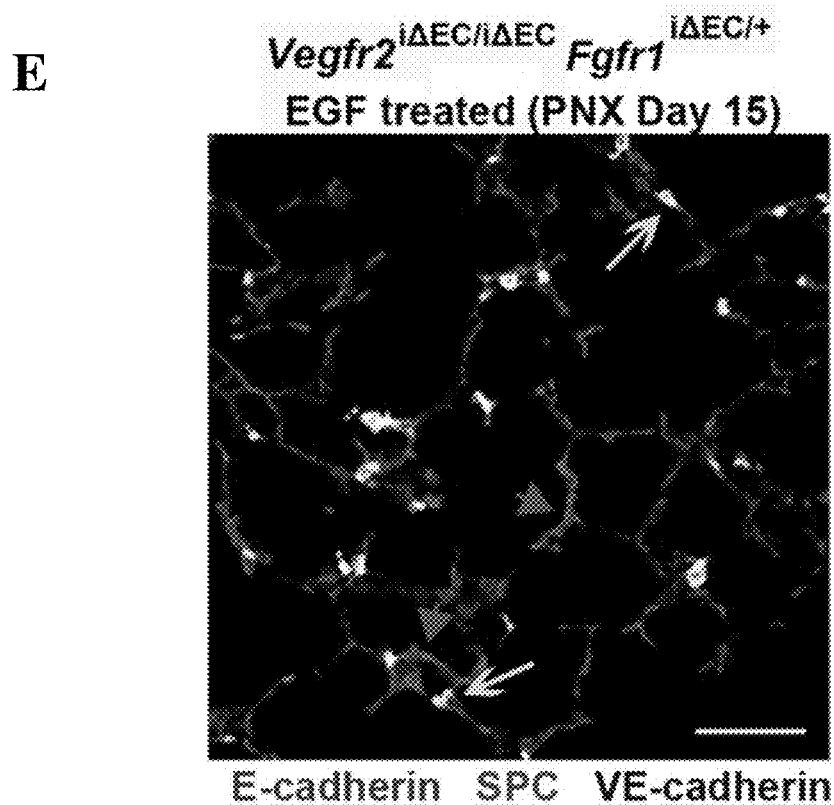
F
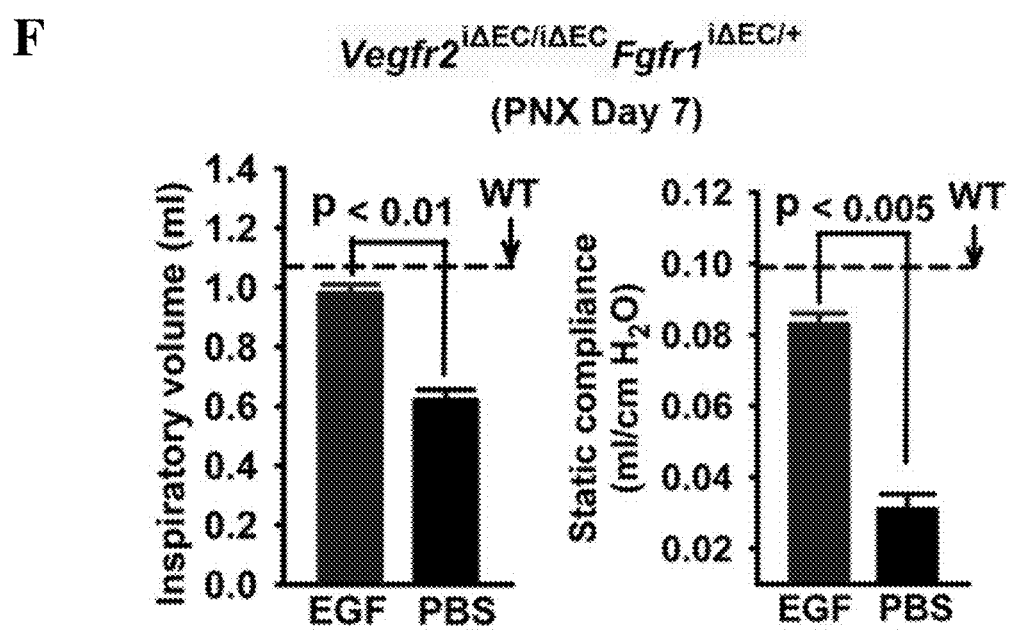

Figure 12 (con't)
G
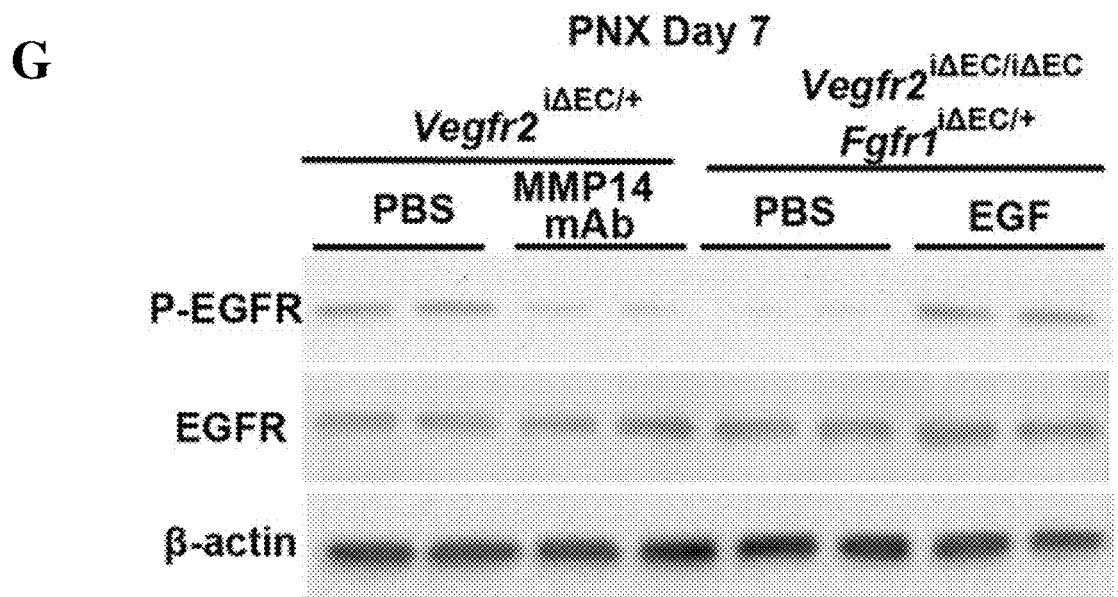
H
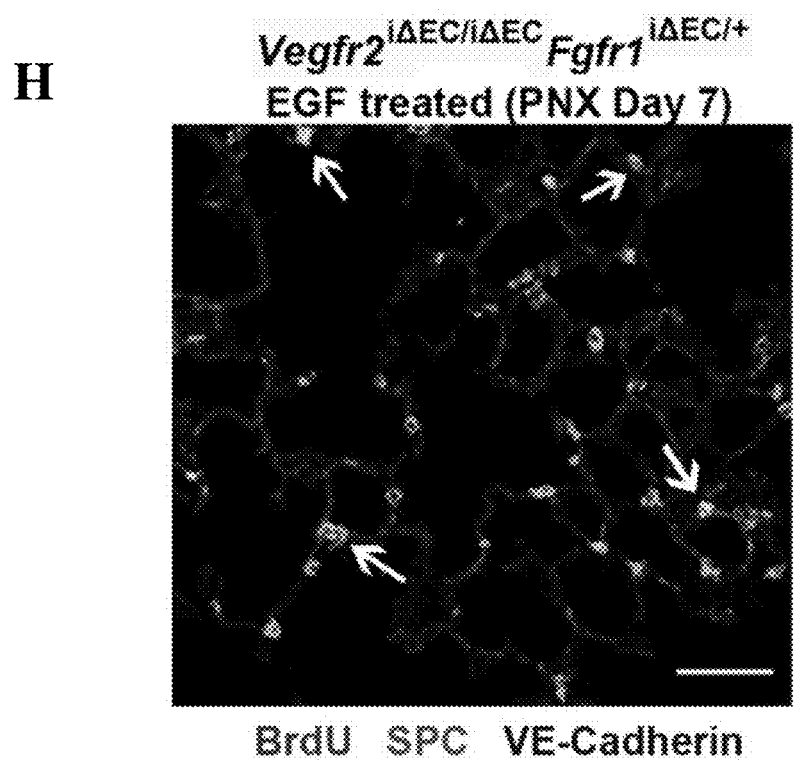

Figure 12 (con't)
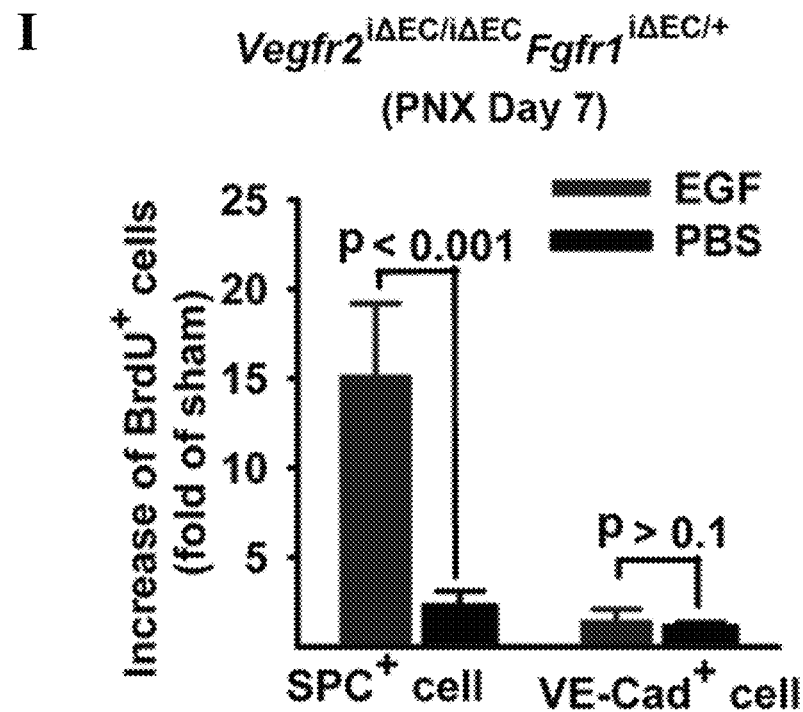
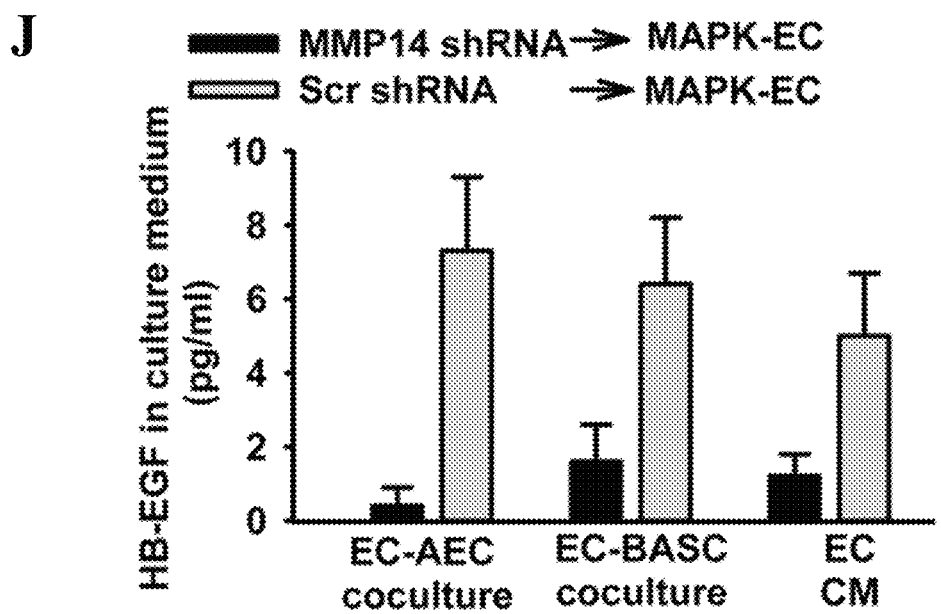

Figure 12 (con't)
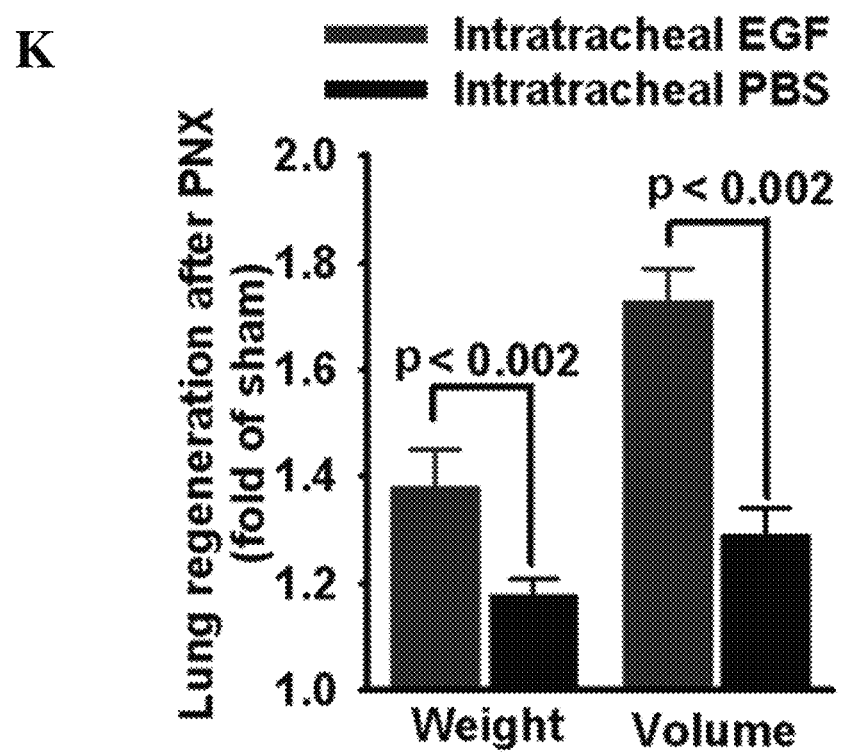

A

B

Figure 13 (con't)
C
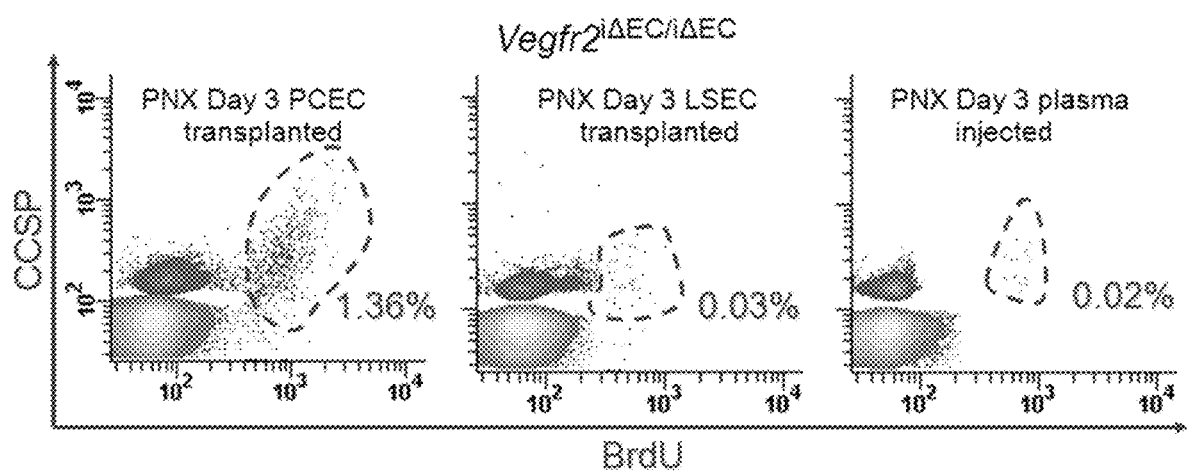
D
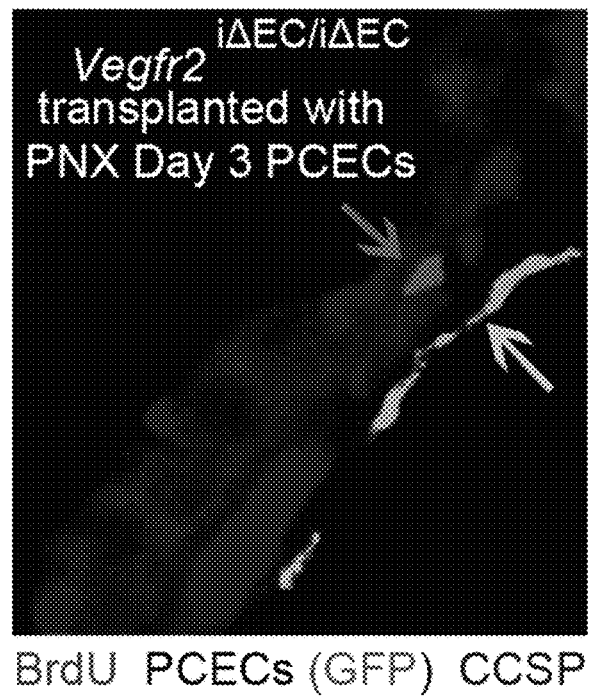

Figure 13 (con't)
E
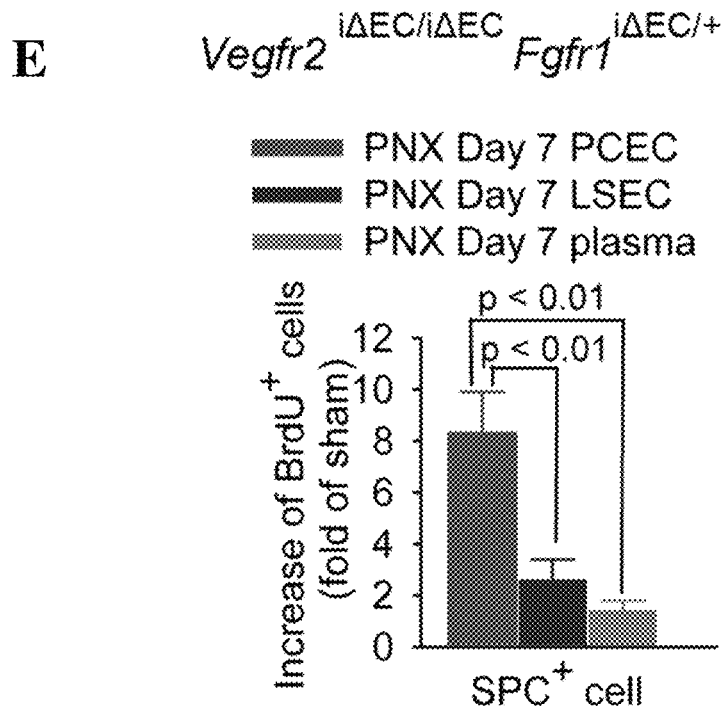
F
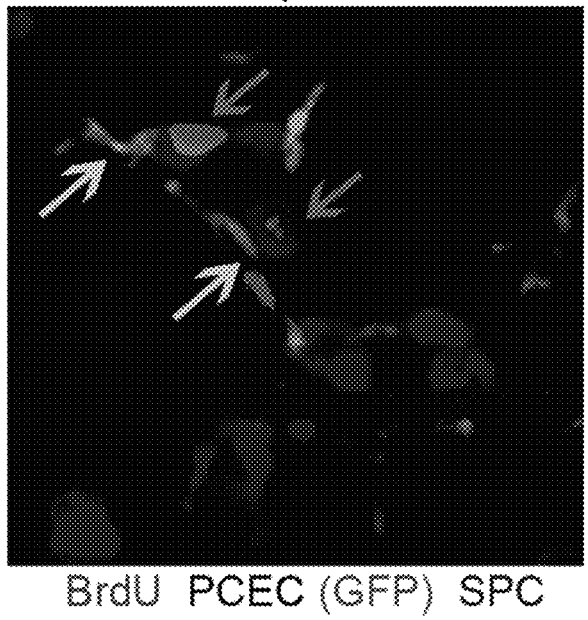

Figure 13 (con't)
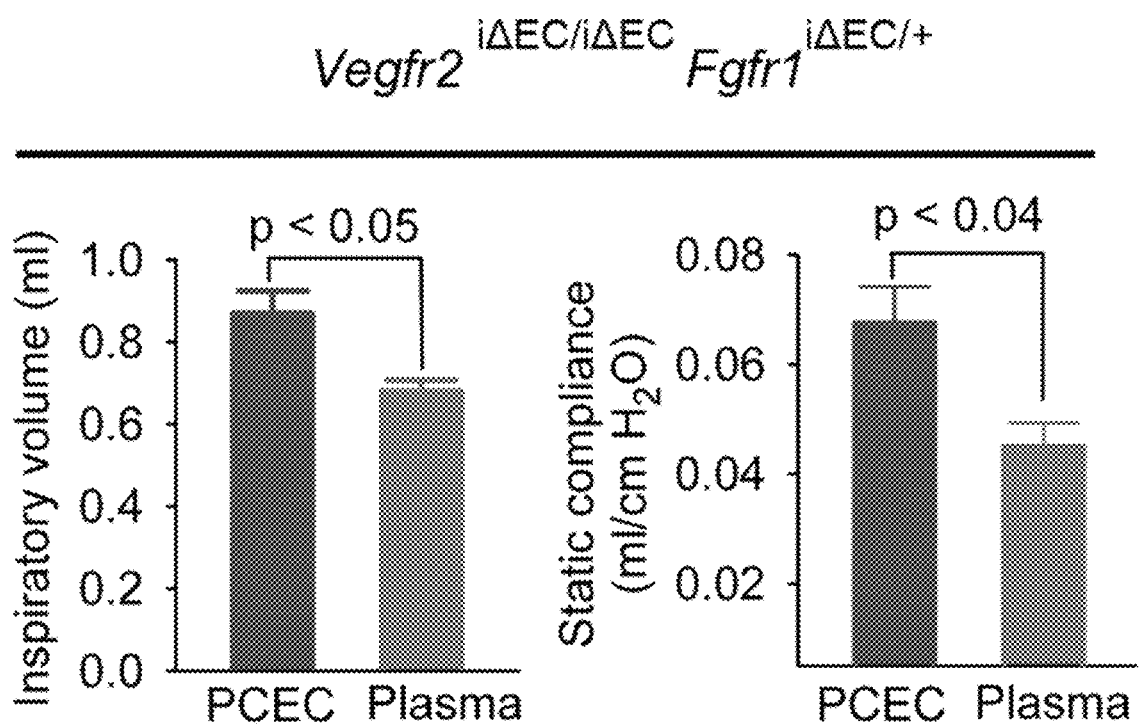

METHODS FOR ORGAN REGENERATION

CROSS-REFERENCE TO RELATED APPLICATIONS

This application claims priority to U.S. provisional application 61/411,732, filed Nov. 9, 2010, and U.S. provisional application 61/545,851, filed Oct. 11, 2011, both of which are incorporated herein in their entirety.

STATEMENT REGARDING FEDERALLY SPONSORED RESEARCH

This invention was made with Government support under Grant Number 5P50HL084936-03 awarded by the National Heart, Lung and Blood Institute. The United States Government has certain rights in the invention.

BACKGROUND

Endothelial cells (ECs) are cells that cover the interior or luminal surface of blood vessels. During embryogenesis, endothelial cells induce organogenesis before the development of circulation (Matsumoto, Science 294:559-563 (2001); Lammert, Science 294:564-567 (2001); Sakaguchi, Curr. Biol. 18:1565-1571 (2008); Makita, Nature 452:759-763 (2008)). These findings suggest that endothelial cells not only form passive conduits to deliver nutrients and oxygen, but also establish an instructive vascular niche, which through elaboration of paracrine trophogens stimulates organ regeneration, in a manner similar to endothelial-cell-derived angiocrine factors that support haematopoiesis (Butler, Cell Stem Cell 6:1-14 (2010); Hooper, Cell Stem Cell 4:263-274 (2009); Butler, J. Nature Rev. Cancer 10:138-146 (2010); Kabayashi, Nature Cell Biol. (doi: 10.1038/ncb2108) (2010)). However, the precise mechanism by which tissue-specific subsets of endothelial cells promote organogenesis in adults is unknown.

Capillary endothelial cells (ECs) form the building blocks of microvasculature of individual organs and are endowed with organ-specific phenotypic and functional attributes (Aird, Circulation research 100:158-173 (2007); Carmeliet, Nature 438:932-936 (2005); Red-Horse, Developmental cell 12:181-194 (2007); Ruoslahti, Annual review of immunology 18:813-827 (2000)). Capillary ECs deliver oxygen and nutrients, and also support organ development (Lammert et al., 2001; Matsumoto et al., 2001; Sakaguchi et al., 2008) and adult organ regeneration through elaboration of tissue-specific paracrine growth factors, also referred to as angiocrine factors (Butler, Nature reviews 10:138-146 (2010a); Butler, Cell stem cell 6:251-264 (2010b)).

Liver- and Bone Marrow-Specific Endothelial Cells.

Sinusoidal endothelial cells (SECs) compose a structurally and functionally unique capillary network that vascularizes specific organs, including bone marrow and liver. In adult mice, bone marrow SECs, through expression of specific angiocrine trophogens, such as Notch ligands, support haematopoietic regeneration (Butler, Cell Stem Cell 6:1-14 (2010); Hooper, Cell Stem Cell 4:263-274 (2009); Butler, JNature Rev. Cancer 10:138-146 (2010); Kabayashi, Nature Cell Biol. (doi: 10.1038/ncb2108) (2010)). Similarly, the hepatic circulation is predominantly lined by liver SECs (Lee, Hepatology 45:817-825 (2007); Klein, Hepatology 47:1018-1031 (2008)) (LSECs), with each hepatocyte residing in cellular proximity to LSECs. Liver regeneration requires proliferation of hepatocytes. However, the lack of phenotypic and operational definition of liver endothelial cells, and paucity of relevant mouse angiogenic genetic models (Greene, Ann. Surg. 237:530-535 (2003); Van Buren, J. Clin. Oncol. 26:1836-1842 (2008); LeCouter, Science 299:890-893 (2003)) have handicapped studies of the role of LSECs in regulation of hepatic regeneration Zaret, Science 322:1490-1494 (2008); Fausto, Hepatology 43:S45S53 (2006); Michalopoulos, Science 276:60-66 (1997); Greenbaum, J. Clin. Invest. 102:996-1007 (1998); Huh, Proc. Natl. Acad. Sci. USA 101:4477-4482 (2004)).

SECs within bone marrow (BM) comprise phenotypically and functionally discreet populations of ECs. After chemotherapy and irradiation, activated BM SECs reconstitute hematopoietic by angiocrine expression of Notch ligands and IGFBPs (Butler, Cell stem cell 6:251-264 (2010b); Kobayashi, Nature cell biology 12:1046-1056 (2010)). Conditional deletion of VEGF-A receptor-2 (VEGFR2) in BM SECs (Hooper, Cell stem cell 4: 263-274 (2009)) of adult mice inhibits BM regeneration by impairing the production of angiocrine factors.

Lung-Specific Endothelial Cells.

During lung development, the vascular plexus (capillary) develops in parallel with the alveolus (Cardoso, Annual review of physiology 63:471-494 (2001); Metzger, Nature 453:745-750 (2008); White, Development 134:3743-3752 (2007)). As a unique organ that facilitates gas exchange, the lung alveolus is highly vascularized, with pulmonary capillary endothelial cells (PCECs) lining all alveoli and residing in close proximity to epithelial cells (Bhattacharya, Chest 128:553 S-555S. (2005); Komarova, Annual review of physiology 72:463-493 (2010); Muzykantov, Expert opinion on drug delivery 2:909-926 (2005); Petrache, Nature medicine 11:491-498 (2005); Voelkel, Am J Physiol Lung Cell Mol Physiol 290:L209-221 (2006)). Lung development and regeneration is driven by alveologenesis, a process dependent on proliferation of epithelial progenitor cells (Kotton, Cell and tissue research 331:145-156 (2008); Rock, Annual review of cell and developmental biology (2011); Stripp, Proceedings of the American Thoracic Society 5:328-333 (2008)), which comprise subsets of alveolar epithelial cells (AECs) (Chapman, The Journal of clinical investigation 121:2855-2862 (2011); Liu, The Journal of experimental medicine 208:1473-1484 (2011)) and bronchioalveolar stem cells (BASCs) (Kim, Cell 121:823-835 (2005); Zhang, Nature genetics 40:862-870 (2008)).

The formation of the alveolar-capillary interface is pivotal for pulmonary gas exchange function (Giordano, The Journal of biological chemistry 283:29447-29460 (2008); Huh, Science 328:1662-1668 (2010); Petersen, Science (New York, N.Y. 329:538-541 (2010); Vaporciyan, Science (New York, N.Y. 262:1580-1582 (1993)). Although PCECs are a specialized capillary vasculature involved in guiding alveolarization (DeLisser, The Journal of biological chemistry 281:8724-8731 (2006); Leuwerke, Am J Physiol Lung Cell Mol Physiol 282:L1272-1278 (2002)) and regenerative alveolar remodeling (Metzger, Nature 453:745-750 (2008)), the precise mechanisms by which PCECs modulate alveolar development are unknown.

In addition to their capacity to undergo proliferative sprouting angiogenesis to vascularize alveoli (Alvarez, Am J Physiol Lung Cell Mol Physiol 294:L419-430. (2008); Del Moral, Developmental biology 290:177-188 (2006); Shu, Development 129:4831-4842 (2002)), PCECs specify the differentiation of endoderm and mesoderm progenitors into primitive lung epithelial and vascular progenitor cells by producing paracrine factors (Bhattacharya, Chest 128:553 S-555S. (2005); Yamamoto, Developmental biology 308:44-53 (2007)). These findings suggest that PCECs may promote alveologenesis by elaborating angiocrine growth signals. Whether PCEC-derived instructive signals can trigger regenerative alveolarization in the adult lungs has however not been studied. Indeed, the paucity of mouse lung regenerative genetic models and lack of operational definition of PCECs have handicapped studies of PCECs in guiding alveolar regeneration in adult lungs.

Surgical removal of the left lung, known as left unilateral pneumonectomy (PNX), induces the expansion of mass and volume in the intact lobes of the remaining right lung by alveogenesis (Cowan, The American review of respiratory disease 111:267-277 (1975); Leuwerke, Am J Physiol Lung Cell Mol Physiol 282:L1272-1278 (2002); Nolen-Walston, Am J Physiol Lung Cell Mol Physiol 294:L1158-1165 (2008)). However, the precise mechanism(s) by which PNX initiates and sustains regenerative alveologenesis in the undamaged lung is unknown. Defining the cellular and molecular mechanisms that modulate lung regeneration is essential to develop strategies to treat respiratory disorders.

SUMMARY

The disclosure of this invention provides methods of enhancing or inducing regeneration of an organ in a subject in need thereof. In one embodiment is provided a method of enhancing or initiating regeneration of an organ in a subject in need thereof comprising the administration of endothelial cells specific to said organ, or inductive endothelial cells specific to said organ, into the area of the body in which organ regeneration is desired in said subject.

Another embodiment provides a method of enhancing or initiating liver regeneration in a subject in need thereof comprising the intrahepatic transplantation of liver sinusoidal endothelial cells (LSECs), or inductive LSECs. This embodiment can further comprise administration of VEGF-A or hepatocytes. In a further embodiment, the LSECs or inductive LSECs are VEGFR2$^+$VE-cadherin$^+$VEGFR3$^+$CD34$^-$ factor VIII$^+$ LSECs.

Still another embodiment provides a method of enhancing or initiating lung regeneration in a subject in need thereof comprising intravenous or intratracheal transplantation of pulmonary capillary endothelial cells (PCECs), or inductive PCECs. This embodiment can further comprise administration of epithelial progenitor cells, MMP14, VEGF-A, and/or FGF. In a further embodiment, said PCECs or inductive PCECs express MMP14.

Yet another embodiment provides a method of expanding hepatocytes in culture by co-culturing said hepatocytes with liver sinusoidal endothelial cells. A further embodiment provides a method of expanding lung epithelial progenitor cells in culture by co-culturing said lung epithelial progenitor cells with pulmonary capillary endothelial cells.

An additional embodiment provides a method to enhance or induce organ regeneration in a subject in need thereof comprising administering one or more of VEGF-A, VEGF-E, FGF-2, MMP14, EGF, or other EGF-receptor ligands, to said subject in an amount sufficient to enhance or induce organ regeneration in said subject. In further embodiments, the organ is the liver or the lung.

In another embodiment is provided a composition useful for administration to a subject in need of organ regeneration, comprising isolated endothelial cells specific to said organ, or isolated inductive endothelial cells specific to said organ, optionally in combination with a pharmaceutically-acceptable carrier. In a further embodiment, said endothelial cells or inductive endothelial cells are autologous cells. In another embodiment, the composition additionally comprises one or more of VEGF-A, VEGF-E, FGF-2, EGF, or MMP14.

In another embodiment is provided a composition useful for administration to a subject in need of liver regeneration, comprising VEGFR2$^+$VE-cadherin$^+$VEGFR3$^+$CD34$^-$ factor VIII$^+$ LSECs. In another embodiment is provided a composition useful for administration to a subject in need of lung regeneration, comprising VEGFR2$^+$VE-cadherin$^+$CD34$^+$CD31$^+$FGFR1$^+$ PCECs.

A further embodiment provides a method of isolating liver-specific endothelial cells comprising isolating cells that are VEGFR2$^+$VE-cadherin$^+$VEGFR3$^+$CD34$^-$ factor VIII$^+$ cells. Another embodiment provides a method of isolating lung-specific endothelial cells comprising isolating cells that are VEGFR2$^+$VE-cadherin$^+$CD34$^+$CD31$^+$FGFR1$^+$ cells.

Figure 3:
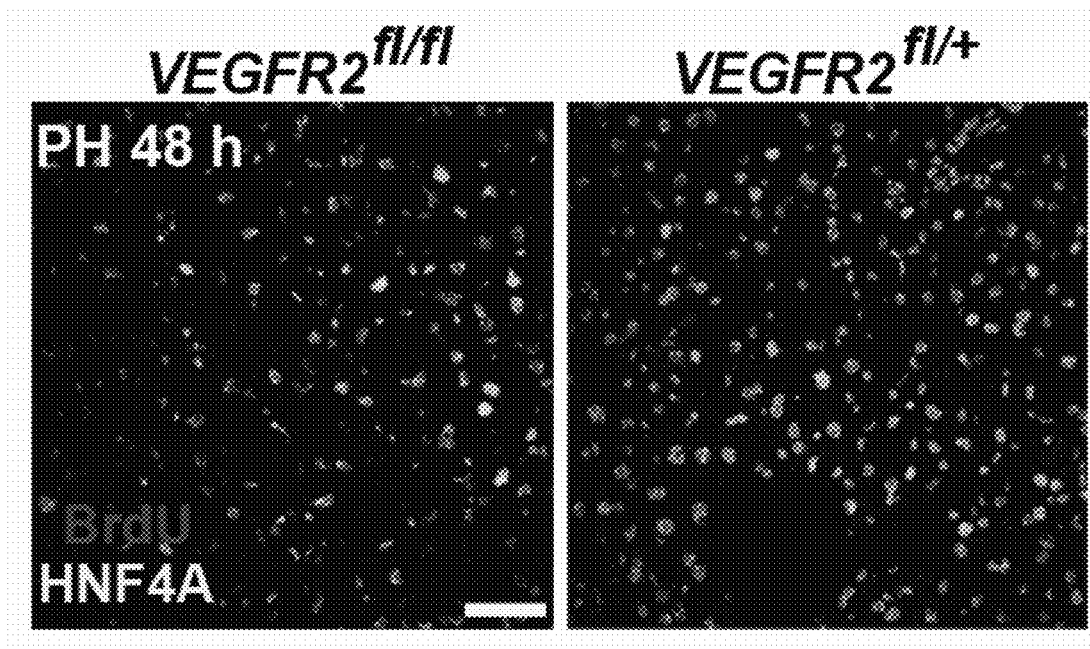
FIG. 3A-K. VEGFR2-Id1 activation in LSECs mediates liver regeneration induced by partial hepatectomy. A, B, Hepatocyte proliferation after partial hepatectomy is impaired in VEGFR2$^{fl/fl}$ mice (n=5). C-E, Inhibition of liver mass regeneration (C) and functional VE-cadherin$^+$isolectin$^+$ vessel formation (D,E) in VEGFR2$^{fl/fl}$ mice after partial hepatectomy (n=4-6). F, G, Injection of VEGF-A$_{164}$, but not VEGFR1-specific ligand PlGF, accelerates the regeneration of liver mass (F), associated with an incremental increase in VEGFR3$^+$CD34$^-$ LSEC number (G) (n=4). H, Regenerative liver section of Id1$^{VenusYFP}$ mouse (Nam, Cell Stem Cell 5:515-526 (2009)). Id1 is selectively upregulated by partial hepatectomy in VE-cadherin$^+$ vessels. I, VEGFR2 deletion diminishes Id1 upregulation in the regenerative liver (n=5). P<0.05; **P<0.01, versus VEGFR2N$^{fl/+}$ (B-E, I), versus PlGF-treated group (F). Scale bar, 50 µm. Error bars, s.e.m. J, Selective knockdown of VEGFR2 in liver endothelial cells after tamoxifen treatment of Rosa$^-$ CreER$^{T2}$VEGFR$^{flox/flox}$ mice, N=4. K, Quantification of endothelial-specific VEGFR$^2$ knockdown in VE-cadherin$^-$CreER$^{T2}$VEGFR2$^{flox/flox}$ mice.
Figure 3:
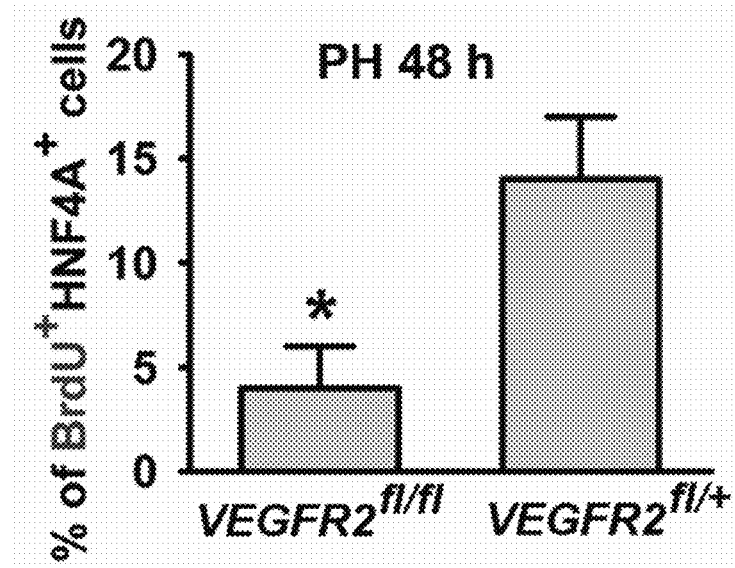
Figure 4:
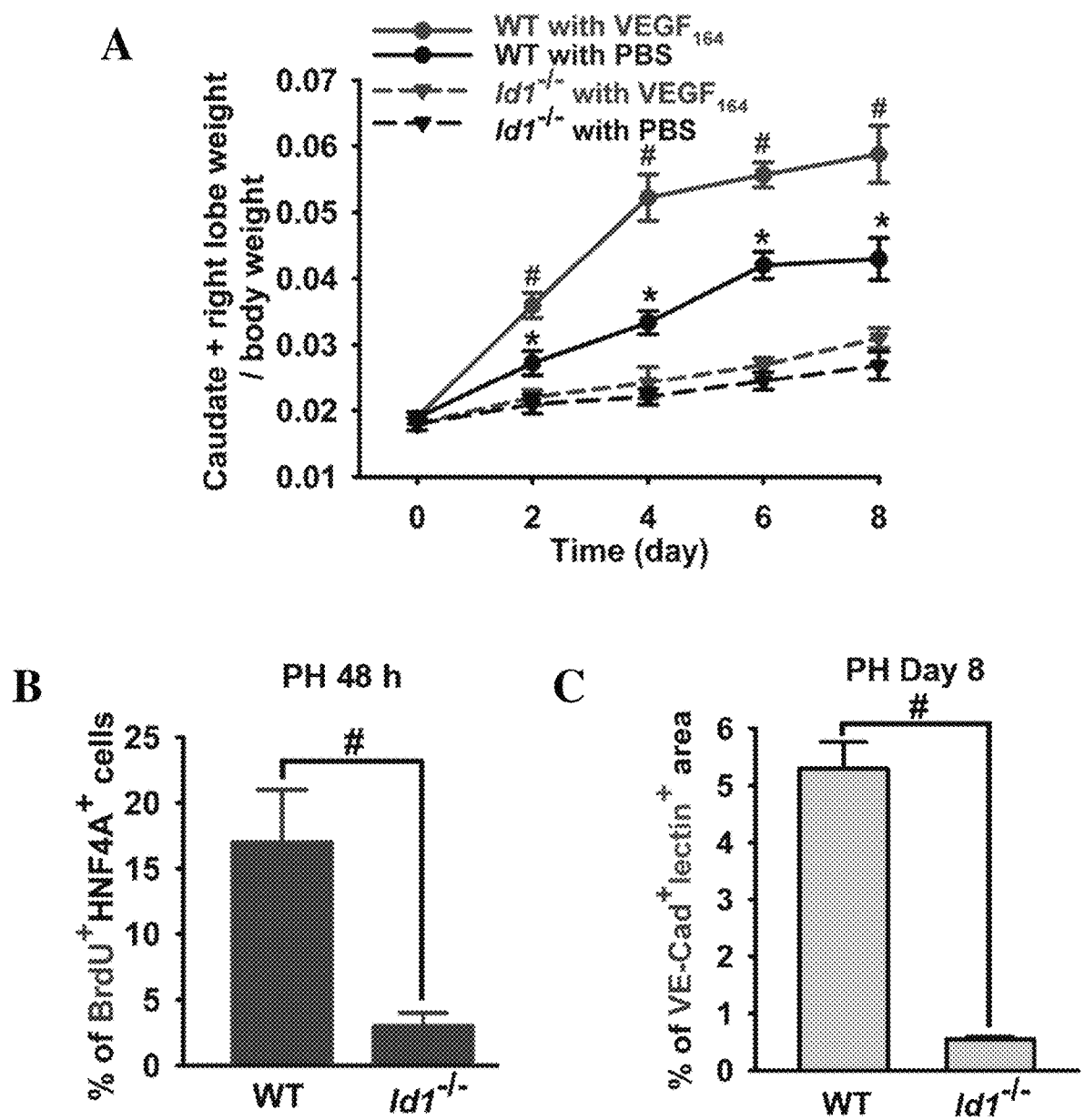
FIG. 4A-K. Id1 upregulation in LSECs is essential for liver regeneration. A, Compared with their wild-type (WT) littermates, Id1$^{-/-}$ mice manifest impaired regeneration in liver mass, which fails to be rescued by VEGF-A$_{164}$ administration (n=5). B, C, Impaired hepatocyte proliferation (B) and assembly of VE-cadherin$^+$isolectin$^+$ vessels (C) in the Id1$^{-/-}$ mice after partial hepatectomy (n=5). D, E, The LSEC-dependent stimulation of hepatocyte proliferation was specifically inhibited by Id1 gene knockdown. Scr, scrambled. CM, LSEC-conditioned medium (n=4). F, Intrasplenic transplantation of GFP-marked LSECs incorporated into the lumen of VEGFR3$^+$sinusoidal vasculature in the Id1$^{-/-}$ liver (Follenzi, J. Clin. Invest:118, 935-945 (2008)). G, H, Transplantation of Id1$^{-/-}$ LSECs restores the regeneration of mass (G) and hepatocyte proliferation (H) in the Id1$^{-/-}$ liver (n=4). Dashed line, level of Id1$^{-/-}$ liver without endothelial cell transplantation. I, Cellular proximity is essential in the stimulation of hepatocyte mitosis by the transplanted GFP$^+$Id1$^{+/+}$ vasculature. *P<0.05, versus Id1$^{-/-}$ (a); **P<0.01, versus Id1$^{-/-}$ with VEGF$_{164}$ (A), versus WT (B, C). Scale bars, 50 μm (D, F) and 20 μm (H). Error bars, s.e.m. J, Sustained inhibition of liver mass recovery in Id1$^{-/-}$ mice. Throughout the indicated period, VEGF-A$_{164}$ injection failed to rescue the hepatic reconstitution. *P<0.05 vs WT, N=4. K, Impaired regeneration of liver function (increased plasma bilirubin level) in Id1$^{-/-}$ mice after PH. #, P<0.01, vs. WT, N=3.

in the lungs, but not other vascularized organs after PNX. Although there was no significant difference in VEGFR2 protein level in different organs, VEGFR2 activation only occurred in the lungs after PNX at day 7. This finding demonstrates a lung-specific activation of VEGFR2 after PNX. The kinetics of VEGFR2 activation in the lungs after PNX is shown in FIG. 3A. C, MMP14 was specifically upregulated in the lung vasculature but not in the vascular beds of heart, spleen, or kidney after PNX. The expression and localization of MMP14 (arrow) was examined in different organs of the mice after PNX. Expression of MMP14 in the lung and liver after PNX is shown in FIG. 4C. D, MAPKinase and Akt-activated endothelial cells (MAPK+ Akt ECs) manifested the most significant expansion of SPC$^+$ AECIIs. Coculture of ECs with AECs was described in "methods". n=5. E, CCSP$^+$ BASCs maintained their phenotypic markers after coculture. CCSP (YFP)$^+$ cells were analyzed by flow cytometry after coculture with ECs. After coculture, BASCs retain the phenotypic signature as CCSP$^+$ Sca-1$^+$CD31$^-$ cells.

FIG. 10A-G. After PNX, MMP14 is specifically produced by PCECs and induces formation of alveolar-capillary-like sac in 3D angiosphere coculture with inductive ECs. A, PNX induces time-dependent upregulation of MMP14 protein in the remaining right lobes. Representative Western blot image is shown. B, C, After PNX, specific upregulation of MMP14 in VE-cadherin$^+$ PCECs is attenuated in Vegfr2$^{i\Delta EC/i\Delta EC}$Fgfr1$^{i\Delta EC/+}$ mice, as shown by flow cytometry (B) and immunostaining (C). Note the colocalization of upregulated MMP14 in VE-cadherin$^+$ PCECs (arrow), but not liver ECs of pneumonectomized control mice. Scale bar, 100 μm. D, E, 3D coculture of SPC(YFP)$^+$ AECIIs with MAPK and Akt activated primary ECs (MAPK+Akt ECs) forms angiosphere and establishes a bioreactor for expansion of SPC$^+$ AECs by angiocrine production of MMP14. MAPK+Akt ECs were generated by transducing c-Raf, which activates MAPK pathway and E40RF1 gene that sustains Akt co-activation. Representative image (D) and quantification (E) of different groups are shown. scr, scrambled shRNA, CM, conditioned medium. F, G, Angiocrine production of MMP14 supports propagation of CCSP (YFP)$^+$Sca-1$^+$CD31$^-$ BASC-like cells. Representative image (F) and quantification (G) of various groups are shown.

FIG. 11A-F. PCEC-derived MMP14 supports regenerative alveolarization. A, After PNX, neutralizing mAb to MMP14 abolished regeneration of lung mass and volume. B, After PNX, inhibition of MMP14 diminished expansion of E-cadherin$^+$ AECs, n=5. Scale bar, 100 μm. Note lack of both cuboidal SPC$^+$E-cadherin$^+$ AECIIs (yellow arrow) and squamous SPC$^-$E-cadherin$^+$ type I-like AECs (red arrowhead) in the alveoli treated with MMP14 mAb. C, D, After PNX, MMP14 inhibition blocked expansion of E-cadherin$^+$ AECs, but not VE-cadherin$^+$CD34$^+$ PCECs, n=5. E, F, After PNX, inhibition of MMP14 suppressed alveolar regrowth and led to enlarged alveolar size. (E) Representative H&E staining of the pneumonectomized lungs treated with neutralizing mAb to MMP14 and isotype IgG. Note the increase in alveolar size in the mAb treated mice (dashed lines). (F) Quantification of alveolar number and alveolar size after PNX. Scale bar, 100 um.

FIG. 12A-J. Angiocrine production of MMP14 induces alveologenesis by shedding EGF-like ectodomains from HB-EGF and laminin5 γ2 chain. A, B, PNX induced time-dependent release of HB-EGF into alveolar space, which is inhibited in Vegfr2$^{i\Delta E/i\Delta EC}$Fgfr1$^{i\Delta EC/+}$ mice or by MMP14 neutralization. Representative Western blot image is shown in A. Control Vegfr2$^{i\Delta EC/+}$ mice treated with neutralizing mAb to MMP14 (MMP14 mAb); BAL, bronchioalveolar lavage. BALF, BAL fluid; n=4. C, At day 7 after PNX, activation of VEGFR2 and FGFR1 in PCECs upregulated MMP14, causing cleavage of laminin5 γ2 chain. D-F, EGF injection restored regeneration of lung mass and volume (D), integration of E-cadherin$^+$ AECs within the capillary (E) and pulmonary function measured by inspiratory volume and static compliance (F) in Vegfr2$^{i\Delta EC/i\Delta EC}$Fgfr1$^{i\Delta EC/+}$ mice after PNX. Note the enhanced association of SPC$^-$E-cadherin$^+$ AECIIs (red arrowhead) and SPC$^+$E-cadherin$^+$ AECIIs (yellow arrow) with the capillary. n=4. (G-I) At day 7 after PNX, intravenous EGF injection restored EGFR phosphorylation (G) and increased proliferation of SPC$^+$ AECIIs (H, I) in the Vegfr2$^{i\Delta EC/i\Delta EC}$Fgfr1$^{i\Delta EC/+}$ lung. Note the augmented proliferation in SPC$^+$ AECIIs (white arrow). Quantification of amplifying cell population after PNX is shown in I, n=4. Scale bar, 100 μm. J, Release of HB-EGF in the EC-AEC/BASC cocultured medium and MAPK+Akt EC conditioned medium (CM) is dependent on MMP14. K, Local (intratracheal) delivery of EGF resulted in an improvement in the regeneration of lung mass and volume. n=5.

FIG. 13A-G. Transplantation of wild type (WT) PCECs restores defective alveolar regeneration in mice deficient in endothelial Vegfr2 and Fgfr1. A, EC transplantation strategy to define contribution of PCECs in promoting alveolar regeneration. After PNX, ECs were purified from the lung and liver of WT littermates, transduced with lentiviral GFP, and transplanted via the jugular vein into pneumonectomized Vegfr2$^{i\Delta EC/i\Delta EC}$ Vegfr2$^{i\Delta EC/i\Delta EC}$Fgfr1$^{i\Delta EC/+}$ mice at day 3 and 7, respectively. B, Incorporation of transplanted GFP$^+$ PCECs into functional lung capillary. Intravenous infusion of vascular-specific isolectin was used to identify patent vasculature. Note the presence of perfused isolectin$^+$ GFP$^+$ PCECs indicating functional incorporation of transplanted WT PCECs into recipient Vegfr2$^{i\Delta EC/i\Delta EC}$Fgfr1$^{i\Delta EC/+}$ capillaries. Scale bar, 100 μm. C, D, Restoration of expansion potential of CCSP$^+$ BASC-like cells in Vegfr2$^{i\Delta EC/i\Delta EC}$ mice after PCEC transplantation. Note in (D) the unique localization of proliferating BrdU$^+$CCSP$^+$ BASC-like cells (red arrow) that is in close proximity to transplanted GFP$^+$ PCECs (green arrow). E-G, Transplantation of WT PCECs restores proliferation of SPC$^+$ AECs (E, F) and pulmonary function (G) in Vegfr2$^{i\Delta EC/i\Delta EC}$Fgfr1$^{i\Delta EC/+}$ mice. Expanding BrdU$^+$SPC$^+$ AECs (red arrow) were detected in close cellular association with transplanted PCECs (green arrow) (F).

DETAILED DESCRIPTION

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to allow the reader to quickly ascertain the nature and gist of the technical disclosure. The Abstract is submitted with the understanding that it will not be used to interpret or limit the scope or meaning of the claims.

The inventors have discovered that regeneration of an organ can be induced or enhanced by the application and/or activation of tissue-specific endothelial cells. While not wishing to be bound, it is postulated that these tissue-specific endothelial cells promote organogenesis by, for example, developing vasculature necessary for oxygen and nutrient exchange, and further by releasing "angiocrine" growth factors that promote angiogenesis and stimulate organ-specific tissue cells to grow and repopulate lost tissue in the affected organ.

Endothelial Cells and Tissue-Specific Endothelial Cells.

The terms "endothelial cells" and "capillary endothelial cells" (ECs) are used interchangeably herein to refer to cells of the endothelium that line the surfaces of blood or lymph vessels or capillaries, form organ microvasculature, have organ-specific phenotypic characteristics, such as cell surface expression or lack of expression of specific proteins, and perform organ-specific functional activities. In general, endothelial cells are characterized by expression of Vascular endothelial growth factor receptor-2 (VEGFR2$^+$) and VE-cadherin$^+$. ECs can optionally further express positively one or more of CD62E/E-selectin (cell adhesion molecule), VEGFR1 (Flt1), VEGFR3 (Flt4), Von Willebrand Factor (vWF; carrier of factor VIII), CD31 (FL-3 or PECAM-1), lyve-1, and Tie-2.

"Tissue-specific endothelial cells" (TSECs) are endothelial cells that are specific to a particular organ. TSECs provide a source for regrowth of organ tissues, both by inducing the proliferation of other organ-specific cells, and further by self-proliferation to form new vasculature for the regenerating tissue. TSECs can be identified by expression of EC markers plus additional markers specific to a tissue disclosed herein. This disclosure provides methods to isolate and expand tissue-specific ECs for use according to the invention, by identification of tissue-specific markers which can be used to separate TSECs from other cells, and by culture methods as described herein.

For example, liver-specific sinusoidal ECs (LSECs) are characterized as VEGFR2$^+$, VE-cadherin$^+$, VEGFR3$^+$, CD34$^-$, and factor VIII$^+$. LSECs may be characterized by one or more additional markers of Sca-1$^-$, podoplanin$^+$ (mucin-type transmembrane glycoprotein), lyve-1$^+$(hyaluronan receptor), prox-F, and stabilin-1$^+$ (hyaluronan receptor).

As a further example, lung-specific capillary ECs (PCECs) express VEGFR2$^+$, VE-cadherin$^+$, CD34$^+$, CD31$^+$, and FGFR1$^+$(FGF-2 receptor). Additional optional markers characteristic of PCECs include one or more of c-kit$^+$, cxcr-4$^+$ and CD45$^-$.

As another example, bone marrow-specific sinusoidal ECs are characterized by characteristic markers: VEGFR2$^+$, VE-cadherin$^+$, VEGFR3$^+$, and CD34$^-$. Additional optional markers characteristic of bone marrow-specific sinusoidal ECs include one or more of c-kit$^+$, cxcr-4$^+$, CD45$^-$, and Sca-1$^-$.

As an additional example, pancreatic island TSECs express VEGFR2$^+$, VE-cadherin$^+$ and CD34$^+$. Brain TSECs express VEGFR2$^+$, VE-cadherin$^+$ and CD133$^+$ and optionally further express Notch ligand$^+$ and IGFBP1$^+$(Insulin-like growth factor-binding protein-1)$^+$.

Isolation of ECs and TSECs.

This disclosure provides isolated ECs and TSECs for use in the methods of the invention. The terms "isolated" and "purified" are used interchangeably herein to refer- to a material that is substantially or essentially removed from or concentrated in its natural environment. For example, a cell is isolated if it is substantially removed from other endogenous cell types, tissues, and materials which the cell would normally be found in proximity to in a subject. Methods for purification and isolation of cell types according to expression of cell-surface markers are documented methodologies. A "substantially isolated" cell or cell population is a cell or cell population that is at least 75%, 80%, 85%, 90%, 95%, 98%, 99% or more isolated from other cell types, tissues, or materials found in the tissue of a subject. Also, a cell or cell population is "substantially purified" when at least 75%, 80%, 85%, 90%, 95%, 98%, 99% or more of the cells in a cell sample express the cell-surface markers of interest.

ECs and TSECs can be isolated by disaggregating a sample from an appropriate source organ or tissue. By "source organ or tissue" is meant the organ or tissue from which the cells are obtained. Disaggregation may be readily accomplished using techniques known to those skilled in the art. Examples of such techniques include, but are not limited to mechanical disaggregation and/or treatment with digestive enzymes and/or chelating agents that weaken the connections between neighboring cells thereby making it possible to disperse the tissue into a suspension of individual cells without appreciable cell breakage. Specifically, enzymatic dissociation can be accomplished by mincing the tissue and treating the minced tissue with any of a number of digestive enzymes, either alone or in combination. Suitable enzymes include, but are not limited to, trypsin, chymotrypsin, collagenase, elastase, hyaluronidase, DNase, pronase, and/or dispase. Mechanical disruption can be accomplished by a number of methods including, but not limited to, the use of grinders, blenders, sieves, homogenizers, pressure cells, insonators or trituration. See Freshney, Culture of Animal Cells. A Manual of Basic Technique, 2d Ed., A. R. Liss, Inc., New York, 1987, Ch. 9, pp. 107 26.

Once the source tissue has been reduced to a suspension of individual cells, the suspension can be fractionated into subpopulations from which the ECs and TSECs can be recovered. Fractionation may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. See Freshney, Culture of Animal Cells. A Manual of Basic Techniques, 2d Ed., A. R. Liss, Inc., New York, 1987, Ch. 11 and 12, pp. 137 68.

As an additional step in EC and TSEC isolation, cellular selection is employed. Selection may be "positive," in that EC and TSEC characteristics or markers are utilized to select the cells, or may be "negative," in that characteristics of other cell types within the tissue or centrifuged pellet may be utilized to exclude or remove those other cell types from the ECs and TSECs. Types of sorting procedures include magnetic bead isolation (MACS), fluorescence activated cell sorting (FACS), and elutriation. Endothelial-specific markers that may be used for selection are discussed above for ECs; TSEC selection varies by the expression pattern of the TSEC desired.

Culturing, Differentiation, and Expansion.

The isolated ECs and TSECs according to the invention can be cultured and differentiated from a variety of sources. For example, ECs and TSECs can be differentiated from induced pluripotent cells (IPCs) (Yu et al, 2007), hematopoietic stem cells (HSCs) or various other stem cells derived from other cellular samples of the subject to be treated employing methods known in the art. Similarly, ECs and TSECs can be obtained by differentiation of a variety of such stem cells that are non-autologous. Further ECs and TSECs can be differentiated from human embryonic stem cells (HESCs) (Butler, Cell stem cell 6:251-264 (2010b)). The ECs and TSECs obtained can further be transfected with E4ORF1 (Seandel, Proceedings of the National Academy of Sciences of the United States of America, 105:19288-93 (2008)) to prolong their life.

This disclosure provides methods to culture ECs and TSECs, for example as an isolated cell population for TSEC activation, or for transplantation to induce or enhance organ regeneration. ECs and TSECs can be isolated from a tissue sample as described above and expanded in culture.

For example, ECs or TSECs can be isolated from blood vessels of a source tissue or organ, washed with PBS (Ca2+, Mg2+ free) and transferred to gelatin-coated tissue culture dishes containing endothelial cell growth media (for example, EGM Endothelial Growth Medium, Lonza, Inc.; or Endothelial Cell Culture Medium, Becton Dickenson) according to the manufacturer's standard protocol. Using a sterile #10 scalpel blade, 1 mm cross sectional cuts are made along the length of the vessels. Larger vessels are first cut longitudinally with three incisions, to open and flatten the vessel, and then inverted to orient the vessel lumen towards the surface of the tissue culture dish. Immediately following the dissection, additional endothelial cell media can be added to each dish. Culture media can optionally contain media elements, for example serum, such as bovine serum, to obtain a concentration in the media of 1%, 2%, 3%, 5%, 8%, or 10% or more serum; growth factors such as EGF, VEGF, FGF, and/or IGF; and additional agents such as hydrocortisone, ascorbic acid, trypsin inhibitors, antibiotics, and/or heparin. Cultures are placed in a humidified 37° C., 5% $CO_2$ atmosphere.

EC colonies can be evident by 5-21 days of culture. Following the establishment of confluent monolayers (optimally within 30 days), spent culture medium is collected and endothelial cell monolayers are washed vigorously with PBS (Ca++, Mg++ free), trypsinized (0.25 mg trypsin/mL, 5 mmol/L EDTA, 37° C., 10 minutes; GIBCO) and subcultured into gelatin-coated 75 $cm^2$ flasks (Costar, Cambridge, Mass.) containing 20 mL of endothelial cell culture medium. EC monolayers are fed weekly with culture medium and several passages of the primary cells can be established and optionally banked.

In a specific embodiment, TSECs in the form of liver-specific ECs (Liver Sinusoidal ECs, or LSECs) are isolated. Isolation and purification of LSECs can be performed, for example, by collagenase digestion of liver tissue, followed by separation of LSECs on binding magnetic beads specific for LSEC markers, as described in Example 1, under "Isolation and culture of mouse cells". Culture of isolated LSECs can be performed as described in Example 1, under "Determination of hepatocyte proliferation in co-culture with endothelial cells". LSECs are characterized as $VEGFR3^+CD34^-$, while non-sinusoidal ECs are characterized as $VEGFR3^-CD34^+$. LSECs may be isolated from source tissues by use of magnetic beads specific for LSEC markers $VEGFR3^+CD34^-VEGFR2^+VE\text{-cadherin}^+Factor\text{-}VIII^+$.

Culture of isolated LSECs can be performed essentially as described in Example 1, under "Determination of hepatocyte proliferation in co-culture with endothelial cells". For example, LSECs can be cultured in a media suitable for culturing ECs (e.g., Williams' E Medium (Invitrogen)), supplemented with vascular endothelial growth factor-A (VEGF-$A_{164}$) (e.g., 5 ng $ml^{-1}$), and in some embodiments, also with fetal bovine serum (FBS, e.g., 1%). Additional suitable supplements include L-glutamine (e.g., 2 mmol $l^{-1}$), dexamethasone (e.g., at $10^{-9}$ mol $l^{-1}$), streptomycin (100 U $ml^{-1}$) and penicillin (100 U $ml^{-1}$). The cells can be cultured for a few days to several weeks, e.g., at least 5 days, up to 2 or 3 weeks, to generate a desirable number of cells. It will be understood by one of skill in the art that modifications to culture conditions are acceptable, provided media contains elements to maintain LSEC culture as desired, such as inclusion of VEGF-A and/or VEGF-E in culture medium.

In another specific embodiment, TSECs in the form of lung-specific ECs (Pulmonary Capillary ECs, or PCECs) are isolated. Isolation and purification of PCECs, as well as culture of primary PCECs, can be performed as for liver tissue as described above, with separation of PCECs by use of magnetic beads specific for PCEC markers $VE\text{-cadherin}^+VEGFR2^+FGFR1^+CD34^+CD31^+$.

Culture of primary PCECs can be performed as for liver tissue as described above, with addition of FGF, VEGF-A, and/or VEGF-E to the media to generate $VE\text{-cadherin}^+VEGFR2^+FGFR1^+CD34^+$ PCECs.

Inductive TSECs and Endothelial Progenitor Cells.

This disclosure further provides inductive TSECs. An "inductive" TSEC refers to a TSEC in which one or more organogenic activities is induced. Such organogenic activities include, for example, formation of vasculature, production and release of "angiocrine factors", which are tissue-specific paracrine growth factors, and induction of tissue-specific cell mitosis and/or proliferation. Generally, inductive TSECs express most or all of the markers characteristic of TSECs described hereinabove, as well as additional marker or markers. For example, inductive LSECs can be defined by expression of $VEGFR2^+VE\text{-cadherin}^+VEGFR3^+CD34^-$ factor $VIII^+wnt2^+$ and $HGF^+$(hepatocyte growth factor)$^+$. Inductive PCECs can be defined by expression of $VEGFR2^+VE\text{-cadherin}^+CD34^+CD31^+FGFR1^+MMP14^+$.

To produce inductive TSECs, TSECs can be isolated from tissue as described above according to tissue-specific expression patterns, and activated by culturing with tissue-specific growth factors. For example, LSECs can be activated by culturing with VEGF-A and/or VEGF-E to activate LSEC VEGFR2/Id1 pathways and produce inductive LSECs, while PCECs can be activated by culturing with VEGF-A, FGF-2, EGF, and/or MMP14 to activate PCEC VEGFR2/FGFR1/MAPK pathways and produce inductive PCECs.

Alternatively, inductive TSECs can be isolated from surgically-excised tissues by isolation of TSECs bearing inductive markers, for example by positive selection of TSECs bearing inductive markers by magnetic bead isolation (MACS) or fluorescence activated cell sorting (FACS) according to specific markers. Organ loss is sensed by TSECs and leads to TSEC activation to regenerate lost tissue mass; thus, inductive TSECs can be isolated directly from damaged or excised tissues. As a specific example, inductive LSECs can be directly selected in these methods by isolation of $VEGFR2^+VE\text{-cadherin}^+VEGFR3^+CD34^-factor\ VIII^+wnt2^+HGF^+$ cells from surgically removed liver tissue. As a further example, PCECs can be directly selected by isolation of $VEGFR2^+VE\text{-cadherin}^+CD34^+CD31^+FGFR1^+MMP14^+$ cells from surgically removed lung tissue.

The ECs, TSECs, and inductive TSECs, according to the invention may be autologous, allogeneic, or xenogeneic to the subject in need of organ regeneration. Most preferably, the cell types used in the present invention are autologous.

Xenogeneic cells can be isolated for example from transgenic animals expressing appropriate cell markers.

Interactions of TSECs and Other Non-Endothelial Tissue-Specific Cells Regenerate Organ Mass.

This disclosure provides inductive TSECs which interact with non-endothelial tissue-specific cells, both in vivo and in vitro, to promote tissue growth. Activation of TSECs leads to induction of mitosis and proliferation of non-endothelial tissue-specific cells. Proliferation of non-endothelial tissue-specific cells is necessary for restoration of organ mass and function, and is driven in part by TSEC-mediated angiocrine signals and cell-cell contact. An example of a liver-specific non-endothelial cell is a hepatocyte; examples of lung-specific non-endothelial cells include alveolar epithelial progenitor cells (AECs, such as AECII cells) and BASCs.

For example, in the liver, inductive LSECs stimulate hepatocyte proliferation through a process of "inductive angiogenesis"; that is, LSECs promote hepatocyte proliferation via angiocrine production of hepatocyte growth factor (HGF) and Wnt2. Subsequent to this inductive angiogenesis, LSECs themselves undergo "proliferative angiogenesis" to meet the increased demand in blood supply for the regenerating liver tissue.

As a further example, inductive PCECs stimulate proliferation of pulmonary epithelial progenitor cells that collectively rebuild functional alveolar-capillary sacs in the lung. In early phases of lung regeneration, activation of VEGFR2 in PCECs causes upregulation of MMP14 and expansion of pulmonary epithelial progenitor cells. PCEC FGFR1 expression level is induced subsequent to VEGFR2 activation. FGFR1 then synergizes with VEGFR2 in augmenting MMP14 generation, thereby sustaining alveolar regeneration. Sequential activation of VEGFR2 and FGFR1 in PCECs therefore induces regeneration of the functional alveolar-capillary units in part by MMP14 production leading to proliferation of pulmonary epithelial progenitor cells.

This disclosure further provides methods to co-culture TSECs and other non-endothelial tissue-specific cells, to enhance or induce organ regeneration. Co-culture of non-endothelial tissue-specific cells with TSECs can increase the cell numbers of both non-endothelial tissue-specific cells and TSECs in culture. For example, co-culture of TSECs and non-endothelial tissue-specific cells is expected to increase the number of TSECs by at least 5%, at least 10%, at least 15%, at least 20%, at least 25%, at least 30%, at least 40%, at least 50% or more from the initial number of TSECs seeded in the culture. Alternatively, or in addition, co-culture of TSECs and non-endothelial tissue-specific cells is expected to increase the number of non-endothelial tissue-specific cells by at least 5%, at least 10%, at least 15%, at least 20%, at least 25%, at least 30%, at least 40%, at least 50% or more from the initial number of non-endothelial tissue-specific cells seeded in the culture. Methods for determining cell numbers in vitro are known in the art.

In one embodiment, this disclosure provides a method of expanding hepatocytes in culture by co-culturing said hepatocytes with liver sinusoidal endothelial cells. For co-culture of LSECs with hepatocytes, 10,000 isolated primary hepatocytes are plated in a 100-mm dish coated with type I collagen and seeded with 500,000 LSECs. Culture conditions comprised Williams' E Medium (Invitrogen) supplemented with L-glutamine (2 mmol $l^{-1}$), 1% fetal bovine serum (FBS), vascular endothelial growth factor-A (VEGF-$A_{164}$) (5 ng $ml^{-1}$), dexamethasone at $10^{-9}$ mol $l^{-1}$, streptomycin (100 U $ml^{-1}$) and penicillin (100 U $ml^{-1}$). Cells were collected after 2 weeks of incubation. Co-incubation of isolated hepatocytes with LSECs can lead to a two-fold, three-fold, five-fold, seven-fold, or nine-fold or more increase in hepatocyte number.

Thus, this disclosure provides methods of expanding hepatocytes in culture by co-culturing the hepatocytes with liver sinusoidal endothelial cells. The inventors have determined that co-culture of hepatocytes and LSECs leads to expansion of hepatocytes. Such hepatocytes can then be prepared for administration to a subject in need of liver regeneration.

In another embodiment, this disclosure provides a method of expanding lung epithelial progenitor cells in culture by co-culturing said lung epithelial progenitor cells with pulmonary capillary endothelial cells. For co-culture of PCECs and lung-specific SPC AECII and BASC epithelial progenitor cells, isolated epithelial progenitor cells are seeded with 10-fold more PCECs under culture conditions as described above, with addition of c-Raf to culture medium to generate MAPK-activated ECs (Akt+MAPK PECs). For co-culture, isolated SPC AECIIs and BASCs are plated in a nonadherent dish, and seeded with 10-fold more Akt+MAPK-PCECs. Conditioned medium from Akt$^+$ MAPK-ECs is added to AECs. After coculture, AECIIs, BASCs, and PCECs can be quantified by, for example, flow cytometric analysis.

Following expansion in culture, TSECs and other non-endothelial tissue-specific cells can be prepared for introduction into a subject in need of organ regeneration. Cultured TSECs and/or non-endothelial tissue-specific cells can be cultured in media consistent with growth of cells for re-introduction into a human subject, for example, by using culture media with components derived from non-animal sources to minimize immunogenic response to re-introduced cells. Such specialized media and media components are commercially available (for example, from Lonza, Inc.) and can be used according to manufacturer's protocols. Prior to introduction into a subject, the cells are washed to remove residual culture medium and formulated into a cell preparation for administration to the subject. As used herein, a "cell preparation" refers to a composition of TSECs, inductive TSECs, EPCs, and/or non-endothelial tissue-specific cells that can be administered to a subject. A cell preparation can be optionally combined with additional excipients to form a pharmaceutical composition for introduction into a subject.

Organ Regeneration.

This disclosure provides a method of enhancing or initiating regeneration of an organ in a subject in need thereof comprising the administration of endothelial cells specific to said organ or inductive endothelial cells specific to said organ, into the area of the body in which organ regeneration is desired in said subject, in an amount sufficient to enhance or initiate organ regeneration.

As used herein, a "subject" includes any animal, including mammals, preferably mice, rats, other rodents, rabbits, dogs, cats, swine, cattle, sheep, horses, or primates, and most preferably humans. The methods and compositions of the invention can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The subject treated in the methods of the invention is a subject in whom organ regeneration is desired.

As used herein, the term "organ regeneration" refers to growth or regrowth of an organ, or of a portion of an organ. A preferred outcome of organ regeneration is improvement or restoration of organ function. Organ regeneration can be characterized, for example, by an increase in organ-specific cells, organ-specific tissue, and/or organ-specific function, relative to the amount of organ-specific cells, organ-specific tissue, and/or organ-specific function prior to treatment. An increase in organ-specific cells or organ-specific tissue can be determined, for example, by measuring the number of organ-specific cells, or measuring the amount of tissue by mass or volume, after treatment with the methods and compositions of the invention, and comparing such measurements with measurements of organ-specific cells or tissue prior to treatment. Measurements of organ mass or volume may be calculated in vivo, for example, through use of imaging techniques such as MRI. Increases in cell number, mass, or volume of an organ following treatment according to the methods of the invention can be an increase of at least 5%, at least 10%, at least 15%, at least 20%, at least 25%, at least 30%, at least 40%, at least 50% or more of cell number, mass, or volume, relative to the estimated or actual cell number, mass, or volume of said organ prior to treatment.

Similarly, an increase in organ-specific function can be determined by measuring one or more aspects of organ function after treatment with the methods and compositions of the invention, and comparing such measurements with measurements of organ function prior to treatment. Increases in organ-specific function following treatment according to the methods of the invention can be an increase of at least 5%, at least 10%, at least 15%, at least 20%, at least 25%, at least 30%, at least 40%, at least 50% or more in one or more aspects of organ function, relative to said one or more aspects of organ function prior to treatment. Methods of conducting such measurements are known in the art.

As used herein, to "enhance" organ regeneration refers to increasing the amount of cell number, mass, volume, or function of an organ in need of regeneration, or increasing the speed of organ regeneration, in a subject where some organ regeneration may be naturally occurring, but where such naturally-occurring organ regeneration is inadequate in amount or speed of regeneration. An inadequate amount or speed of regeneration, for example, would be increase of less than 1%, 2%, 5%, 10%, or 20% of organ-specific cell number, mass, volume, or function over a period of 90 days. To "initiate" organ regeneration refers to increasing the amount of cell numbers, mass, or volume of an organ in need of regeneration, or increasing the speed of organ regeneration, in a subject where no organ regeneration is evidently occurring.

This disclosure further provides cell preparations and compositions containing tissue-specific ECs, and inductive TSECs, optionally in combination with a biologically-acceptable carrier and optionally further in combination with non-endothelial tissue-specific cells. For example, the cells disclosed herein can be incorporated into pharmaceutical compositions suitable for administration. Such compositions can include the cell preparation and an additional acceptable carrier. As used herein, "biologically acceptable carrier" is intended to include any and all solvents, dispersion media, coatings, antibacterial, and antifungal agents, isotonic and absorption delaying agents, and the like, compatible with biologics administration. Suitable carriers are described in the most recent edition of Remington's Pharmaceutical Sciences, a standard reference text in the field, which is incorporated herein by reference.

Preferred examples of such carriers or diluents include, but are not limited to, water; saline; dextrose solution; human serum albumin; HBSS and other buffered solutions (including those with and without $Ca^{++}$ and $Mg^{++}$) known to those skilled in the relevant arts; and basal media. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions. For example, pharmaceutical compositions may optionally further comprise growth factors such as VEGF-A, VEGF-E, FGF-2, EGF, or MMP14.

For liver regeneration, the pharmaceutical composition in specific embodiments include $VEGFR3^+CD34^-VEGFR2^+$ $VE\text{-}cadherin^+FactorVIII^+Prox\text{-}1^-CD45^-$ cells. For lung regeneration, the pharmaceutical composition in specific embodiments include $VE\text{-}cadherin^+VEGFR2^+FGFR1^+$ $CD34^+$ cells.

A cell preparation according to the invention can include TSECs, and inductive TSECs, optionally in combination with non-endothelial tissue-specific cells, and further admixed or combined with a supporting biological or synthetic extracellular matrix or matrix material (ECM). One skilled in the art will recognize that the term "ECM" refers to the noncellular material distributed throughout the body of multicellular organisms. Such an admixture can provide a scaffold for the growth of organ tissue. The ECM is comprised of diverse constituents such as glycoproteins, proteoglycans, complex carbohydrates, and other molecules. Major functions of the ECM include, but are not limited to, providing structural support, tensile strength or cushioning; providing substrates and pathways for cell adhesion and cell migration; and regulating cellular differentiation and metabolic function. ECM proteins include, for example, collagens, elastin, fibronectin, laminin, proteoglycans, vitronectin, thrombospondin, tenascin (cytoactin), entactin (nidogen), osteonectin (SPARC), anchorin CII, chondronectin, link protein, osteocalcin, bone sialoprotein, osteopontin, epinectin, hyaluronectin, amyloid P component, fibrillin, merosin, s-laminin, undulin, epilligrin, and kalinin. Preferred ECM proteins for use according to this invention include collagen, alginate, agarose, fibrin, fibrin glue, fibrinogen, laminins, fibronectins, HSP, chitosan, heparin and/or other synthetic polymer or polymer scaffolds.

The compositions or preparations may be formulated for parenteral administration by injection, e.g., by bolus injection or continuous infusion. The compositions may take such forms as suspensions, solutions or emulsions in oily or aqueous vehicles, and may contain formulatory agents such as suspending, stabilizing and/or dispersing agents. The compositions or preparations may alternatively be prepared as a graft to be administered, for example, to an affected area during a surgical procedure, such as immediately subsequent to removal of an affected organ or portion thereof.

The administration of a composition according to the invention is conducted in accordance with a variety of factors including species, age, weight, sex, and medical condition of the patient; type and severity of the damaged or diseased organ for which regeneration is desired; the route of administration; and the particular cells employed. An ordinarily skilled physician or veterinarian can readily determine and prescribe the effective amount required to enhance or induce organ regeneration.

As used herein, a "sufficient amount" is the amount of cells or pharmaceutical composition to be administered to a subject to achieve an increase in organ-specific cells, organ-specific tissue, and/or organ-specific function, as defined above. For example, treatment with the methods or compositions of the invention can increase organ-specific cell number, mass, volume, or function, by more than 1%, more than 2%, more than 5%, more than 10%, or more than 20% over a period of 180 days, relative to the amount of organ-specific cell number, mass, volume, or function prior to treatment.

The TSECs, inductive TSECs, or compositions of the invention are administered to patients in amounts sufficient to treat the patient, as can be determined by a skilled practitioner. The numbers of cells necessary for treatment will depend on a number of factors including the type of organ, the size (or area) of the lost or damaged organ component as determined using a medical imaging technique such as MRI, the age and/or weight of the patient, and the like. Generally, it is expected that cell numbers in the range of $1\times10^6$ to $10\times10^6$, and more preferably $2\times10^6$ to $8\times10^6$ can be administered to the patients. Thus depending on the particular patient and the organ to be treated, the number of cells administered can be about $2\times10^6$, about $3\times10^6$, about $4\times10^6$, about $5\times10^6$, about $6\times10^6$, about $7\times10^6$, or about $8\times10^6$. These amounts may refer to the total number of TSECs, or the total of all cells administered to the subject, for example if TSECs are co-administered with other non-endothelial tissue-specific cells, as in hepatic co-administration of LSECs and hepatocytes. In a further embodiment, TSEC growth factors, such as VEGF for LSEC activation, or EGF for PCEC activation, are administered during or after administration of TSECs to a subject.

Following administration of the cells or compositions according to the invention, organ regeneration can be measured by increases in cell number, organ mass or volume, and/or organ function, as described above.

In an embodiment of the invention, a pharmaceutical composition or cell preparation of the invention is administered during or after surgical excision of an organ, for example during or after hepatectomy or pneumonectomy.

Liver-Specific Regeneration.

This disclosure provides methods of enhancing liver regeneration. One embodiment of the invention provides a method of enhancing liver regeneration in a mammal in need thereof comprising the intrahepatic administration of liver-specific endothelial cells or inductive liver-specific endothelial cells.

The liver disease leading to liver degeneration can be hepatocellular carcinoma, liver cirrhosis, liver fibrosis and hepatitis. Liver fibrosis refers to the growth of scar tissue in the liver due to any of a variety of chronic toxic insults, including, but not limited to, chronic alcohol abuse; chronic exposure to drugs (e.g., acetominophen, amiodarone, aspirin, azathioprine, isoniazid, methyldopa, methotrexate, mitrfurantoin, propylthiouracil, statins, and sulfonamides); chronic exposure to certain chemical agents (e.g., carbon tetrachloride, dimethyl nitrosamine, vinyl chloride, polychlorinated biphenyls, aflatoxins, and pesticides); infection with *Schistosoma mansoni*; diabetes; autoimmune disorders (e.g., primary sclerosing cholangitis, primary biliary cirrhosis, autoimmune hepatitis, lupoid hepatitis), and inflammatory bowel disease; and other conditions. Liver cirrhosis is a degenerative condition in which the liver parenchyma deteriorates, the lobules are infiltrated with fat and dense perilobular connective tissue is formed. As a result, the blood supply to the remaining cells is reduced leading to portal hypertension and eventually death. In addition, there are some genetic diseases, such as Wilson's disease, HHC, and alpha-1 Anti-Trypsin deficiency, that cause the liver to dysfunction, and may cause cirrhosis or chronic hepatitis.

This disclosure further provides methods of enhancing or initiating liver regeneration, comprising administration of VEGF, alone or in combination with administration of LSECs. The inventors have discovered that LSECs express VEGFR2 and VEGFR3 in the liver, and administration of VEGF-A and/or VEGF-E induces LSEC activation, LSEC-mediated stimulation of hepatocyte proliferation, LSEC proliferation, liver regeneration, and liver revascularization.

This disclosure further provides methods to enhance or induce liver regeneration by administration of VEGF-A, VEGF-E or FGF-2, and/or an Id1 agonist, to a subject in need thereof. The inventors have determined that these growth factors promote liver organogenesis by induction of hepatocyte and LSEC generation and angiogenesis in regenerating tissue, thus promoting normal liver function.

This disclosure further provides methods to enhance or induce liver regeneration by intrahepatic administration of LSECs. The inventors have found that LSECs induce hepatocytes to proliferate and form new tissue. After induction of hepatocyte proliferation, LSECs themselves proliferate to provide vascular support for the regenerating tissue.

This disclosure also provides a method to improve hepatovascular function in a subject suffering from reduced liver function, comprising the intrahepatic co-transplantation of hepatocytes with LSECs, particularly VEGFR2$^+$Id1$^+$ LSECs.

As used herein, the phrase "liver function" refers to a function of the liver, including, but not limited to, protein synthesis such as serum proteins [e.g., albumin, clotting factors, alkaline phosphatase, aminotransferases (e.g., alanine transaminase, aspartate transaminase), 5'-nucleosidase, gamma.-glutaminyltranspeptidase, etc.], synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; excertion function of cholesterol, bile acids, phospholipids and bilirubin; and a hemodynamic function, including splanchnic and portal hemodynamics.

Lung-Specific Regeneration.

This disclosure provides methods of enhancing or inducing lung regeneration. In one embodiment the present disclosure provides a method for inducing lung or alveolar regeneration in a mammal in need thereof comprising the intravenous or intratracheal administration of pulmonary capillary endothelial cells (PCECs) or inductive PCECs, in an amount sufficient to enhance or induce lung regeneration.

Another embodiment of the present invention provides a method to induce alveolarization in a mammal in need thereof by the intravenous or intratracheal administration of PCECs or ECs expressing MMP14.

A further embodiment of the present invention provides a method to induce alveolarization in a mammal in need thereof by administering MMP14.

This invention also provides a method to induce alveolarization in a mammal in need thereof by the intravenous or intratracheal administration of PCECs expressing epithelial growth factor (EGF) or EGF-receptor ligands, including HB-EGF and the EGF-like fragment from laminin5 γ2.

A further embodiment of the present invention provides a method to induce alveolarization in a mammal in need thereof by administering EGF.

Another embodiment of the present invention provides a method to induce alveolarization in a mammal in need thereof by administration of VEGF-A, VEGF-E or FGF-2 for activation of VEGFR2 or FGFR1 expressed on PCECs.

The lung regeneration induced by the methods of this invention will be useful in treating various lung diseases and injuries where lung function is impaired or lung capacity is reduced. These methods will be useful for regeneration of lung tissue following surgical excision of damaged, diseased, or cancerous lung tissue. These methods will further be useful, for example, for lung diseases that involve inflammation and/or the premature death of endothelial cells. The lung diseases that could be treated with these methods include, but are not limited to, Adult Respiratory Distress Syndrome (ARDS), post-traumatic ARDS, emphysema, Chronic Obstructive Pulmonary Distress syndrome (COPD), chronic bronchitis, asthma, emphysema, lung hypoplasia, pulmonary hypertension, cystic fibrosis, lung cancer, asthma, lung trauma, or other genetic or congenital lung abnormalities, e.g., bronchogenic cyst, pulmonary agenesis and hypoplasia, polyalveolar lobe, alveolocapillary dysplasia, sequestration including arteriovenous malformation (AVM) and scimitar syndrome, pulmonary lymphangiectasis, or congenital lobar emphysema.

The lung injury can be a chemically-induced lung injury. The lung injury can be caused by a pulmonary disease. The lung injury can be caused by at least one condition selected from the group consisting of: pulmonary fibrosis, sarcoidosis, asbestosis, aspergilloma, aspergillosis, pneumonia, pulmonary tuberculosis, rheumatoid lung disease, bronchiectasis, bronchitis, bronchopulmonary dysplasia or interstitial lung disease.

As used herein, the phrases "lung function" and "pulmonary function" refer to a function of the lungs and/or pulmonary system, including, but not limited to, breathing, oxygen intake, CO expiration, respiration, gas exchange, and production of mucus and bronchial secretions.

EXAMPLES

The present description is further illustrated by the following examples, which should not be construed as limiting in any way. The contents of all cited references (including literature references, issued patents, published patent applications as cited throughout this application) are hereby expressly incorporated by reference.

Example 1

Liver Regeneration

Transgenic Reporter and Gene Targeted Animals

C57BL/6J mice were obtained from Jackson Laboratories. VEGFR2-GFP mice were acquired from J. Rossant (Ema, Blood 107:111-117 (2006)). Id1$^{-/-}$ mice were generated as previously described (Nam, Cell Stem Cell 5:515-526 (2009)) and obtained from R. Benezra and D. Lyden.

VEGFR2$^{loxP/loxP}$ mouse was generated by T. N. Sato and experiments with endothelial-specific inducible VEGFR$^2$ knockout mice were performed as previously described (Hooper, Cell Stem Cell 4:263-274 (2009)). Briefly, the VEGFR2$^{loxP/loxP}$ mice and then bred with RosaCre-ER$^{T2}$ transgenic mice to establish the RosaCre-ER$^{T2}$ VEGFR2$^{loxP/loxP}$ line and control ROSA-CreER$^{T2}$VEGFR2$^{loxP/+}$ to account for potential Cre-mediated toxicity. To induce endothelial-specific knockdown of VEGFR$^2$, VE-cadherin-CreER$^{T2}$ mice provided by L. Iruela-Arispa were also crossed with VEGFR2$^{loxP/loxP}$ mice to generate VE-cadherin-CreER$^{T2}$VEGFR2$^{loxP/loxP}$ mice. To induce VEGFR2 gene ablation, 6- to 8-week-old male mice were treated with tamoxifen at a dose of 250 mg kg$^{-1}$ sunflower oil intraperitoneally for 6 days, interrupted for 3 days after the third dose. After 3 days of respite, the fourth dose was reinstituted for an additional 3 days, resulting in ROSA-CreER$^{T2}$VEGFR2$^{flox/flox}$ (VEGFR2$^{fl/fl}$) mice that were deficient in VEGFR2 at both alleles, the control ROSA-CreER$^{T2}$VEGFR2$^{fl/+}$ mice or VE-cadherin-CreER$^{T2}$VEGFR2$^{fl/fl}$ mice that had endothelial-cell-specific VEGFR$^2$ knockdown. All animal experiments were performed under the guidelines set by the Institutional Animal Care and Use Committee.

A 70% partial hepatectomy model was used to induce physiological liver regeneration in mice. Three most anterior lobes (right medial, left medial and left lateral lobes), which comprise 70% of the liver weight, were resected, without injuring the blood supply to the caudate and the right lobes. Mice were anaesthetized by 100 mg kg$^{-1}$ intraperitoneal ketamine and 10 mg kg$^{-1}$ xylazine. Midline laparotomy was performed in the anaesthetized mice. After opening the upper abdomen and the exposure of the liver, the left lobe to be resected was gently lifted while a 5-0 silk suture tie (Roboz) was placed underneath the lobe and positioned as proximal to the origin of the lobe as possible. The two ends of the suture were tied over the top of the liver lobe at the base of the lobe near the inferior vena cava. Three knots were tied, and microdissecting scissors was used to cut the tied lobe just distal to the suture. This process was repeated for the other median lobes to perform 70% partial hepatectomy. Then the peritoneum was re-approximated with a running 5-0 silk suture and the skin was closed with a running 4-0 silk suture.

Sham-operated mice underwent laparotomy without liver resection. To characterize the regeneration of liver mass and function, the weight of residual liver lobes were measured and normalized to mouse body weight at various time points days after partial hepatectomy, and plasma bilirubin levels were assayed (Genzyme Diagnostics) after 70% partial hepatectomy, respectively. To compare partial hepatectomy model to CCl$_4$-induced liver injury model, CCl$_4$ was intraperitoneally injected as previously described (LeCouter, Science 299:890-893 (2003)). To test liver regeneration promoted by VEGF-A or P1GF, mice were treated with 15 μg kg$^{-1}$ of recombinant VEGF$_{164}$ (Biovision) and the same amounts of P1GF (Biovision) 12 h before the operation and twice a day thereafter. Id1$^{-/-}$ mice and wild-type littermates were also subjected to similar VEGF$_{164}$ and PBS treatment before and after operation.

Liver Immunofluorescence and Detection of GFP

VEGFR2-GFP, VEGFR2$^{fl/fl}$, Id1$^{-/-}$ and littermate control mice were subjected to partial hepatectomy or sham-operation, perfused with 4% paraformaldehyde, cryoprotected and snap frozen in OCT. For the analysis of the liver microvasculature, mice were intravenously injected with 2 mg kg$^{-1}$ *Griffonia simplicifolia* lectin (isolectin B4, Invitrogen) 5 min before being killed, as previously described (Hooper, Cell Stem Cell 4:263-274 (2009)). For immunofluorescence microscopy, the liver sections (10 μm) were blocked (5% donkey serum/0.3% TRITON X-100) and incubated in primary antibodies: anti-VEGFR3 monoclonal antibody (mAb, mF4-31C1, 10 μg ml$^{-1}$, ImClone), anti-VE-cadherin polyclonal Ab (pAb, 2 μg ml$^{-1}$, R&D Systems), anti-CD34 mAb (553731, 5 μg ml$^{-1}$, BD Biosciences), anti-phospho-Histone H3 (Millipore) and anti-HNF4A antibody (Abcam). After incubation in fluorophore-conjugated secondary antibodies (2.5 μg ml$^{-1}$, Jackson ImmunoResearch), sections were counterstained with TOPRO3 or DAPI (Invitrogen).

Liver cell proliferation in vivo was measured by BrdU uptake. Briefly, mice received a single dose of BrdU (Sigma) intraperitoneally 60 min before death (at a dose of 50 mg kg$^{-1}$ animal weight). At the time of death, mice were anaesthetized, blood was collected from the inferior vena cava, and the remaining liver lobes were removed, weighed and further processed. Cryosections were stained using the BrdU Detection System (BD Biosciences) and fluorophore-conjugated secondary antibodies (2.5 µg ml$^{-1}$, Jackson ImmunoResearch).

Image Acquisition and Image Analysis

Immunohistochemistry images of liver sections were captured with AXIOVISION software (Zeiss) mounted on an Olympus BX51 microscope (Olympus America). Immunofluorescence images were captured on AXIOVERT LSM510 or 710 confocal microscope (Zeiss). Digital images were analysed for the density of endothelial marker (VE-cadherin$^+$) and functional perfused vessels (isolectin$^+$) using Image J (National Institutes of Health). Vessel density was expressed by the percentage of positive component to the total area in each high-power field, ×400.

Isolation and Culture of Mouse Cells

Hepatocytes, LSECs, stellate and Kupffer cells were isolated from mice that underwent sham-operation and partial hepatectomy, by a two-step collagenase perfusion technique with modifications (Tam, Nature Med. 12:793-800 (2006); Passino, Science 315:1853-1856 (2007); Kumar, J. Clin. Invest. 116:512-520 (2006); Winau, Immunity 26:117-129 (2007); Kreamer, In Vitro Cell. Dev. Biol. 22:201-211 (1986)). Briefly, after the inferior vena cava was cannulated and portal vein was cut, the liver was perfused at 5 ml min$^{-1}$ through the inferior vena cava with Liver Perfusion Medium (Invitrogen) at 37° C. for 10 min, followed by perfusion with Liver Digest Medium (Invitrogen) for an additional 10 min. The liver was dissociated in Hepatocyte Wash medium (Invitrogen), passed through dacron fabric with 70-µm pores and separated from the non-parenchymal hepatocyte depleted fraction (NPCs) by low-speed centrifugation (50 g×5 min), which were further purified by percoll gradient centrifugation, using stock Percoll solution as previously described (Kreamer, In Vitro Cell. Dev. Biol. 22:201-211 (1986)). The supernatant containing NPCs was collected and was washed twice at 50 g for 5 min, pelleted at 350 g for 7 min and fractionated with Percoll gradient centrifugation (900 g×20 min) with 75% stock Percoll solution and 35% stock Percoll solution, as previously described (Kreamer, In Vitro Cell. Dev. Biol. 22:201-211 (1986)). Fractions containing LSECs were enriched, mixed with an equal volume of PBS and centrifuged at 900 g for 7 min. The pellet was washed with DMEM (Invitrogen) at 350 g for 7 min and further labelled by mouse LSEC binding magnetic beads (Miltenyi). The purification of LSECs was performed according to the manufacturer's protocol. Purification of stellate and Kupffer cells was performed as previously described (Passino, Science 315:1853-1856 (2007); Kumar, J. Clin. Invest. 116:512-520 (2006); Winau, Immunity 26:117-129 (2007)).

Flow Cytometric Analyses, Identification and Quantification of LSECs

Purified monoclonal antibodies were conjugated to ALEXA FLUOR dyes or QDOTS per manufacturer's protocols (Molecular Probes/Invitrogen). Purified hepatocyte-depleted NPCs were analysed on LSRII-SORP (BD Biosciences). Data were processed with FACSDIVA 6.1 software (BD Biosciences). Doublets were excluded by FSC-W× FSC-H and SSC-W×SSC-H analysis, single-stained channels were used for compensation and fluorophore minus one controls were used for gating. Monoclonal antibodies were purchased from BD Biosciences except where noted: VE-cadherin (BV13, ImClone); VEGFR3 (mF4-31C1, ImClone); VEGFR2 (DC101, ImClone); CD45 (30-F11, BD Biosciences); CD34 (14-0341, eBioscience).

For quantification of LSECs, the livers were mechanically prepared as above and the number of SECs was quantified by co-staining with conjugated antibodies to VEGFR2, VEGFR3, VE-cadherin, CD34. The number of SECs equals the number of VEGFR3$^+$CD34$^-$VEGFR2$^+$VE-cadherin$^+$ cells. VEGFR3$^-$CD34$^+$VEGFR2$^+$VE-cadherin$^+$ cells were scored as non-SECs.

Determination of Hepatocyte Proliferation in Co-Culture with Endothelial Cells

Human LSECs were from ScienCell Research Laboratories. To knockdown Id1 selectively in LSECs, Id1/Scrambled short hairpin RNA (shRNA) lentiviruses were generated by co-transfecting 15 µg of shuttle lentiviral vector containing Id1/Scrambled shRNA, 3 µg of pENV/VSV-G, 5 µg of pRRE and 2.5 µg of pRSV-REV in 293T cells by Fugene 6 (Roche Applied Science). Viral supernatants were concentrated by ultracentrifugation. These concentrated viral preparations were used to transduce LSECs or hepatocytes.

For co-culture studies, 10,000 isolated primary hepatocytes were plated in a 100-mm dish coated with type I collagen, seeded with 500,000 LSECs, or with LSECs treated with Id1/scramble shRNA lentivirus, respectively. Culture conditions consisted of Williams' E Medium (Invitrogen) supplemented with L-glutamine (2 mmol l$^{-1}$), 1% fetal bovine serum (FBS), vascular endothelial growth factor-A (VEGF-A$_{164}$) (5 ng ml$^{-1}$), dexamethasone at 10$^{-9}$ mol l$^{-1}$, streptomycin (100 U ml$^{-1}$) and penicillin (100 U ml$^{-1}$). Cells from each group were collected after 2 weeks. To visualize LSECs and hepatocytes, LSECs were marked by mCherry lentivirus (in pCCL backbone) as described above, and hepatocytes were infected with GFP lentivirus. Conditioned medium was also collected from 500,000 LSECs cultured for 2 weeks, filtered through a 0.22 µm filter, and added to 10,000 hepatocytes at 1:2 dilution, in the absence of LSEC co-culture. The numbers of LSECs and hepatocytes were assessed by flow cytometric analysis of mCherry and GFP signals. Hepatocyte proliferation was quantified by comparing the number of retrieved hepatocytes to the initially seeded hepatocyte number.

Affymetrix Analysis and Quantitative Real-Time PCR Analysis

RNA was freshly isolated from the liver using RNEASY (Qiagen) and was converted to complementary DNA using SUPERSCRIPT II (Invitrogen). Microarray was performed using Mouse U133 2.0 (Affymetrix). Details of the methods for RNA quality, sample labelling, hybridization and expression analysis were according to the manual of the Affymetrix Microarray Kit. Quantitative PCR was performed using TAQMAN gene expression systems for mouse VEGFR2, VEGFR3, Id1, HGF, Wnt2, Wnt9B and TM (Applied Biosystems).

Liver Transplantation of Regenerative LSECs

Multi-lobular 70% partial hepatectomy was performed in wild-type (Id1$^{+/+}$) mice and age- and sex-matched Id1$^{-/-}$ mice. Forty-eight hours after partial hepatectomy, LSECs were isolated from wild-type mice (Id1$^{+/+}$ regenerative LSECs) and marked by GFP lentivirus (in pCCL backbone) transduction as described above. The transplantation procedure was modified from that previously described (Follenzi, J. Clin. Invest:118, 935-945 (2008)). Briefly, 48 h after partial hepatectomy, Id1$^{-/-}$ mice were anaesthetized and placed in the right lateral decubitus position. The left flank was scrubbed with Betadine, and the skin and abdominal wall were incised longitudinally (parallel to the spine). After the spleen was exteriorized, $Id1^{+/+}$ regenerative LSECs were injected into the parenchyma of the spleen through a 27-gauge needle. A splenectomy was performed after the injection. To compare the rescuing effect of $Id1^{+/+}$ regenerative LSECs, $Id1^{-/-}$ and wild-type mice also subjected to the intrasplenic injection of PBS and splenectomy 2 days after partial hepatectomy (sham transplant). To introduce Wnt2 and HGF expression in LSECs, Wnt2 and HGF complementary DNAs were purchased from Open Biosystems and cloned into lentiviral vector as described above. Infection of LSECs with virus encoding Wnt2 or HGF, or the same amounts of mixed Wnt2 and HGF, was performed with GFP lentivirus infection.

Data Analysis

All data are presented as the mean±s.e.m. of at least three separate experiments. Differences between groups were tested for statistical significance using Student's t-test or analysis of variance. Statistical significance was set at $P<0.05$.

Partial Hepatectomy and Liver Regeneration.

Figure 1:
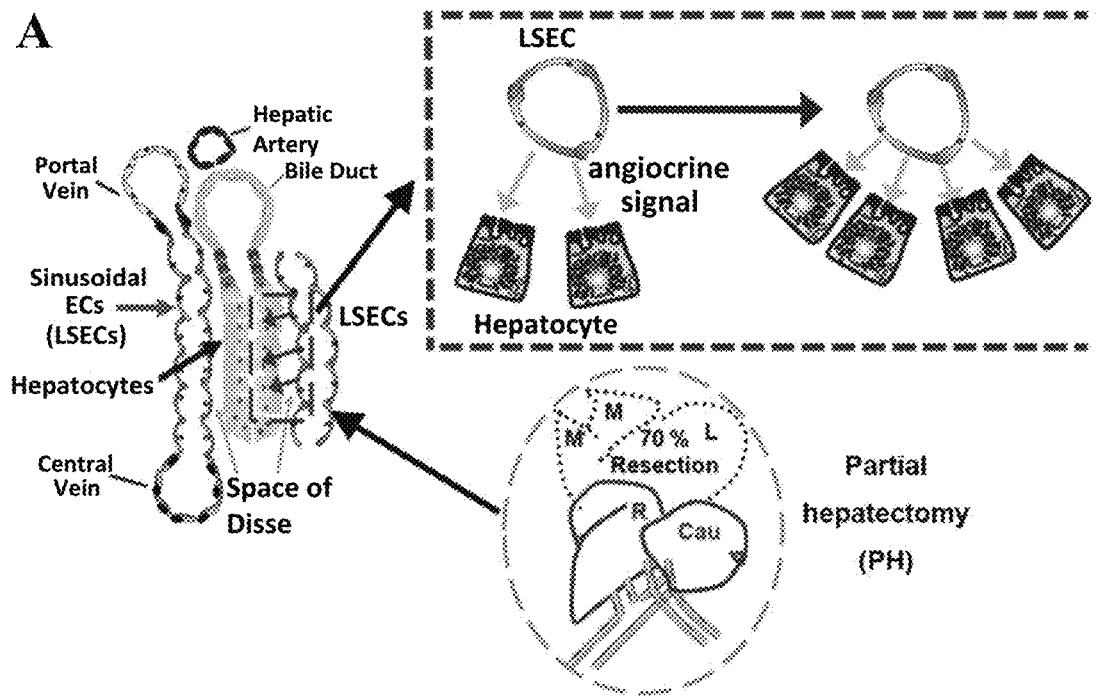
FIG. 1A-B. Inductive role of organ-specific endothelial cell-derived angiocrine signals in liver and lung regeneration. A, LSECs lining the liver sinusoid are positioned to the vicinity of hepatocytes. Upon resection of 70% of liver mass (partial hepatectomy, PH), inductive angiogenic LSECs initiate and sustain the regeneration of proximal hepatocytes, through the elaboration of specific angiocrine signals. M, R, L, and Cau; median, right, left, and caudate lobes of the liver. B, Regenerative alveolarization through proliferation of lung epithelial progenitors. PNX-induced alveolar regeneration is primarily mediated by PCEC-driven amplification of BASCs and AECs.
Figure 1:
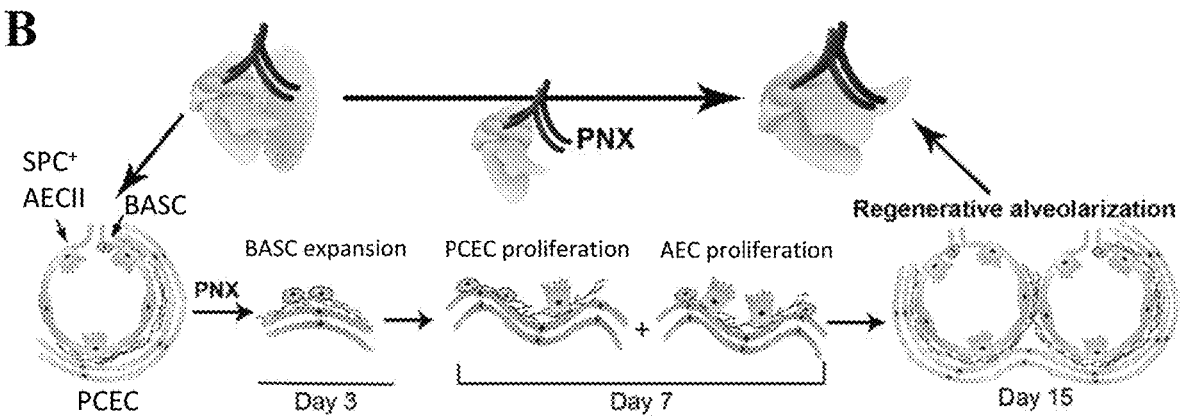

The inventors utilized a physiologically relevant partial hepatectomy model to elucidate the instructive role of LSECs in mediating hepatic regeneration (FIG. 1A). In contrast to the administration of hepatotoxic chemicals, which impairs the organization of LSECs and causes tissue hypoxia, cell death and inflammation (Lee, Hepatology 45:817-825 (2007); LeCouter, Science 299:890-893 (2003); Friedman, Physiol. Rev. 88:125-172 (2008)), in the partial hepatectomy model, resection of 70% of the liver mass without perturbing the integrity of the residual liver vasculature (Greene, Ann. Surg. 237:530-535 (2003)) activates hepatocyte regeneration (Fausto, Hepatology 43:S45-S53 (2006); Michalopoulos, Science 276:60-66 (1997); Greenbaum, J. Clin. Invest. 102:996-1007 (1998)). As such, this model provides an instructive model for interrogating the role of structurally and functionally intact LSECs in supporting liver regeneration.

VEGF is Involved in Liver Regeneration

Figure 2:
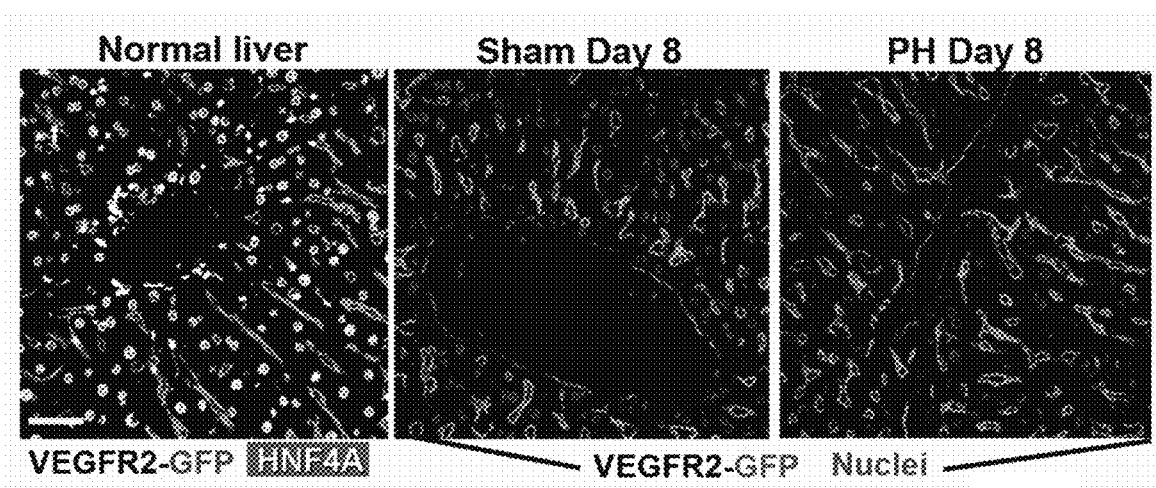
FIG. 2A-G. Phenotypic signature and contribution of LSECs to physiological liver regeneration induced by 70% partial hepatectomy (PH). A, Liver sections obtained from VEGFR2-GFP reporter mice (Hooper, Cell Stem Cell 4:263-274 (2009)). During liver regeneration VEGFR2 is exclusively expressed on the liver endothelial cells. B, Restricted expression of VEGFR3 on LSECs, but not CD34$^+$ large vessels or hepatocytes. C, Polyvariate flow cytometric analysis of the liver non-parenchymal cells. VEGFR2$^+$ cells that are CD45$^-$, express endothelial-specific VE-cadherin. D, Specific expression of VEGFR3 on VEGFR2$^+$VE-cadherin$^+$CD45$^-$ LSECs, with a predominant fraction being CD34$^-$FactorVIII$^+$Prox-1$^-$. Thus LSECs could be identified as VEGFR3$^+$CD34$^-$ cells. E, Forty-eight hours after partial hepatectomy, E-cadherin$^+$P—H3$^+$mitotic hepatocytes are localized adjacent to VE-cadherin$^+$ and VEGFR2$^+$endothelial cells. f, g, Kinetics of LSEC expansion (F) and hepatocyte mitosis (G) during liver regeneration (n=4); hpf, high-power field. Scale bars, 50 µm. Error bars, s.e.m.
Figure 2:
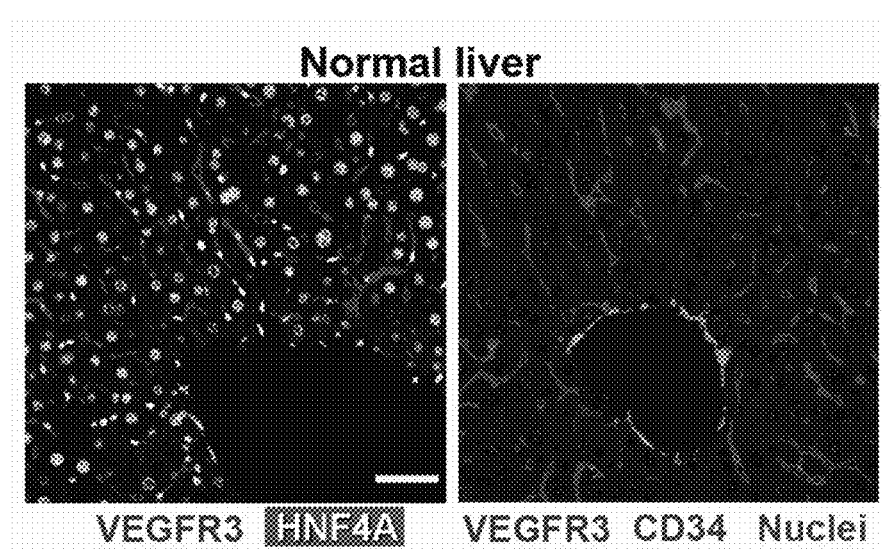

Since the VEGF family plays a role in the regeneration of bone marrow SECs (Hooper, Cell Stem Cell 4:263-274 (2009); Ferrara, Nature Med. 9:669-676 (2003); Carmeliet, Nature 438:932-936 (2005); Alitalo, Nature 438:946-953 (2005), the inventors hypothesized that VEGF receptors, including VEGFR2 or VEGFR3, also modulate LSEC function. Therefore, the inventors used VEGFR2-GFP mice, in which the expression of green fluorescent protein (GFP) is driven by the native promoter of VEGFR2, to demonstrate that VEGFR2 and VEGFR3 are exclusively expressed in the liver endothelial cells. In contrast, the inventors found that VEGFR2 and VEGFR3 are not expressed in other liver cell types, such as hepatocyte nuclear factor 4α $(HNF4A)^+$ hepatocytes (FIG. 2A). Notably, distribution of VEGFR3 expression is restricted to VEGFR2$^+$ LSECs that branch out from CD34$^+$VEGFR3$^-$ large vessels. VEGFR3 expression is not typical of ECs that form the larger vascular system, such as arteries and veins that carry blood around the body. Thus, expression of VEGFR3 in LSECs distinguishes LSECs from ECs that are not organ specific. (FIG. 2B).

Identification of Unique Expression Phenotype of LSECs Allows for Cell-Specific Quantification, Purification and Molecular Profiling The inventors performed polyvariate flow cytometric analysis on non-parenchymal cells (NPCs) to demonstrate the expression of endothelial-specific marker VE-cadherin on non-haematopoietic VEGFR3$^+$VEGFR2$^+$CD45$^-$ LSECs. The inventors found that 97.6% of these cells are Prox1$^-$CD34$^-$ endothelial cells expressing coagulation factor VIII (FIG. 2C, D). Prox1$^-$CD34$^-$ cells are non-lymphatic cells. (Alitalo, Nature 438:946-953 (2005)) This designates a unique phenotypic and operational signature for LSECs of adult mice as VEGFR3$^+$CD34$^-$VEGFR2$^+$VE-cadherin$^+$FactorVIII$^+$Prox-1$^-$CD45$^-$ vessels, distinguishing them from VEGFR3$^-$CD34$^+$VEGFR2$^+$VE-cadherin$^+$CD45$^-$ non-sinusoidal endothelial cells and VEGFR3$^+$CD34$^+$Prox-1$^+$Factor-VIII$^-$CD45$^-$ lymphatic endothelial cells. Identification of LSECs as VEGFR3$^+$CD34$^-$ and non-sinusoidal endothelial cells as VEGFR3$^-$CD34$^+$ is sufficient for quantification, purification and molecular profiling of LSECs from non-sinusoidal ECs.

Identification of Regenerative Interactions Between Hepatocytes and LSECs

To determine the mechanism by which LSECs regulate hepatic proliferation, the inventors tested the regenerative kinetics of hepatocytes and LSECs after partial hepatectomy. The inventors found that, two days after partial hepatectomy, P—H3$^+$E-cadherin$^+$ mitotic hepatocytes were positioned in the proximity of non-proliferating LSECs, as revealed by staining with VE-cadherin, hepatocyte marker epithelial (E)-cadherin and mitotic marker phosphorylated-histone-3 (P—H3; FIG. 2E). This suggests that LSECs release angiogenic growth signals to induce hepatocyte mitosis and proliferation. The inventors found that, following the initial stage of LSEC angiogenic signaling after partial hepatectomy, LSEC proliferation is seen at day 4 and plateaus by day 8 (FIG. 2F). In contrast with LSEC proliferation, the inventors determined that hepatocyte proliferation peaks over the first 4 days, and levels off by day 8, as shown by quantification of P—H3$^+$HNF4A$^+$hepatocytes (FIG. 2G).

These results reveal a chronologically biphasic contribution of LSECs in mediating hepatic reconstitution. At the early phases of partial hepatectomy (days 1-3 after partial hepatectomy), inductive angiogenesis in the non-proliferative LSECs stimulates hepatic regeneration, for example by release of angiocrine factors. After the initial stage of hepatocyte proliferation, in this model 4 days after partial hepatectomy, LSECs proliferate to meet the increased demand of blood supply for the regenerating liver.

Thus, the inventors have determined that, after partial hepatectomy, liver SECs (LSECs) stimulate hepatocyte proliferation through a process of "inductive angiogenesis"; that is, LSECs promote hepatocyte proliferation via angiocrine production of hepatocyte growth factor and Wnt2. The inventors have further determined that, subsequent to this inductive angiogenesis, LSECs themselves undergo "proliferative angiogenesis" to meet the increased demand in blood supply for the regenerating liver tissue.

Activation of VEGF-A/VEGFR2, but not Pl-GF/VEGFR1, is Crucial for Priming LSECs to Initiate and Maintain Hepatic Proliferation To investigate the significance of VEGF receptors during LSEC-driven hepatic regeneration, experiments were designed to delete the VEGFR$^2$ gene conditionally by crossing VEGFR2$^{loxP/loxP}$ mice with ROSA-CreER$^{T2}$ mice, generating inducible VEGFR2-deficient, VEGFR2$^{flox/flox}$ (VEGFR2) mice (FIG. 3J) (Hooper, Cell Stem Cell 4:263-274 (2009)). Owing to the endothelial-cell-specific expression of VEGFR2 in the liver, in VEGFR2$^{fl/fl}$ mice only liver endothelial cells, but not non-endothelial cells, will manifest functional defects. Control mice had heterozygous deletion of the VEGFR2 gene (VEGFR2$^{fl/+}$). Forty-eight hours after partial hepatectomy, bromodeoxyuridine+hepatocyte proliferation (Brd1J+FINF4A+ cell number) was decreased by 67% in VEGFR2$^{fl/fl}$ mice (FIG. 3A, B). Notably, despite the patency of the VE-cadherin+isolectin+ perfused vessels at this early phase, the regeneration of liver mass was attenuated in VEGFR2M mice (FIG. 3C). Therefore, in the early phases (partial hepatectomy days 1-3) of liver regeneration, targeting VEGFR2 primarily impairs the effect of endothelial-derived angiocrine factors to induce hepatocyte regeneration, but not vascular perfusion capacity. Thus, VEGFR2 is important for induction of hepatocyte proliferation in response to angiocrine signals at early stages of liver regeneration.

The inventors further determined that VEGF is also important for proliferative angiogenesis and restoration of normal organ function. The inventors found that, at later stages of liver regeneration (partial hepatectomy days 4-8), proliferative angiogenesis was defective in VEGFR2$^{fl/fl}$ mice (FIG. 3C), interfering with the assembly of patent VE-cadherin+isolectin+ vasculature (FIG. 3D, E), thereby blunting restoration of the liver mass for at least 28 days. Furthermore, in VEGFR2$^{fl/fl}$ mice, liver function after partial hepatectomy was abnormal, as manifested by elevated plasma bilirubin levels. To corroborate the endothelial-specific VEGFR2 function in mediating liver regeneration, VEGFR$^{loxP/loxP}$ mice were also crossed with VE-cadherin-CreER$^{T2}$ mice to induce endothelial-selective deletion of VEGFR$^2$ (FIG. 3K). Both the liver mass and formation of perfused vessels in the VE-cadherin-CreER$^{T2}$VEGFR2$^{fl/fl}$ mice were decreased after partial hepatectomy, which emphasizes the significance of VEGFR$^2$ in mediating liver regeneration.

The inventors postulated that, if the VEGF-A/VEGFR2 pathway promotes the LSEC-driven hepatic regeneration, then VEGF-A should induce or enhance liver regeneration. The inventors found that administration of VEGF-A does promote liver regeneration. The inventors compared the effect of VEGF-A$_{164}$ with placental growth factor (Pl-GF), as the latter selectively activates only VEGFR1 (Carmeliet, Nature 438:932-936 (2005)). After partial hepatectomy, VEGF$_{164}$, but not P1GF, accelerated the regeneration of both liver mass and the number of VEGFR3+CD34− LSECs, which were sustained for at least 28 days (FIG. 3F, G). Therefore, after partial hepatectomy, the activation of VEGF-A/VEGFR2, but not Pl-GF/VEGFR1, is crucial for priming LSECs to initiate and maintain hepatic proliferation.

Activation of the VEGF-A/VEGFR2 Pathway Through Upregulation of Id1 Drives Liver Regeneration Microarray analysis was used to identify the angiocrine signals that stimulate liver regeneration. Among the endothelial-specific genes, the transcription factor Id1 was specifically upregulated in the endothelial cells activated by partial hepatectomy (Lyden, Nature 401:670-677 (1999)). Using Id1$^{venusYFP}$ reporter mice in which the venus-YFP expression is driven by the Id1 promoter (Nam, Cell Stem Cell 5:515-526 (2009)), Id1 upregulation was exclusively found in LSECs 48 h after partial hepatectomy (FIG. 3H), which was significantly blunted in VEGFR2$^{fl/fl}$ mice (FIG. 3I). Remarkably, the liver mass recovery in Id1-deficient (Id1$^{−/−}$) mice after partial hepatectomy was impaired for 28 days and remained unchanged upon VEGF-A$_{164}$ administration (FIG. 4A, J). Furthermore, after partial hepatectomy, Id1$^{−/−}$ mice exhibited significant decrease in mitotic BrdU+ HNF4A+ hepatocyte number, disrupted formation of functional VE-cadherin+isolectin+vessels, diminished proliferation of VEGFR3+CD34− LSECs, and abnormal liver function, as evidenced by an increase in plasma bilirubin levels (FIG. 4B, C, K). Thus activation of the VEGF-A/VEGFR2 pathway through upregulation of Id1 drives liver regeneration.

LSEC-Hepatocyte Co-Culture Reveals Necessity of Id1 for Functional LSEC Induction of Hepatocyte Regeneration The role of Id1 upregulation in mediating the angiocrine function of LSECs on hepatocyte proliferation was also examined by an LSEChepatocyte co-culture system. Co-incubation of isolated hepatocytes with primary LSECs led to a nine-fold increase in hepatocyte number, which was selectively abolished by knockdown of Id1 in LSECs (FIG. 4D, E). Conditioned medium from LSECs failed to support hepatocyte growth, underlining the importance of cell-cell contact in LSEC-derived angiocrine function. Therefore lack of Id1 results in defective inductive function of LSECs, impairing hepatocyte regeneration.

Transplantation of Id1$^{+/+}$ LSECs Restores Liver Regeneration in Id1$^{−/−}$ Liver To determine whether in vivo angiocrine effects of Id1$^{−/−}$ LSECs could initiate hepatocyte regeneration in Id1$^{−/−}$ mice, an intrasplenic transplantation approach was used on day 2 after partial hepatectomy to engraft LSECs into the Id1$^{−/−}$ liver vasculature (FIG. 4F) (Follenzi, J. Clin. Invest:118, 935-945 (2008)). GFP-marked Id1$^{−/−}$ LSECs selectively incorporated into the VEGFR3+ sinusoidal vascular lumen and restored the regeneration of −/− liver mass and LSEC expansion (FIG. 4G). In contrast, the transplanted Id1 LSECs failed to restore the regeneration of the Id1$^{−/−}$ liver. Moreover, in the Id1$^{−/−}$ liver, transplantation of GFP+Id1$^{+/+}$ LSECs at day 2 after partial hepatectomy initiated the proliferation of the hepatocytes in their immediate proximity (FIG. 4H, I). Thus partial vascular chimaerism afforded by the incorporation of Id1-competent LSECs generates sufficient endothelial-cell-derived inductive signals to initiate hepatic proliferation in the Id1$^{−/−}$ liver.

Figure 5:
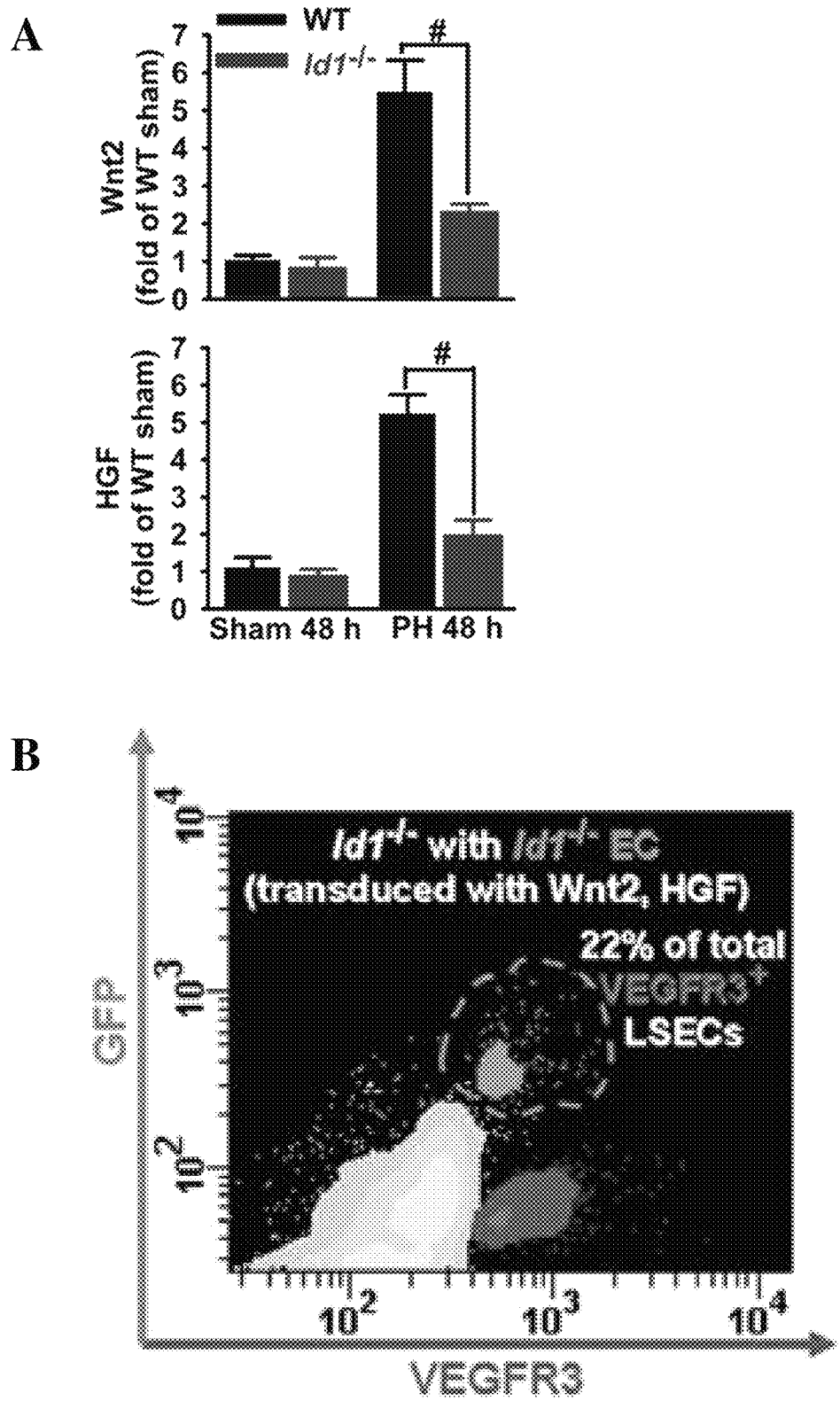
FIG. 5A-G. Id1-mediated induction of Wnt2 and HGF in LSECs stimulates hepatic regeneration. A, Upregulation of HGF and Wnt2 is impaired in Id1$^{-/-}$ LSECs after partial hepatectomy (n=5). B, Intrasplenic transplantation of GFP-marked Id1$^{-/-}$ LSECs carrying both Wnt2 and HGF (Id1$^{-/-}$Wnt2$^+$HGF$^+$GFP$^+$) rescues the regeneration of Id1$^{-/-}$ liver mass (n=4). C, Transplantation of Id1$^{-/-}$ Wnt2$^+$HGF$^+$ LSECs restores the impaired hepatocyte proliferation in the Id1$^{-/-}$ liver (n=4). D, R3+ cells were identified in the livers of Id1$^{-/-}$ mice. E, Requirement for VEGFR2-Id1 pathway in LSEC-mediated liver regeneration. Intrasplenic transplantation of Id1$^{+/+}$ LSECs into the Id1$^{-/-}$ liver sinusoids restores hepatic-vascular regeneration. F, Transplanted Id1$^{+/+}$or Id1$^{-/-}$ Wnt2$^+$HGF$^+$GFP$^+$ LSECs localize to the vicinity of hepatocytes, promoting inductive and proliferative angiogenesis thereby sustaining physiological liver regeneration. *P<0.05; **P<0.01. Scale bar, 20 μm. Error bars, s.e.m. G, Inductive angiogenic LSECs initiate and sustain the regeneration of proximal hepatocytes, through the elaboration of specific angiocrine signals.

Id1 Upregulation in LSECs Initiates Hepatocyte Proliferation Through Inducing Wnt2 and HGF Expression LSECs purified from the wild-type and Id1$^{−/−}$ mice 48 h after partial hepatectomy were analyzed to identify endothelial-derived angiocrine factors that induce liver regeneration. Among the known hepatic trophogens (Klein, Hepatology 47:1018-1031 (2008); Huh, Proc. Natl. Acad. Sci. USA 101:4477-4482 (2004); Goessling, Cell 136:1136-1147 (2009); Ober, Nature 442:688-691 (2006); Thompson, Hepatology 45:1298-1305 (2007), the expression of Wnt2 and HGF, but not other trophogens expressed by LSECs, such as Wnt9B and thrombomodulin, were drastically diminished in Id1$^{−/−}$ LSECs (FIG. 5A). These results suggested to the inventors that Id1 upregulation in LSECs initiates hepatocyte proliferation through inducing Wnt2 and HGF expression.

Intrasplenic Transplantation of LSECs Induces Liver Regeneration Following Hepatectomy Through Id1/Wnt2/HGF To test the effect of Id1 and Wnt2/HGF signaling on liver regeneration, Id1$^{−/−}$ LSECs transduced with Wnt2, HGF or both were engrafted into the Id1$^{−/−}$ liver vasculature by intrasplenic transplantation on day 2 after partial hepatectomy. Only Id1$^{−/−}$ LSECs carrying both Wnt2 and HGF (Id1$^{−/−}$ Wnt2+HGF+) restored the regeneration of mass and LS EC expansion in the Id1$^{−/−}$ nver (FIG. 5B), which suggests a collaborative effect between HGF and Wnt2. Notably, transplantation of either Id1$^{−/−}$ Wnt2+HGF+ LSECs or Id1$^{+/+}$ LSECs into Id1$^{−/−}$ mice increased the mitotic BrdU+HNF4A+ hepatocyte number to a high degree (FIG. 5C). Mitotic hepatocytes were found positioned adjacent to the transplanted Id1$^{−/−}$ Wnt2+HGF+GFP+ LSECs. Therefore Id1-activated LSECs induce proliferation of juxtaposed hepatocytes through elaboration of Wnt2 and HGF (FIG. 5E).

Thus, the use of conditional VEGFR2 knockout, Id1$^{-/-}$ mice, and endothelial cell transplantation has demonstrated the essential angiocrine role of a specialized organ-specific vascular niche cell, defined operationally as VEGFR3$^+$CD34$^-$VEGFR2$^+$VE-cadherin$^+$FactorVIII$^+$Prox1$^-$CD45$^-$ LSECs, in orchestrating physiological liver regeneration induced by partial hepatectomy. Similar to upregulation of Id1 in the angiogenic tumour vessels (Lyden, Nature 401: 670-677 (1999)), Id1 expression is minimal in the normal LSECs, but after partial hepatectomy, activation of VEGFR2 induces exclusive upregulation of Id1 in the angiogenic LSECs.

It has been further demonstrated that in the first 3 days after partial hepatectomy, activation of the VEGFR2-Id1 pathway switches on an inductive angiogenesis program in non-proliferative VEGFR3$^+$CD34$^-$VEGFR2$^+$Id1$^+$ LSECs, which, through production of angiocrine factors Wnt2 and HGF, provokes hepatic proliferation. Subsequently, as the regenerating liver demands additional blood supply, VEGFR2-Id1-mediated proliferative angiogenesis of LSECs reconstitutes hepatovascular mass. Without being bound by theory, this data suggests that LSECs support liver regeneration through a biphasic mechanism: at the early phase immediately after partial hepatectomy, inductive angiogenic LSECs promote organogenesis through release of angiocrine factors, whereas proliferative angiogenic LSECs vascularize and sustain the expanding liver mass.

These studies show that transplantation of the Id1$^{-/-}$ Wnt2$^+$HGF$^+$ LSECs into Id1$^{-/-}$ mice induces and enhances liver regeneration. This finding, and the observation that hepatic proliferation is severely blunted in the VEGFR2 and Id1-deficient mice, shows that LSECs are chartered with the responsibility of establishing an inductive vascular niche to initiate hepatic proliferation by elaborating angiocrine factors. Further, endothelial progenitor cells (EPCs) derived from non-hepatic tissues can alternatively substitute for LSECs to initiate and restore liver regeneration. Notably, VEGFR2$^+$Id1$^+$ EPCs can initiate angiogenesis through release of angiocrine factors rather than structurally incorporating into the vessel wall. As such, intrahepatic transplantation of EPCs will open up new avenues of cell therapy to promote liver regeneration.

In the partial hepatectomy model used in this study, the vascular integrity of the residual liver lobes is maintained with minimal inflammatory response, thereby establishing an ideal model to study endothelial-dependent liver regeneration. However, in chemically induced liver injury, severe vascular damage and cell death might require the recruitment of other non-endothelial cells, including stellate cells (Friedman, Physiol. Rev. 88:125-172 (2008)) and pro-angiogenic haematopoietic cells, such as CXCR4$^+$VEGFR1$^+$ hemangiocytes (Jin, Nature Med. 12:557-567 (2006)), to support liver regeneration.

The rapid regeneration of the liver after partial hepatectomy requires collective and global proliferation of many hepatocytes. Indeed, as each hepatocyte resides in close proximity to LSECs, this remarkably harmonious activation of hepatocytes is achieved by switching on an angiocrine-dependent regenerative program to induce proliferation of mature hepatocytes throughout the residual liver after partial hepatectomy. Angiocrine factors can also promote the propagation of liver progenitor cells (Zaret, Science 322: 1490-1494 (2008)), in addition to mature hepatocytes.

In this study, Wnt2 and HGF are recognized as liver-specific angiocrine factors driving hepatic regeneration. This invention also provides the presence of other angiocrine factors that can collaborate with Wnt2 and HGF to modulate liver regeneration, for example endothelial-specific extracellular matrix components, proteases, adhesion molecules and chemokines.

This disclosure further provides tissue-specific expression of defined angiocrine factors that can elucidate the specificity of vasculature in regulating developmental and adult organogenesis.

So far, attempts at liver regeneration by hepatocyte transplantation have culminated in limited success (Follenzi, J. Clin. Invest:118, 935-945 (2008)). The studies shown here indicate that co-transplantation of hepatocytes or their progenitor cells (Zaret, Science 322:1490-1494 (2008)) with VEGFR2$^+$Id1$^+$ LSECs or EPCs now allows the design of effective strategies to rescue hepatovascular function in patients inflicted with traumatic or infectious liver damage.

Example 2

Lung Regeneration

Transgenic Reporter and Gene Targeted Animals.

Generation of endothelial-specific Vegfr2 and Fgfr1 inducible knockout mice was carried out as described (Hooper, Cell stem cell 4: 263-274 (2009); Wang, Nature 465:483-486 (2010)). Briefly, Vegfr2$^{loxP/loxP}$ and Fgfr1$^{loxP/loxP}$ mice were bred with VE-cadherin-CreERT2 transgenic mice to establish VE-cadherin-CreERT2$^+$ Vegfr2$^{LoxP/LoxP}$ and VE-cadherin-CreERT2$^+$ Vegfr2$^{loxP/loxP}$Fgfr1$^{loxP/+}$ mice. These mice were treated i.p. with tamoxifen, leading to endothelial-specific deletion of Vegfr2 and Fgfr1.

Mice bearing SPC and CCSP promoter-driven rtTA (SPC-rtTA, CCSP-rtTA) and (tetO)7CMV-driven cre ((tetO)$_7$-cre) (Peri, Proceedings of the National Academy of Sciences of the United States of America 99:10482-10487 (2002)) were crossed with Rosa26R-eYFP mice as described (Rawlins, Cell stem cell 4:525-534 (2009)), resulting in SPC-YFP and CCSP—YFP reporter mice upon tetracycline treatment. All experiments were carried out under guidelines set by Institutional Animal Care and Use Committee.

PNX Model and Physiological Measurements of Lung Mechanics

PNX procedure was adapted as described (Nolen-Walston, Am J Physiol Lung Cell Mol Physiol 294:L1158-1165 (2008)). Briefly, orotracheal intubation was performed in anesthetized and mechanically ventilated mice. Left lung lobe was lifted with a suture tied around the hilum and resected. Sham mice underwent thoracotomy without lobe resection. Lung mass and volume were measured and normalized to body weight after PNX. Isolation of PCECs and examination of phosphorylation and protein level of VEGFR2 and FGFR1 was carried out as described in Example 1, and as in Murakami, The Journal of clinical investigation 121 (2011). Inspiratory capacity was determined between the plateau pressure measurements of the lung capacity (TLC) and functional residual volume (FRC) using the FLEXIVENT software (Scireq). Static compliance was determined from pressurevolume curves.

Immunofluorescence (IF) and Flow Cytometric Analysis

To perform IF studies, cryopreserved sections were incubated in antibodies recognizing VE-cadherin (R&D Systems), CD34 (BD), E-cadherin (eBiosciences), and SPC (Abcam) and fluorophore-conjugated 2nd antibodies (Jackson Immuno Research). Transit cell amplification was measured by BrdU uptake (Ding, Nature 468:310-315 (2010)). To track proliferating BASC-like cells, BrdU was introduced in drinking water (Nolen-Walston, Am J Physiol Lung Cell Mol Physiol 294:L1158-1165 (2008)). Images were captured on AXIOVERT LSM710 microscope (Zeiss). Morphological analysis of alveolar number and mean linear intercept was performed (DeLisser, The Journal of biological chemistry 281:8724-8731 (2006)). Total lung cells were isolated and analyzed on LSRII-SORP (BD Biosciences) (Ding, Nature 468:310-315 (2010)). AECs and PCECs were quantified by staining with conjugated antibodies against SPC+E-cadherin and VE-cadherin+CD34, respectively.

Pharmacological Administration of EGF and Neutralizing mAb to MMP14

Mice were injected with mAb to mouse MMP14 (MMP14 mAb, 50 mg/kg, Abcam) and IgG control 12 hours before PNX and every other day. To determine the role of recombinant EGF in alveolar regeneration, mice were i.v. injected with 500 μg/kg EGF (Abcam) on daily basis after PNX. Mice were also intratracheally injected with 100 μg/kg EGF (in 50 μl) every other day to test the local effect of EGF.

Determination of AECII and BASC Proliferation in Coculture with Primary ECs

To maintain Akt activation, primary ECs were transduced with E4ORF1 gene (Seandel, Proceedings of the National Academy of Sciences of the United States of America, 105:19288-93 (2008)). To co-activate the MAPKinase pathway, c-Raf was introduced into primary E4ORF1$^+$ ECs. The resultant MAPK+Akt ECs Kobayashi, Nature cell biology 12:1046-1056 (2010)) were co-cultured with AECIIs and BASCs isolated from SPC and CCSP-YFP mice (Kim, Cell 121:823-835 (2005)). Mmp14 or scrambled shRNA was used to knockdown Mmp14 in MAPK+Akt ECs or AECs (Ding, Nature 468:310-315 (2010)). For co-culture studies, isolated SPC$^+$ AECIIs and BASCs were plated in nonadherent dish, seeded with 10-fold more MAPK+Akt ECs. Conditioned medium from MAPK+Akt ECs was added to AECs. After coculture, AECIIs and BASCs were quantified by flow cytometric analysis.

qPCR, ELISA, and Immunoblot Analyses

After PNX, total RNA was isolated from the mouse lungs to perform qPCR using Taqman expression systems (Applied Biosystems). HB-EGF concentration in BALF was examined by sandwich ELISA and Western blot using anti-HB-EGF antibodies (Santa Cruz), and cleavage of laminin5 γ2 chain was tested with antibody against γ2 chain (Santa Cruz).

Data Analysis

All data are presented as Mean±sem. Differences between groups were tested for statistical significance using Student's t-test or analysis of variance (ANOVA). Statistical significance was set at $P<0.05$.

PNX Induces Expansion of Epithelial Progenitor Cells

Figure 6:
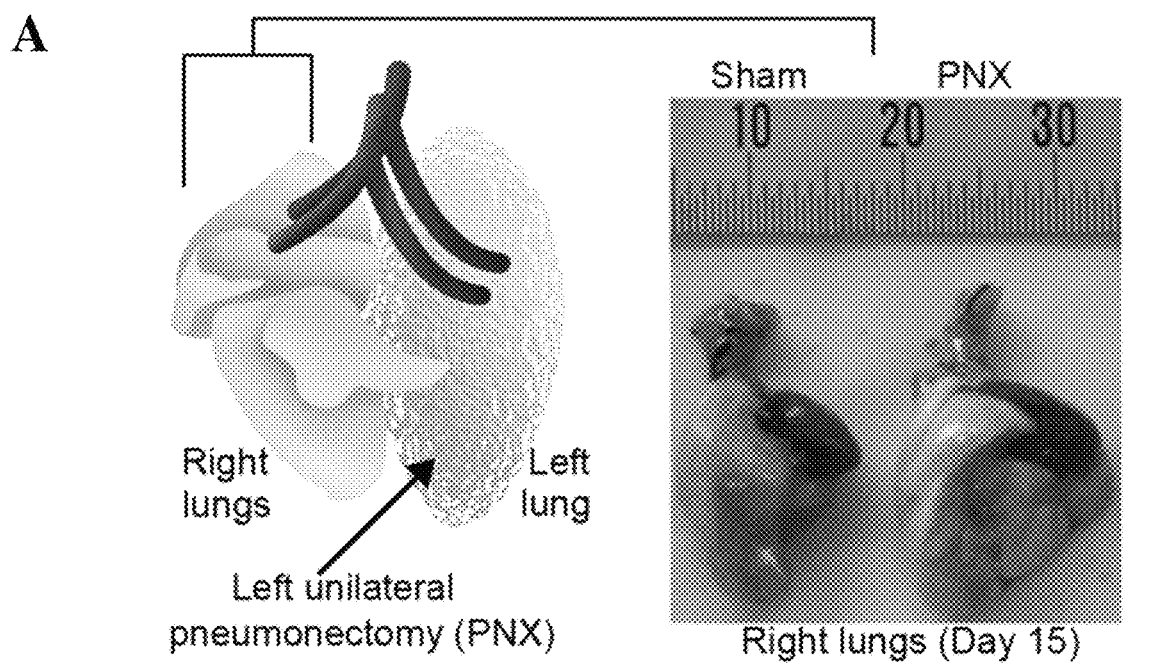
FIG. 6A-E. PNX induces right lung regeneration and expansion of lung epithelial progenitors. (A, B) Restoration of weight and volume in the remaining intact right lung lobes after resection of left lung. A, schema illustrating PNX procedure and representative image of regenerated right lungs 15 days after PNX. B, Lung regeneration is initiated 3 days after PNX and achieves its maximum size and volume at day 15. n=5. C, Amplification of CCSP$^+$ cells at bronchioalveolar duct junction (BADJ) on day 3 after PNX. Mice were fed with BrdU-containing drinking water to pulse proliferating lung progenitors. There is a specific expansion of CCSP$^+$BrdU$^+$ cells localized at BADJ on day 3 after PNX (arrows). Note the distribution of BrdU$^+$ cells in distal alveolar space thereafter (arrowheads). D, E, CCSP$^+$SPC$^+$Sca-1$^+$VE-cadherin CD31 BASC-like cells were identified and quantified in CCSP-YFP and SPC-YFP mice 3 days after PNX. There is minimal BrdU uptake in VE-cadherin$^+$CD31$^+$ PCECs, indicating that at this time point PCECs do not undergo proliferation. Note the close cellular juxtaposition of VE-cadherin$^+$ PCECs (blue arrow) and proliferating CCSP$^+$BrdU$^+$ BASCs (red arrow) in lower inset of D panel.
Figure 6:
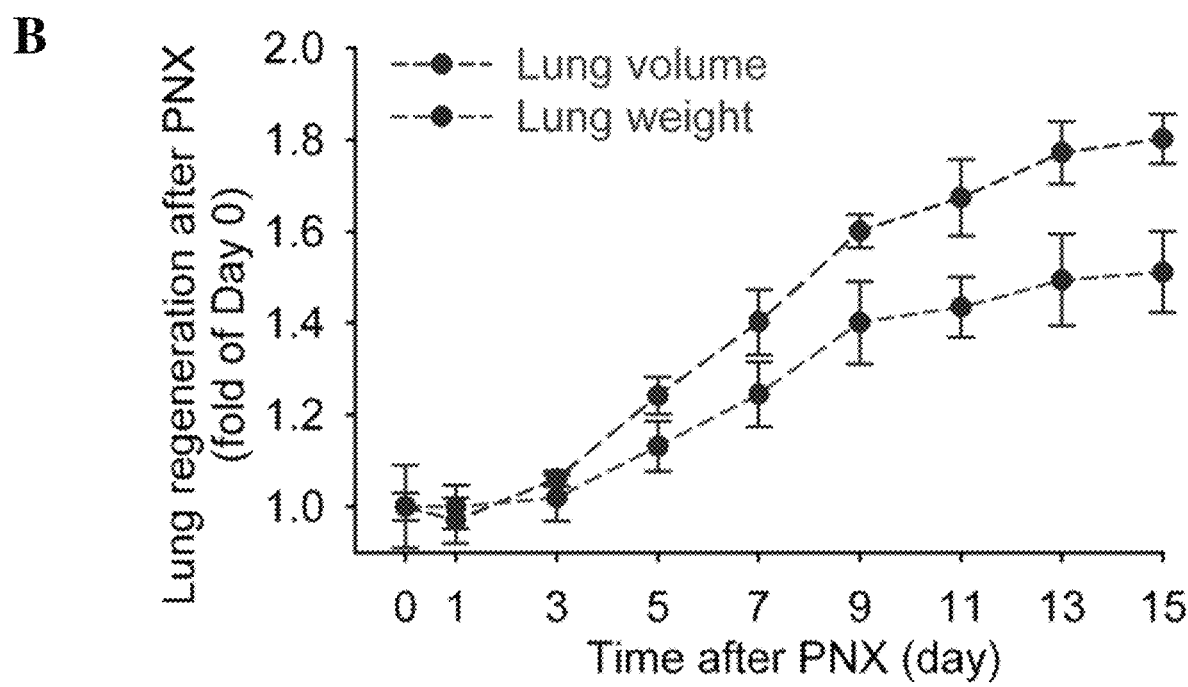

Within 15 days after PNX, there is a dramatic regeneration in the mass and volume of remaining right lung lobes (FIG. 6A, B). Lung epithelial progenitor cells, including subsets of BASCs identified by Clara cell secreted protein (CCSP)$^+$pro-surfactant protein C (SPC)$^+$Sca-1$^+$ (CCSP$^+$SPC$^+$Sca-1$^+$) cells and type II AECs (AECIIs) by SPC$^+$E-cadherin$^+$ cells contribute to alveolar epithelialization (Beers, The Journal of clinical investigation 121: 2065-2073 (2011)). To determine the contribution of epithelial progenitor cells to lung regeneration, after PNX, the inventors introduced BrdU in drinking water to detect slow-cycling cells. On day 3 after PNX, the inventors observed amplification of BrdU$^+$CCSP$^+$ cells at bronchioalveolar duct junction (BADJ) (FIG. 6C). To track expansion of BrdU$^+$CCSP$^+$ cells, the inventors used reporter transgenic mice in which CCSP and SPC promoters drive YFP expression (CCSP-YFP and SPC-YFP mice) (Perl, Proceedings of the National Academy of Sciences of the United States of America 99:10482-10487 (2002)) (FIG. 6D, E). The inventors performed polyvariate flow cytometric analysis of all mononuclear cells in regenerating lungs on day 3 after PNX. The CCSP$^+$BrdU$^+$ cells localized to the BADJ region were CCSP$^+$SPC$^+$Sca-1$^+$VE-cadherin$^-$CD31$^-$ cells, a phenotypic signature observed on BASCs (Kim, Cell 121:823-835 (2005)). At this early time point, the inventors did not detect proliferation of SPC$^+$Sca-1$^-$CCSP$^-$ AECIIs or VE-cadherin$^+$CD31$^+$ PCECs. Therefore, PNX induces expansion of slow cycling CCSP$^+$SPC$^+$Sca-1$^+$ BASC-like cells in early phases of lung regeneration, when there is minimal proliferation of AECs and PCECs.

Figure 7:
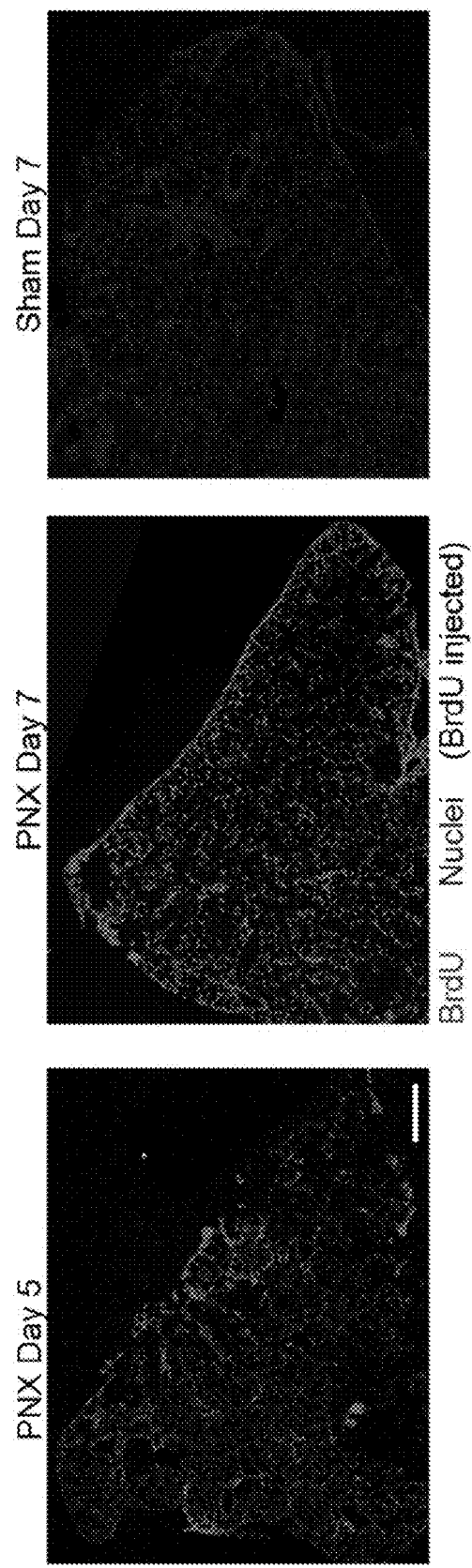
FIG. 7A-E. At day 7 after PNX, expansion of AECs and PCECs sustains alveolar regeneration. A, After PNX, transit amplifying cells (TACs) were pulsed with I.P. administration of BrdU and revealed by BrdU staining. BrdU$^+$ TACs increased throughout the right lungs and peaks at day 7 after PNX. Scale bar, 2.5 mm. B, C, Quantification of TACs in the remaining right lung at day 7 after PNX. Polyvariate flow cytometric analysis of total mononuclear cells demonstrates expansion of SPD$^+$SPC$^+$E-cadherin$^+$ AECIIs and VE-cadherin$^+$CD34$^+$VEGFR2$^+$FGFR1$^+$CD45$^-$ PCECs. D, Proliferation of SPC$^+$ AECIIs and VE-cadherin$^+$ PCECs at the alveolar-capillary interface in the remaining lungs at day 7 after PNX. Note the close cellular proximity between PCECs (green arrow) with BrdU$^+$ AECIIs (red arrow). Scale bar, 100 μm. E, Quantification of VE-cadherin$^+$CD34$^+$ PCECs and SPC$^+$E-cadherin$^+$ AECIIs in the remaining lungs 15 days after PNX; PNX induces proliferation of PCECs and AECs. n=5.

PNX Induces Expansion of PCECs and AECs Co-Localizing at the Alveolar-Capillary Interface To identify time points after PNX when AECs and PCECs undergo significant proliferation, the inventors examined the kinetics of incorporation of intraperitoneally injected BrdU in the remaining lobes and found a global appearance of transit amplifying cells (TACs) that peaked at day 7 after PNX (FIG. 7A). In sham operated mouse lungs, there was little uptake of BrdU. To characterize cell types in TACs on day 7 after PNX, the inventors performed PNX on SPC-YFP reporter mice. There was increased proliferation of SPC$^+$ cells that coexpress pro-surfactant protein D (SPD) and E-cadherin, markers representing AECIIs (Beers, The Journal of biological chemistry 269:20318-20328 (1994); Whitsett, Annual review of medicine 61:105-119 (2010)) (FIG. 7B).

The remaining SPC$^-$ TACs consist of small fraction of CCSP$^+$airway Clara cells (Rawlins, Cell stem cell 4:525-534 (2009)) and VE-cadherin$^+$ PCECs. Analysis of BrdU incorporation showed that on day 7 after PNX, proliferating VE-cadherin$^+$CD34$^+$FGFR1$^+$VEGFR2$^+$CD45$^-$ PCECs accounted for 7% of mononuclear cells (FIG. 7C), which were localized to the vicinity of SPC$^+$ AECIIs (FIG. 7D). Using SPC$^+$E-cadherin$^+$ and VE-cadherin$^+$CD34$^+$ as operational markers for AECIIs and PCECs, respectively, the inventors found that on day 15 after PNX there was a 3-fold increase in the population of both AECIIs and PCECs (FIG. 7E). Therefore, after PNX the increase in lung mass and volume is due to proliferation of PCECs and epithelial progenitor cells, with BASC-like cells expanding at early time points (day 3), while AECIIs proliferating at later time points.

Figure 8:
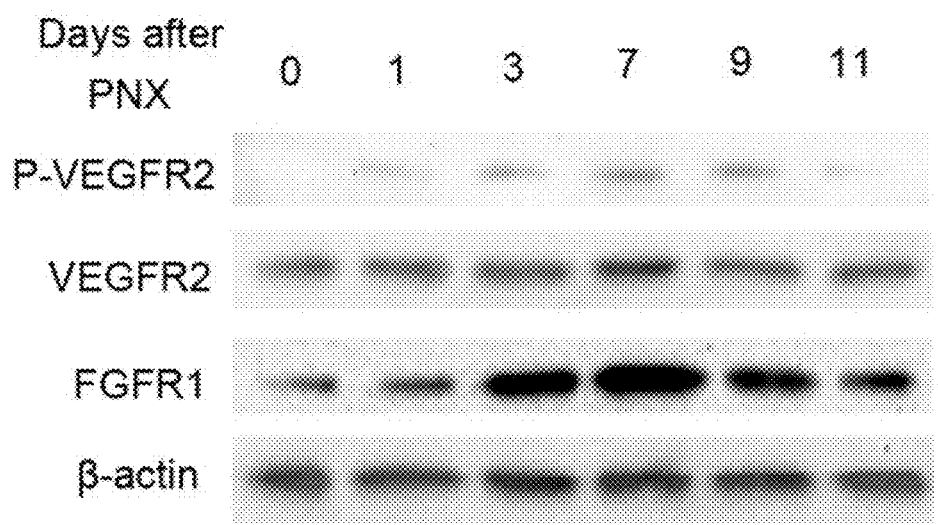
FIG. 8A-G. Inducible deletion of Vegfr2 and partial knockdown of Fgfr1 in ECs attenuates lung regeneration. A, Sequential activation of VEGFR2 and upregulation of FGFR1 in PCECs after PNX. VEGFR2 phosphorylation is increased by PNX, while total VEGFR2 expression in PCECs remains constant. In contrast, FGFR1 expression in PCECs is upregulated after PNX in time-dependent manner. B, EC-specific knockout of VEGFR2 and FGFR1 in adult mice. Transgenic mice in which VE-cadherin promoter drives expression of tamoxifen-responsive CreERT2 (VE-Cad-CreERT2 mice) were crossed with Vegfr2$^{loxP/loxP}$ and Fgfr1$^{loxP/loxP}$ mice and treated with tamoxifen to induce EC-specific deletion of Vegfr2 and Fgfr1 (Vegfr2$^{iΔEC/iΔEC}$ and Vegfr2$^{iΔEC/iΔEC}$Fgfr1$^{iΔEC/+}$ mice). C, EC-specific deletion of Vegfr2 (Vegfr2$^{iΔEC/iΔEC}$ mice) inhibits the expansion of CCSP$^+$Sca1$^+$ BASC-like cells after PNX. Vegfr2$^{iΔEC/+}$ mice served as control. D, E, Defective proliferation of both PCECs (red arrowheads) and AECs (yellow arrows) in Vegfr2$^{iΔEC/iΔEC}$ Fgfr1$^{iΔEC/+}$ mice after PNX, n=4. Scale bar, 100 μm. Note the increase in alveolar diameter (dashed arrows) in Vegfr2$^{iΔEC/iΔEC}$Fgfr1$^{iΔEC/+}$ mice as compared to control Vegfr2$^{iΔEC/+}$ mice. F, After PNX, EC-specific deletion of Vegfr2 and Fgfr1 impaired the recovery of pulmonary function. The restoration of pulmonary function in Vegfr2$^{iΔEC/iΔEC}$Fgfr1$^{iΔEC/+}$ mice was significantly inhibited compared to control mice. Note the normal pulmonary function of knockout mice before PNX. #, p<0.01, compared to control Vegfr2$^{iΔEC/+}$ mice, n=4. G, Restoration of lung mass and volume is impaired in Vegfr2$^{iΔEC/iΔEC}$Fgfr1$^{iΔEC/+}$ mice, n=4.
Figure 8:
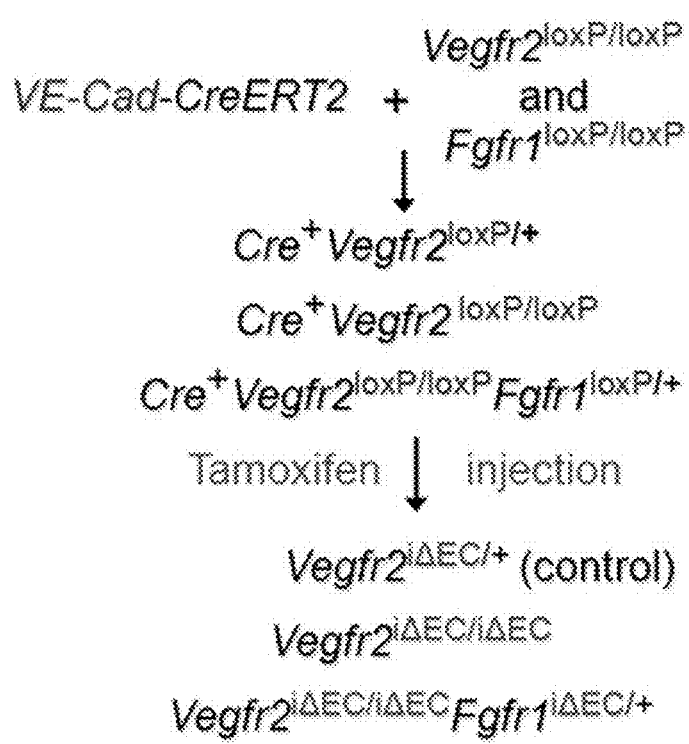

Sequential Activation of VEGFR2 and FGFR1 in PCECs is Essential for Functional Alveolar Regeneration PNX initiates lung regeneration through activation of PCECs to produce epithelial-active angiocrine factors. As VEGFR2, the principal tyrosine kinase receptor of VEGF-A, plays a critical role in induction of angiocrine factors (Ding, Nature 468:310-315 (2010); Hooper, Cell stem cell 4: 263-274 (2009)), the inventors analyzed the activation of VEGFR2 in PCECs after PNX. Although VEGFR2 protein level in PCECs is unaltered, after PNX the extent of phosphorylated VEGFR2 is increased, indicating activation of this VEGF-A receptor in the ECs of regenerating right lobes (FIG. 8A).

Since FGFR1 is expressed in PCECs and can reciprocally modulate the expression and activation state of VEGFR2 (Murakami, The Journal of clinical investigation 121 (2011); White, Development 134:3743-3752 (2007)) to drive angiocrine factor production, the inventors studied the expression of FGFR1 by PCECs. After PNX, FGFR1 protein was upregulated in time-dependent manner. Thus, while in early phases of lung regeneration activation of VEGFR2 in PCECs initiates alveologenesis, at later phases coactivation of FGFR1 might synergize with VEGFR2 to sustain regenerative epithelialization.

To elucidate the endothelial-specific function of VEGFR2 and FGFR1 in the lungs, the inventors employed an inducible knockout strategy to selectively delete the Vegfr2 gene in adult mouse ECs (FIG. 8B), using transgenic mice in which the VE-cadherin promoter drives expression of tamoxifen-responsive Cre (VE-Cad-CreERT2) (Wang, Nature 465:483-486 (2010)). Tamoxifen treatment selectively deletes Vegfr2 in ECs (Vegfr2$^{i\Delta EC/i\Delta EC}$ mice). To account for off-target toxicity by CreERT2, the inventors used heterozygous Vegfr2 deficient (Vegfr2$^{i\Delta EC/+}$) mice as control. The inventors also generated mice in which both Vegfr2 and Fgfr1 were deleted in ECs. However, since these mice could not tolerate surgical procedures because of vascular instability, the inventors investigated the role of coactivation of FGFR1 and VEGFR2 in supporting alveologenesis by inducible Vegfr2 and partial Fgfr1 deletion in ECs (Vegfr2$^{i\Delta EC/i\Delta EC}$Fgfr1$^{i\Delta EC/+}$ mice.

Before PNX, Vegfr2$^{i\Delta EC/i\Delta EC}$ and Vegfr2$^{i\Delta EC/i\Delta EC}$Fgfr1$^{i\Delta EC/+}$ mice did not manifest alterations in lung mass or function. By contrast, on day 3 after PNX, proliferation of CCSP$^+$Sca1$^+$ BASC-like cells was abolished in Vegfr2$^{i\Delta EC/i\Delta EC}$ mice (FIG. 3C), while there was no further inhibition in expansion of these cells in Vegfr2$^{i\Delta EC/i\Delta EC}$Fgfr1$^{i\Delta EC/+}$ mice after PNX. These data establish the critical role of VEGFR2 activation in supporting epithelialization at early phases of lung regeneration.

The inventors then studied the role of VEGFR2 and FGFR1 coactivation in amplification of PCECs and AECIIs. Costaining of regenerating lungs with BrdU, VE-cadherin, and SPC at day 7 indicated that endothelial-specific knockdown of Vegfr2 in mice (Vegfr2$^{i\Delta EC/i\Delta EC}$) abrogated propagation of both PCECs and AECIIs (FIG. 8D, E). Notably, endothelial-specific knockdown of Vegfr2 and Fgfr1 (Vegfr2$^{i\Delta EC/i\Delta EC}$Fgfr$^{i\Delta EC/+}$) further abolished proliferation of PCECs and AECIIs at this time point, suggesting that FGFR1 synergizes with VEGFR2 in stimulating PCECs to support AECII amplification and neoangiogenesis.

Deletion of Vegfr2 & Fgfr1 in PCECs Impairs Restoration of Alveolar Structure and Function To determine whether coactivation of VEGFR2 and FGFR1 plays a role in improving lung function, the inventors examined inspiratory volume and static compliance in Vegfr2$^{i\Delta EC/i\Delta EC}$Fgfr1$^{i\Delta EC/+}$ and control mice before and after PNX. These parameters of pulmonary function provide physiologically relevant indices of respiratory capacity. The restoration of pulmonary function after PNX was significantly impaired in Vegfr2$^{i\Delta EC/i\Delta EC}$Fgfr1$^{i\Delta EC/+}$ mice at a time point when control mice exhibited complete recovery (FIG. 8F). Similarly, restoration of lung mass, volume, and cell expansion after PNX were all impaired in Vegfr2$^{i\Delta EC/i\Delta EC}$Fgfr$^{i\Delta EC/+}$ mice (FIG. 8G). These data indicate that after PNX, nonproliferating VE-cadherin$^+$ ECs induce early expansion of BASC-like cells via VEGFR2 activation. At later phases after PNX, upregulation of FGFR1 in conjunction with VEGFR2 activates PCECs to instruct epithelialization as well as vascular sprouting, restoring respiratory capacity (FIG. 1B). Thus, PCECs produce angiocrine factors and participate in angiogenesis fostering generation of functional respiratory alveolar units.

Figure 9:
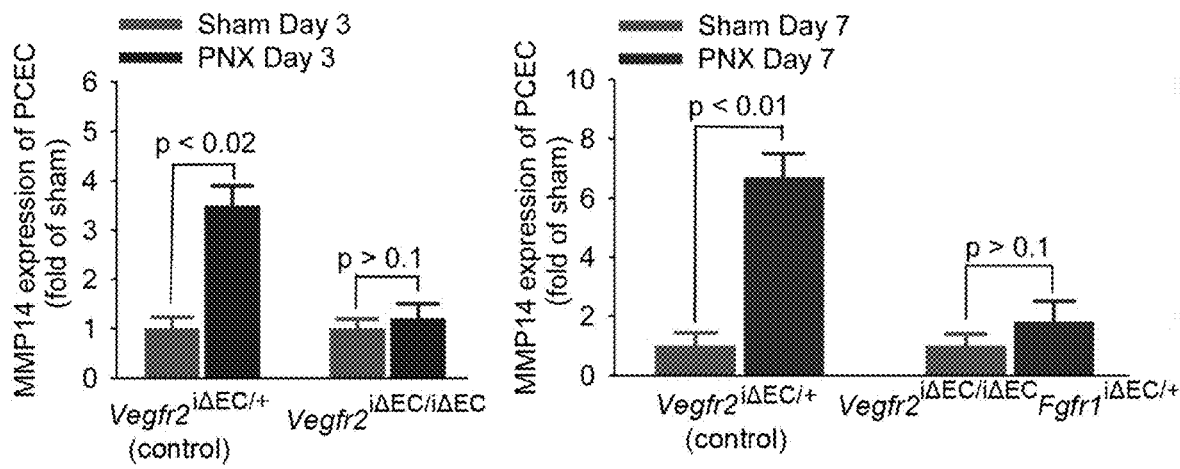
FIG. 9A-E. After PNX, MMP14 is specifically produced by PCECs and induces expansion of SPC AECIIs and CCSP$^+$Sca$^1$$^+$CD31 BASCs. A, Endothelial-specific ablation of Vegfr2 and Fgfr1 diminished the upregulation of MMP14 in pulmonary capillary endothelial cells (PCECs) after PNX. PCECs were isolated from the regenerating mouse lung after PNX, as previously described (Ackah, The Journal of clinical investigation 115:2119-2127 (2005); Murakami, The Journal of clinical investigation 121 (2011)). The upregulation of MMP14 expression relative of sham mice were compared between control and Vegfr2$^{iΔEC/iΔEC}$ (left) or Vegfr2$^{iΔEC/iΔEC}$Fgfr1$^{iΔEC/+}$ (right) mice at day 3 and 7, respectively. Data are presented as mean±s.e.m throughout; n=4. B, Selective activation of VEGFR2 (phosphorylation)
Figure 9:
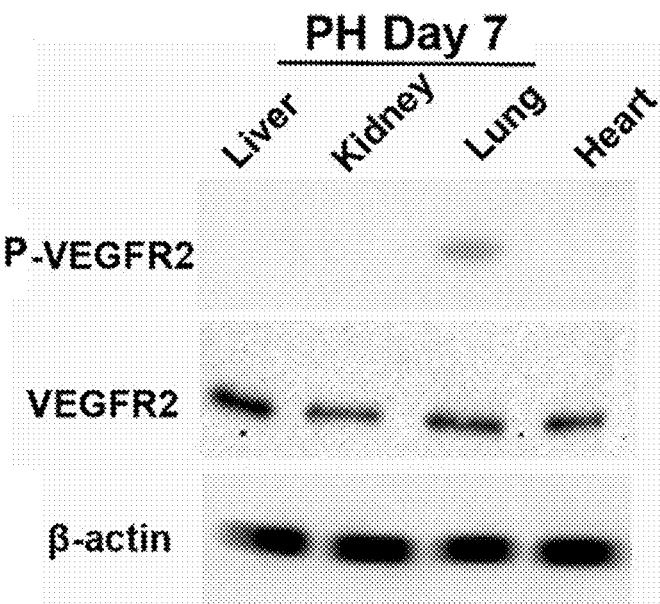
Figure 10:
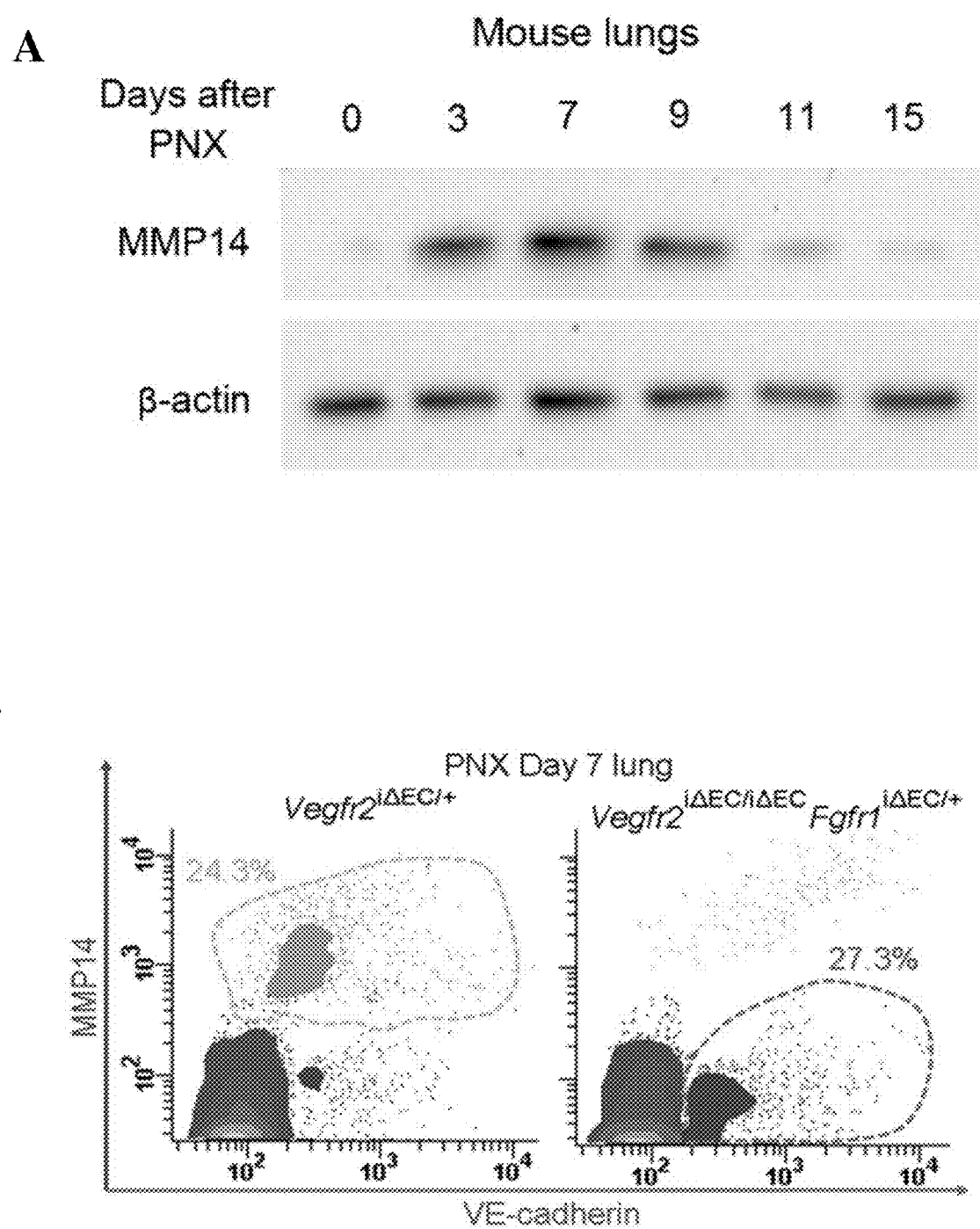

PNX Induces Specific Upregulation of MMP14 in PCECs Expanding Epithelial Progenitor Cells To identify the inductive angiocrine cue that initiates epithelialization, the inventors compared the gene expression profiles of the regenerative lungs, and found that among alveologenic factors, membrane-type 1 matrix metalloproteinase (MMP14) was specifically upregulated in PCECs of wild-type, but not Vegfr2$^{i\Delta EC/i\Delta EC}$ or Vegfr2$^{i\Delta EC/i\Delta EC}$Fgfr1$^{i\Delta EC/+}$ mice (FIG. 9A). Analysis of MMP14 protein level in the pneumonectomized lungs revealed its temporal upregulation that peaks at day 7 and levels off afterwards (FIG. 10A). Immunostaining and flow cytometric analysis illustrated the PCEC-specific localization of MMP14 after PNX, which was diminished in the Vegfr2$^{i\Delta EC/i\Delta EC}$Fgfr1$^{i\Delta EC/+}$ lungs (FIG. 10B, C). MMP14 was not upregulated in other vascular rich organs, including liver, heart, spleen and kidney (FIG. 9B, C), indicating that after PNX MMP14 is selectively upregulated in VEGFR2 and FGFR1 inductive PCECs.

To define the mechanism by which angiocrine expression of MMP14 promotes the propagation of epithelial progenitor cells, the inventors isolated AECIIs and BASCs from SPC-YFP and CCSP-YFP mice, respectively, and cocultured with primary ECs. YFP expression was utilized to track their fate during coculture. The E4ORF1 gene, which through activation of the Akt pathway maintains angiocrine capacity, was introduced into primary ECs (Seandel, Proceedings of the National Academy of Sciences of the United States of America, 105:19288-93 (2008), Kobayashi, Nature cell biology 12:1046-1056 (2010)). Since MMP14 was upregulated in MAP-kinase activated ECs, the inventors also introduced c-Raf to constitutively stimulate MAP-kinase in E40RF1$^+$ ECs (MAPK+Akt ECs) (Kobayashi, Nature cell biology 12:1046-1056 (2010)). Next, MAPK+Akt ECs were cocultured with AECIIs/BASCs in 3-dimensional (3D) angiosphere assay. Coculture with MAPK+Akt ECs led to the most significant expansion of SPC$^+$ AECIIs and CCSP$^+$Sca-1$^+$CD31$^-$ BASCs (FIG. 10D-G, FIG. 9D, E), resulting in formation of 3D angiospheres, with ECs encircling expanding epithelial cells, that resemble the structure of an alveolar-capillary sac. MMP14 knockdown in MAPK+Akt ECs abolished expansion of BACSs and AECIIs (FIG. 10D, F). Conditioned medium (CM) from MAPK+Akt ECs showed a negligible effect in promoting AECII and BASC propagation, underscoring the requirement for cell-cell contact between ECs and epithelial cells (FIG. 10E, G). Therefore, resection of the left lung activates VEGFR2 and FGFR1 on PCECs triggering MMP14 production, which in turn stimulates propagation of epithelial progenitor cells.

After PNX, MMP14 Inhibition Abrogates the Reconstitution of AECs, but not PCECs

Figure 11:
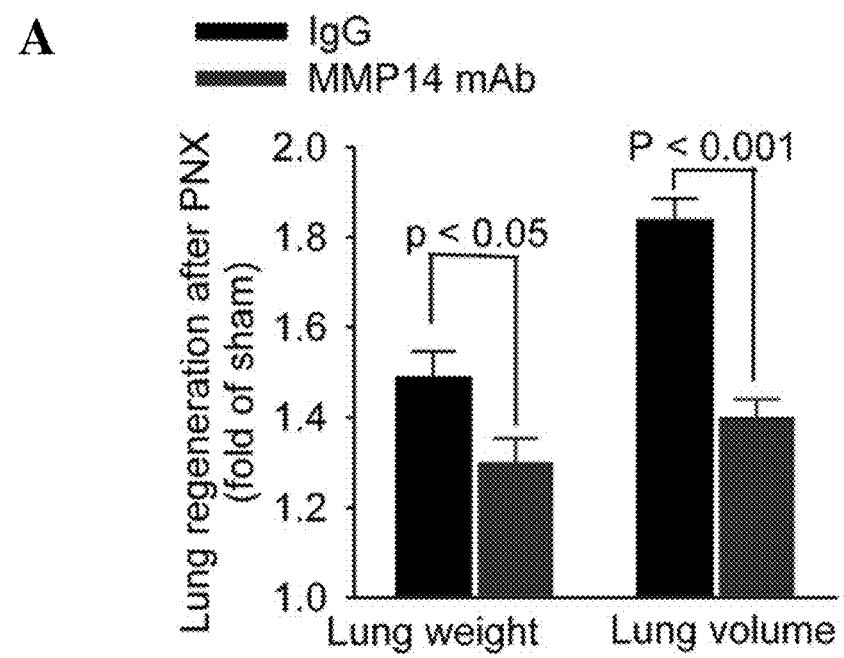
Figure 11:
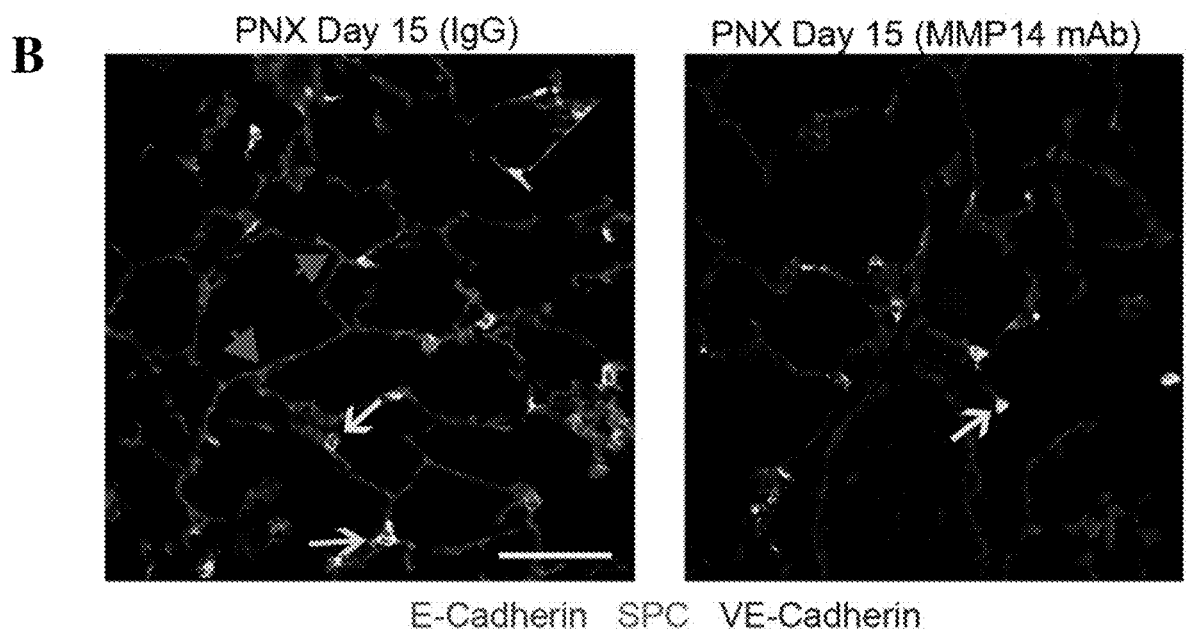

To determine the physiological significance of MMP14 in modulating alveologenesis, the inventors injected WT mice with a neutralizing monoclonal antibody (mAb) to MMP14. After PNX, the MMP14 mAb attenuated the increase of mass and volume of remaining lungs in WT but not Vegfr2$^{i\Delta EC/i\Delta EC}$Fgfr1$^{i\Delta EC/+}$ mice, indicating that MMP14 is derived from VEGFR2 and FGFR1 inductive PCECs (FIG. 11A). MMP14 inhibition blocked expansion of E-cadherin$^+$ AECs without impairing reconstitution of VE-cadherin$^+$ PCECs (FIG. 11B). The mismatched expansion of AECs and PCECs after MMP14 inhibition indicates that MMP14 induces propagation of AECs (inductive angiogenesis), rather than promoting PCEC proliferation (proliferative angiogenesis).

The reduced expansion of AECs, but not PCECs, by MMP14 neutralization was further demonstrated by flow cytometric analysis (FIG. 11C, D). Furthermore, in mice injected with mAb to MMP14, morphological examination revealed inhibition of alveolar regrowth, as evidenced by a decrease in alveolar number and increase in alveolar size measured by mean alveolar intercept (FIG. 11E, F). Collagen synthesis remained unchanged in mice injected with mAb to MMP14. Therefore, PCEC-derived MMP14 stimulates neoalveolarization, forming alveolar sacs reminiscent of normal adult alveoli.

MMP14 Stimulates Alveologenesis Via Unmasking of Cryptic EGF-Like Ligands

Figure 12:
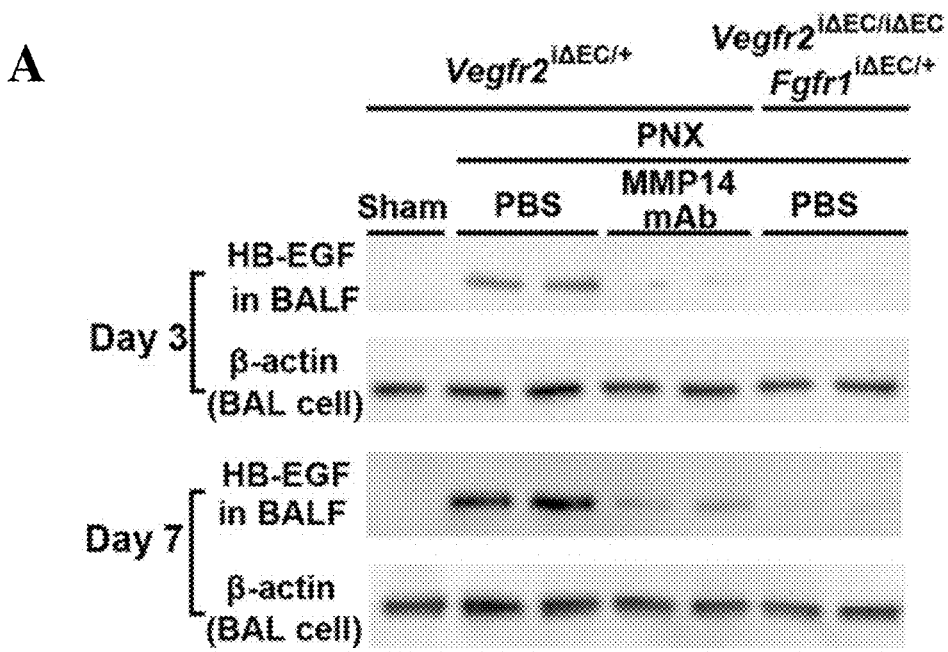
Figure 12:
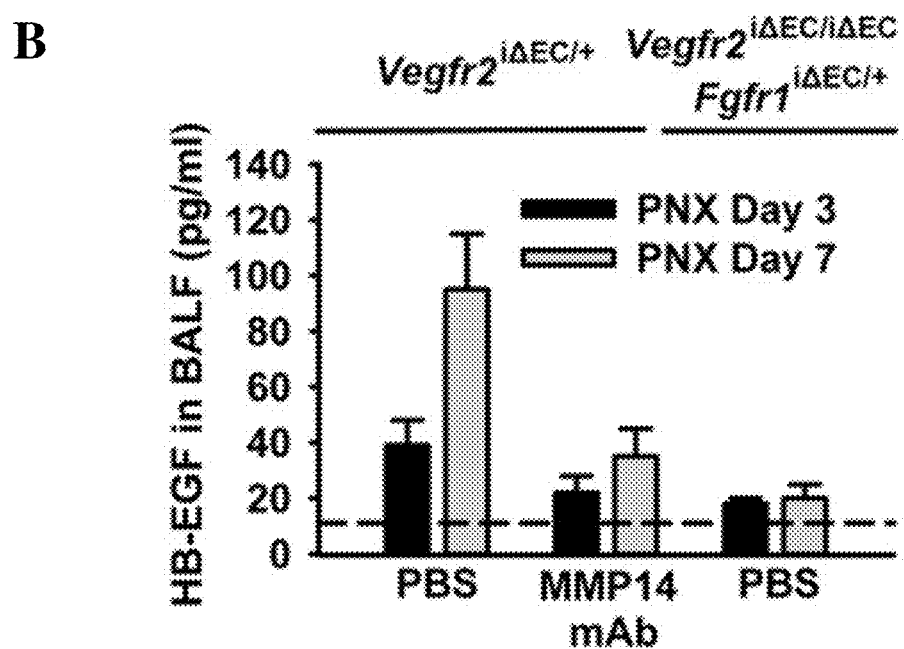

The inventors next sought to unravel the mechanism by which MMP14 regulates regenerative alveolarization. MMP14 has been shown to shed the ectodomain of heparin binding EGF-like growth factor (HB-EGF) (Koshikawa, Cancer research 70:6093-6103 (2010); Stratman, Blood 116:4720-4730 (2011)). In addition, MMP14 cleaves laminin5 γ2 chain to generate an EGF-like fragment that activates EGF receptor (EGFR) (Schenk, The Journal of cell biology 161:197-209 (2003)). The inventors found that at day 3 and 7 after PNX, HB-EGF in bronchioalveolar lavage fluid (BALF) is increased (FIG. 12A, B). The cleaved fragment of laminin5 γ2 chain appeared in regenerating lungs at day 7 after PNX (FIG. 12C). However, the level of these EGFR ligands was decreased in both control mice treated with mAb to MMP14 and Vegfr2$^{iΔEC/iΔEC}$Fgfr1$^{iΔEC/+}$ mice, 1 in which there is diminished expression of MMP14. Knockdown of MMP14 in MAPK+Akt ECs in 3D endothelial coculture with BASCs and AECs also abrogated the release of EGFR ligands to culture supernatant (FIG. 12J). Hence, after PNX, activation of VEGFR2 and FGFR1 in PCECs leads to angiocrine production of MMP14, which in turn unmasks cryptic EGFR ligands stimulating alveolar regeneration.

EGF Restores Alveologenesis in Vegfr2$^{iΔEC/iΔEC}$Fgfr1$^{iΔEC/+}$ Mice

Both shed HB-EGF and cleaved laminin5 γ2 chain activate EGFR that drives epithelialization. These findings suggest that after PNX, impaired lung alveolarization in Vegfr2$^{iΔEC/iΔEC}$Fgfr1$^{iΔEC/+}$ mice is due to decrease in bioavailability of EGFR ligands, implicating that injection of EGF might restore alveolarization in Vegfr2$^{iΔEC/iΔEC}$Fgfr1$^{iΔEC/+}$ mice by enhancing epithelialization. Intravenous injection of recombinant EGF restored lung mass and volume in Vegfr2$^{iΔEC/iΔEC}$Fgfr1$^{iΔEC/+}$ mice and mice treated with mAb to MMP14 (FIG. 12D). Direct introduction of EGF to bronchioalveolar epithelium via intratracheal injection showed similar effect in rescuing alveolar regeneration (FIG. 12K). Therefore, the defective regeneration of AECs in Vegfr2$^{iΔEC/iΔEC}$Fgfr1$^{iΔEC/+}$ mice is caused by diminished MMP14 production by PCECs that attenuates bioavailability of EGFR ligands.

Notably, in Vegfr2$^{iΔEC/iΔEC}$Fgfr1$^{iΔEC/+}$ mice injected with EGF, cellular association of E-cadherin$^+$ AECs with VE-cadherin$^+$ PCECs was enhanced (FIG. 12E), restoring pulmonary function (FIG. 12F). EGF injection into Vegfr2$^{iΔEC/iΔEC}$Fgfr1$^{iΔEC/+}$ mice stimulated regeneration of AECs, but not PCECs, suggesting that EGF has a minor effect in triggering angiogenesis, while being more effective in driving epithelialization. To test this hypothesis, the inventors analyzed the effect of EGF administration on cell amplification at day 7 after PNX. Injection of EGF led to enhanced EGFR phosphorylation in the Vegfr2$^{iΔEC/iΔEC}$Fgfr1$^{iΔEC/+}$ lung (FIG. 12G). BrdU incorporation analysis revealed that EGF restored proliferation of AECIIs, but not PCECs in Vegfr2$^{iΔEC/iΔEC}$Fgfr1$^{iΔEC/+}$ mice (FIG. 12H, I). Thus, the alveologenic defect in Vegfr2$^{iΔEC/iΔEC}$Fgfr1$^{iΔEC/+}$ mice is due to impaired generation of epithelially-active angiocrine factors, rather than compromised vascular perfusion to regenerating lung.

Figure 13:
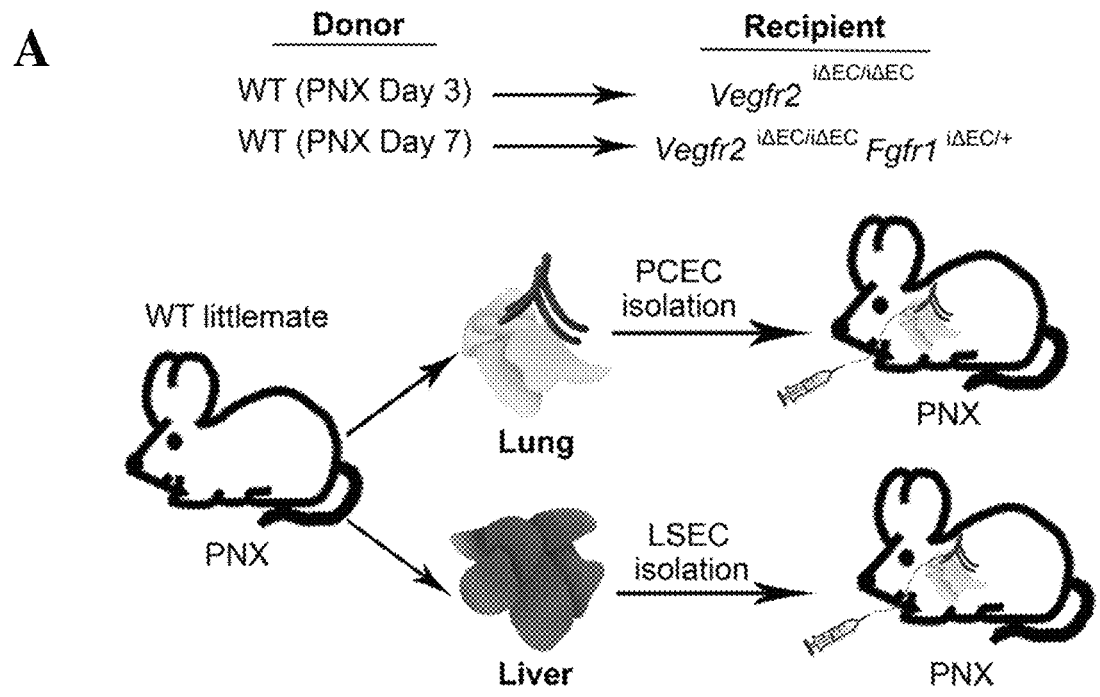
Figure 13:
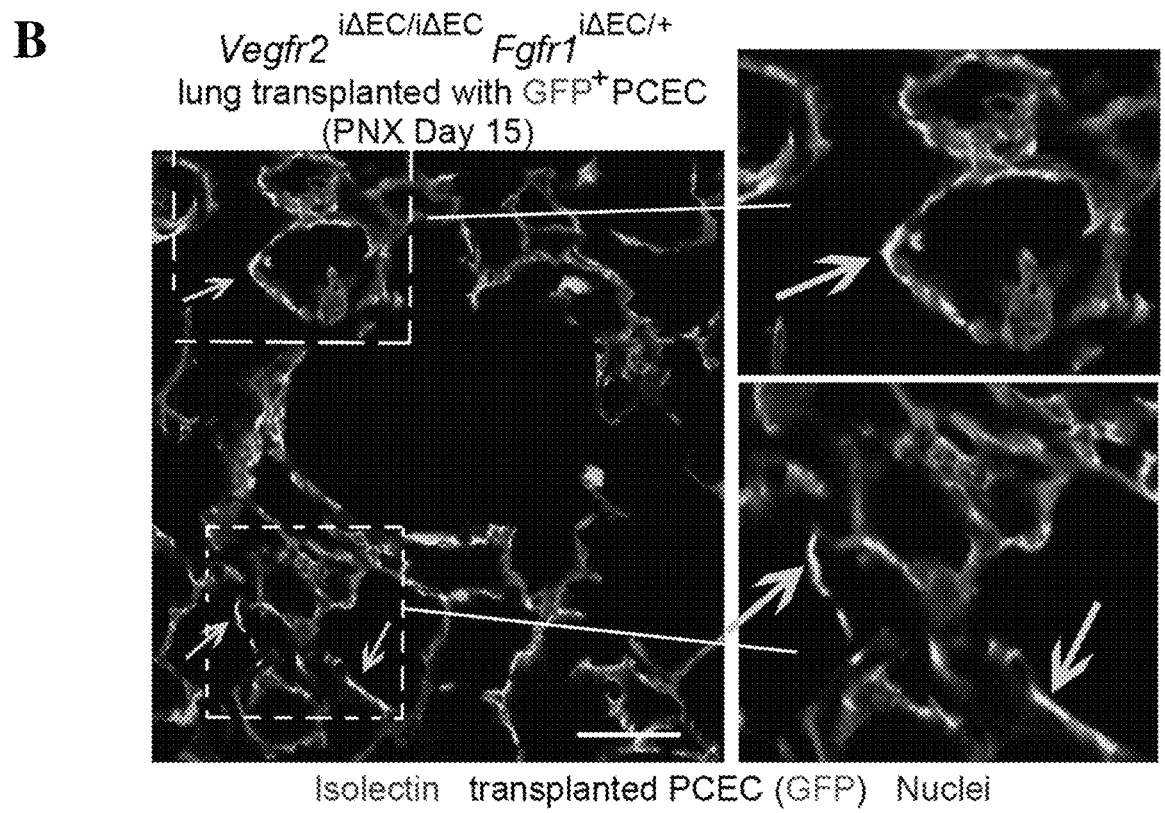

Transplantation of WT PCECs restores Alveolarization in Vegfr2$^{iΔEC/iΔEC}$Fgfr1$^{iΔEC/+}$ mice Pan-endothelial VE-cadherin promoter-driven expression of CreERT2 could delete Vegfr2 and Fgfr1 in ECs of other vascular beds. To investigate the specific contribution of inductive PCECs to lung regeneration, the inventors designed a lung EC transplantation model. ECs were purified from either lung or liver of pneumonectomized WT littermate mice and infused into the jugular vein of Vegfr2$^{iΔEC/iΔEC}$ and Vegfr2$^{iΔEC/iΔEC}$Fgfr1$^{iΔEC/+}$ mice (FIG. 13A). Plasma was also collected from pneumonectomized WT mice and injected to recipient knockout mice to interrogate the contribution of systemic soluble growth factors to lung regeneration.

Transplanted GFP$^+$ ECs were incorporated into 26% of pulmonary capillaries of recipient mice (FIG. 13B). Importantly, the engrafted ECs obtained from the pneumonectomized lungs, but not the liver, restored the amplification of epithelial cells (FIG. 13C-F). Proliferating BrdU$^+$CCSP$^+$ BASC-like cells and BrdU$^+$SPC$^+$ AECIIs were positioned in the proximity of the transplanted GFP$^+$ PCECs, indicating that inductive signals derived from the infused WT PCECs restore lung regeneration. Accordingly, pulmonary function was improved by transplantation of PCECs but not injection of plasma procured from pneumonectomized WT mice (FIG. 13G). Therefore, PNX induces a lung-specific activation of PCECs to elaborate angiocrine factors that support regenerative lung alveolarization (FIG. 13H).

Pneumonectomy Model System and Results

To identify pathways involved in adult lung regeneration, the inventors employed a unilateral pneumonectomy (PNX) model that promotes regenerative alveolarization in the remaining intact lung. The inventors employed a unilateral pneumonectomy (PNX) model to investigate the role of PCECs in supporting alveolar regeneration. Surgical resection of the left lung, which does not perturb the vascular integrity of the remaining right lobes, induces regrowth of these residual lobes. The inventors have determined that PNX, through activation of VEGFR2 and FGFR1, induces PCECs of the remaining right lobes to produce the angiocrine matrix metalloprotease MMP14. In turn, MMP14 promotes regenerative alveolarization by unmasking cryptic epidermal growth factor (EGF)-like ligands which stimulate proliferation of epithelial progenitor cells. Thus, PCECs can be therapeutically exploited for the treatment of lung disorders.

These studies demonstrate that PNX stimulates pulmonary capillary endothelial cells (PCECs) to produce angiocrine growth factors that induce proliferation of epithelial progenitor cells supporting alveologenesis. Further, endothelial cells through MMP14 expression fostered epithelial proliferation forming 3 Dimensional angiospheres, reminiscent of alveolar-capillary sacs. After PNX, endothelial-specific inducible genetic ablation of Vegfr2 and Fgfr1 in mice inhibits production of MMP14, impairing alveolarization. MMP14 promotes expansion of epithelial progenitor cells by unmasking cryptic EGF-like ectodomains that activate the EGF-receptor (EGFR). Consistent with this, neutralization of MMP14 impairs EGFR-mediated alveolar regeneration, while administration of EGF or intravascular transplantation of MMP14$^+$ PCECs into pneumonectomized Vegfr2/Fgfr1 deficient mice restores alveologenesis and lung inspiratory volume and compliance function. VEGFR2 and FGFR1 activation in PCECs therefore increases MMP14-dependent bioavailability of EGFR ligands to initiate and sustain alveologenesis.

After PNX, Activation of PCECs Supports Expansion of Epithelial Progenitor Cells.

Using a PNX-induced alveolar regeneration model, endothelial-specific knock down of Vegfr2 and Fgfr1, and 3-dimensional endothelial-epithelial coculture angiosphere bioreactors, the inventors have established the essential role of the PCECs in promoting regenerative alveologenesis. The studies described herein have uncovered the angiocrine role of MMP14, which by shedding HB-EGF and generating an EGF-like fragment from laminin5 γ2 chain, stimulates amplification of lung epithelial progenitor cells, including subsets of BASCs and AECs, supporting alveolarization. The role of MMP14/EGFR activation in promoting alveologenesis was confirmed in studies in which EGF administration into Vegfr2$^{i\Delta EC/i\Delta EC}$Fgfr1$^{i\Delta EC/+}$ mice restored alveolar regeneration after PNX. Moreover, the inventors established a lung PCEC transplantation model to define the essential role of functionally incorporated PCECs in restoring epithelialization in mice with impaired capacity to undergo neoalveolarization. Taken together, the inventors have demonstrated that after PNX, PCECs orchestrate regenerative alveolarization by formation of new vessels and through instructive production of epithelial-active angiocrine factors.

PNX Induces Alveolar Regeneration Via Amplification of Epithelial Progenitor Cells.

At early phases (day 0-3), PNX induces expansion of CCSP$^+$SPC$^+$Sca-1$^+$CD31$^-$VE-cadherin$^-$ BASC-like cells localized at BADJ. At later phases (day 7-15), SPCE-cadherin$^+$ AECIIs and PCECs expand, reestablishing functional alveolar-capillary units. Upon MMP14 inhibition, loss of alveolar coverage of not only cuboidal SPC$^+$E-cadherin$^+$, but also squamous SPC$^-$E-cadherin$^+$ AEC implicates that transiently amplified SPCE-cadherin$^+$ AECIIs potentially generate SPC$^-$E-cadherin$^+$ type I AECs (Beers, The Journal of clinical investigation 121: 2065-2073 (2011); Morrisey, Developmental cell 18:8-23 (2010); Rock, Annual review of cell and developmental biology (2011)), leading to full reconstitution of alveolar surface after PNX. Therefore, inductive PCECs drive regeneration of specialized lung epithelial cells that collectively rebuild functional alveolar-capillary sacs.

PCECs Initiate Alveologenesis Through MMP14-Mediated Release of EGFR Ligands.

PCEC-derived MMP14 is required for the expansion of epithelial cells and restoration of alveolar structure and pulmonary function. In mouse fetal lung, MMP14 regulates alveolar formation (Atkinson, Dev Dyn 232:1079-1090 (2005); Irie, Medical molecular morphology 38:43-46 (2005); Oblander, Developmental biology 277:255-269 (2005)), by provoking epithelial proliferation and migration (Chun, Cell 125:577-591 (2006); Hiraoka, Cell 95:365-377 (1998); Stratman, Blood 114:237-247 (2009); Yana, Journal of cell science 120:1607-1614 (2007)). Postnatally, MMP14 deficient mice exhibit defective alveolarization, abnormal sacculation, and impaired vascular integration with AECs, suggesting that MMP14 mediates alveolar-capillary crosstalk (Lee, Nature medicine 10:1095-1103 (2004); Li, Cell 111:635-646 (2002); Morris, Nature 422:169-173 (2003); Page-McCaw, Nature reviews 8:221-233 (2007)). Thus, the inventors have shown that after PNX, inhibition of MMP14 interfered with alveolar regrowth but not endothelial proliferation, leading to enlarged alveolar size. Although MMP14 may be dispensable for proliferative angiogenesis, it plays a key role in inducing regenerative alveolarization. These studies demonstrate that the mechanism by which MMP14 modulates alveologenesis involves shedding of HB-EGF into the alveolar space and generation of an EGF-like fragment from laminin5 γ2 chain. Subsequently, an increase in bioavailable EGFR-ligands initiates regeneration of epithelial progenitors. In this regard, MMP14 performs as a PCEC-specific angiocrine cue that drives regenerative alveolarization.

PCEC-Specific Induction of MMP14 Defines Unique Functional Signature of Lung Vasculature.

Each organ is vascularized by specialized populations of capillary ECs identified by unique phenotypic, functional and structural attributes. Bone marrow (Butler, Cell stem cell 6:251-264 (2010b); Hooper, Cell stem cell 4: 263-274 (2009)) and liver SECs, which are demarcated by VEGFR2$^+$VEGFR3$^+$VE-cadherin$^+$ vessels, express defined sets of angiocrine factors driving organ regeneration. As described above, after partial hepatectomy, VEGFR2$^-$ and Id1$^-$ inductive liver SECs produce HGF and WNT2 to induce hepatocyte proliferation. In contrast, bone marrow VEGFR2$^-$ inductive SECs express Notch ligands and IGFBPs (Butler, Cell stem cell 6:251-264 (2010b); Kobayashi, Nature cell biology 12:1046-1056 (2010)) to induce reconstitution of hematopoietic cells.

PCECs have a distinct phenotypic signature identified as VEGFR2$^+$FGFR1$^+$CD34$^+$VE$^-$cadherin$^+$ vessels. Remarkably, after PNX, the production of MMP14 is restricted to VEGFR2- and FGFR1-activated PCECs but not other vascular rich organs, highlighting a unique functional signature of PCECs in alveolar regeneration. The negligible effect of plasma obtained from pneumonectomized WT mice in restoring alveologenesis demonstrated the minimal contribution of systemic soluble growth factor(s) from non-pulmonary vasculature in mediating alveologenesis. These data clearly set forth the notion that PNX turns on a PCEC-specific program to promote alveolar regeneration.

Sequential Activation of VEGFR2 and FGFR1 Primes PCECs During Alveolar Regeneration.

The mechanism by which PCECs are induced to express MMP14 after PNX is mediated by hierarchical activation and upregulation of VEGFR2 and FGFR1. At the early phase of PNX, expansion of BASC-like cells is largely dependent on activation of VEGFR2 in PCECs, which causes upregulation of MMP14 without inducing EC proliferation. In contrast to early activation and stable expression of VEGFR2 after PNX, FGFR1 expression level is induced thereafter, peaking at day 7. FGFR1 synergizes with VEGFR2 in augmenting MMP14 generation, thereby sustaining alveolar regeneration. Sequential activation of VEGFR2 and FGFR1 in PCECs therefore induces MMP14 production, fostering regeneration of the functional alveolar-capillary units.

PCEC Transplantation and Administration of PCEC-Derived Angiocrine Factors Offers New Approaches for Treatment of Respiratory Diseases.

Development of therapeutic strategies to repair respiratory capacity in patients with pulmonary disorders is handicapped by lack of understanding of lung regeneration mechanisms (Jiang, Nature medicine 11:1173-1179 (2005); Kajstura, The New England journal of medicine 364:1795-1806 (2011); Matthay, Annual review of pathology 6:147-163 (2011); Morris, Nature 422:169-173 (2003); Petrache, Nature medicine 11:491-498 (2005); Whitsett, Annual review of medicine 61:105-119 (2010)). The studies described herein demonstrate that after PNX, inductive PCECs play a seminal role in restoring respiratory capacity, as measured by inspiratory volume and static compliance.

Notably, administration of EGF or transplantation of inductive PCECs improved respiratory function in mice. Thus, transplantation of properly activated PCECs or injection of lung-specific angiocrine mediators can improve lung function in subsets of patients with pulmonary disorders.

The studies described in Example 2 show that PCECs orchestrate regenerative alveologenesis by relaying inductive angiocrine growth signals such as MMP14. Selective activation of VEGFR2 and FGFR1, or increase in the production of MMP14, as well as other angiocrine factors as described herein can facilitate lung alveolarization, thereby improving hypoxemia in patients with debilitating lung diseases.

The invention claimed is:

1. A method of enhancing or initiating lung regeneration, comprising administering a substantially purified population of matrix metalloproteinase-14 positive (MMP14+) inductive pulmonary endothelial cells to a subject in need of lung regeneration, wherein
the subject has a defect in or deficiency of non-endothelial cells within the lung, and
wherein following the administration, the proliferation or function of non-endothelial cells within the lung is enhanced or improved.

2. The method of claim 1, wherein said administering is intravenous or intratracheal transplantation.

3. The method of claim 2, further comprising administration of one or more of MMP14, vascular endothelial growth factor-A (VEGF-A), or fibroblast growth factor (FGF).

4. The method of claim 2, further comprising administration of epithelial progenitor cells.

5. The method of claim 2, wherein said endothelial cells are vascular endothelial growth factor receptor 2 positive (VEGFR2+), VE-cadherin+, CD34+, CD31+, and fibroblast growth factor receptor 1-positive (FGFR1+).

6. The method of claim 2, further comprising obtaining the endothelial cells by selection of MMP14+ cells, prior to administration of said substantially purified cells to said subject.

7. The method of claim 6, further comprising culturing the endothelial cells prior to administration of said cells.

8. The method of any one of claim 1, 2-3 or 5-7 wherein the endothelial cells have been transfected or transduced with E4 open reading frame 1 (E4ORF1).

* * * * *